(12) United States Patent
Wang et al.

(10) Patent No.: US 11,365,242 B2
(45) Date of Patent: Jun. 21, 2022

(54) ANTI-APELIN ANTIBODIES AND USES THEREOF

(71) Applicant: Phanes Therapeutics, Inc., San Diego, CA (US)

(72) Inventors: Minghan Wang, San Diego, CA (US); Hui Zou, Dallas, TX (US); Arvin Tam, San Diego, CA (US)

(73) Assignee: Phanes Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/639,808

(22) PCT Filed: Aug. 21, 2018

(86) PCT No.: PCT/US2018/047144
§ 371 (c)(1),
(2) Date: Feb. 18, 2020

(87) PCT Pub. No.: WO2019/040390
PCT Pub. Date: Feb. 28, 2019

(65) Prior Publication Data
US 2020/0362021 A1    Nov. 19, 2020

Related U.S. Application Data

(60) Provisional application No. 62/658,111, filed on Apr. 16, 2018, provisional application No. 62/656,586, (Continued)

(51) Int. Cl.
*C07K 16/18* (2006.01)
*C07K 16/28* (2006.01)
(Continued)

(52) U.S. Cl.
CPC ............ *C07K 16/18* (2013.01); *A61P 9/10* (2018.01); *A61P 27/02* (2018.01); *G01N 33/74* (2013.01); *A61K 45/06* (2013.01)

(58) Field of Classification Search
None
See application file for complete search history.

(56) References Cited

U.S. PATENT DOCUMENTS

2016/0053000 A1    2/2016 Lu et al.
2016/0130327 A1    5/2016 Fu et al.

FOREIGN PATENT DOCUMENTS

WO    2013012855 A1    1/2013

OTHER PUBLICATIONS

Kussie et al., A single engineered amino acid substitution changes antibody fine specificity.J Immunol. Jan. 1, 1994;152(1):146-52. (Year: 1994).*

(Continued)

*Primary Examiner* — Aurora M Fontainhas
(74) *Attorney, Agent, or Firm* — Ice Miller LLP

(57) ABSTRACT

Anti-apelin antibodies and antigen-binding fragments thereof are described. Also described are nucleic acids encoding the antibodies, compositions comprising the antibodies, and methods of producing the antibodies and using the antibodies for treating or preventing diseases such as diabetic retinopathy (DR), including proliferative diabetic retinopathy (PDR) and non-proliferative diabetic retinopathy (NPDR), age-related macular degeneration (AMD), diabetic macular edema (DME), macular edema following retinal vein occlusion (RVO), retinal degeneration, myopic choroidal neovascularization (mCNV), diabetic nephropathy, chronic kidney disease (CKD), non-alcoholic steatohepatitis (NASH), liver cirrhosis, plaque neovascularization, rubeosis iridis, neovascular glaucoma, corneal neovascular- (Continued)

ization (CNV), retinopathy of prematurity (ROP), retinopathy, macular degeneration, ovarian hyperstimulation syndrome (OHSS), uterine bleeding, endometriosis, endometrial hyperplasia and cancer, myometrial leiomyomas, adenomyosis, cancer (e.g., solid tumors and hematologic malignancies), fibrosis, and/or associated complications.

36 Claims, 16 Drawing Sheets

Specification includes a Sequence Listing.

Related U.S. Application Data filed on Apr. 12, 2018, provisional application No. 62/579,287, filed on Oct. 31, 2017, provisional application No. 62/549,523, filed on Aug. 24, 2017.

(51) Int. Cl.

| | | |
|---|---|---|
| A61K 39/395 | (2006.01) | |
| A61P 27/02 | (2006.01) | |
| A61P 9/10 | (2006.01) | |
| G01N 33/74 | (2006.01) | |
| A61K 45/06 | (2006.01) | |

(56) References Cited

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18. (Year: 2003).*
Chen et al., Enhancement and destruction of antibody function by somatic mutation: unequal occurrence is controlled by V gene combinatorial associations. EMBO J. Jun. 15, 1995;14(12):2784-94. (Year: 1995).*
Guo et al., "Apelin promotes diabetic nephropathy by inducing podocyte dysfunction via inhibiting proteasome activities," J Cell Mol Med. 19(9):2273-85 (2015).
Habata et al., "Apelin, the natural ligand of the orphan receptor APJ, is abundantly secreted in the colostrum," Biochimica et Biophysica Acta 1452(1):25-35 (1999).
Iturrioz et al., "By Interacting with the C-terminal Phe of Apelin, Ph255 and Trp259 in Helix VI of the Apelin Receptor Are Critical for Internalization," J Biol Chem. 285(42):32627-37 (2010).
Kalin et al., "Paracrine and autocrine mechanisms of apelin signaling govern embryonic and tumor angiogenesis," Dev Biol. 305(2):599-614 (2007).
Kasai et al., "Retardation of Retinal Vascular Development in Apelin-Deficient Mice," Arterioscler Thromb Vasc Biol. 28(10):1717-22 (2008).
Kasai et al., "Apelin Is a Crucial Factor for Hypoxia-Induced Retinal Angiogenesis," Arterioscler Thromb Vasc Biol. 30(11):2182-7 (2010).
Kasai et al., "Apelin is a novel angiogenic factor in retinal endothelial cells," Biochem Biophys Res Commun. 325(2):395-400 (2004).
Kidoya et al., "Spatial and temporal role of the apelin/APJ system in the caliber size regulation of blood vessels during angiogenesis," EMBO J. 27(3):522-34 (2008).
Lee et al., "Characterization of Apelin, the Ligand for the APJ Receptor," J. Neurochem. 74(1):34-41 (2000).
Li et al., "Apelin-induced vascular smooth muscle cell proliferation: the regulation of cyclin D1," Front Biosci. 13:3786-92 (2008).
Liu et al., "Apelin-13 upregulates Egr-1 expression in rat vascular smooth muscle cells through the PI3K/Akt and PKC signaling pathways," Biochem Biophys Res Commun. 468(4):617-21 (2015).
Liu et al., "Apelin involved in progression of diabetic nephropathy by inhibiting autophagy in podocytes," Cell Death Dis. 8(8):e3006 (2017).
Masri et al., "Apelin (65-77) Activates Extracellular Signal-Regulaled Kinases via a PTX-Sensitive G Protein," Biochem Biophys Res Commun. 290(1):539-45 (2002).
Masri et al., "Apelin (65-77) activates p70 S6 kinase and is mitogenic for umbilical endothelial cells," FASEB J. 18(15):1909-11 (2004).
Medhurst et al., "Pharmacological and immunohistochemical characterization of the APJ receptor and its endogenous ligand apelin," J Neurochem. 84(5):1162-72 (2003).
Melgar-Lesmes et al., "Apelin Mediates the Induction of Profibrogenic Genes in Human Hepatic Stellate Cells," Endocrinology, 151(11):5306-14 (2010).
Mesmin et al., "Identification and Characterization of Apelin Peptides in Bovine Colostrum and Milk by Liquid Chromatography—Mass Spectrometry," J Proteome Res. 10(11):5222-31 (2011).
Muto et al., "The Apelin-APJ System Induces Tumor Arteriogenesis in Hepatocellular Carcinoma," Anticancer Res. 34(10):5313-20 (2014).
O'Carroll et al., "The apelin receptor APJ: journey from an orphan to a multifaceted regulator of homeostasis," J Endocrinol. 219(1):R13-35 (2013).
Picault et al., "Tumour co-expression of apelin and its receptor is the basis of an autocrine loop involved in the growth of colon adenocarcinomas," Eur J Cancer. 50(3):663-74 (2014).
Principe et al., "The Hepatic Apelin System: A New Therapeutic Target for Liver Disease," Hepatology. 48(4):1193-201 (2008).
Saint-Geniez et al., "Expression of the murine msr/apj receptor and its ligand apelin is upregulated during formation of the retinal vessels," Mech Dev. 110(1-2):183-6 (2002).
Shin et al., "Bioactivity of the putative apelin proprolein expands the repertoire of apelin receptor ligands," Biochimica et Biophysica Acta. 1861(8):1901-12 (2017).
Sorli et al., "Therapeutic potential of interfering with apelin signalling," Drug Discov Today 11(23/24):1100-6 (2006).
Sorli et al., "Apelin is a potent activator of tumour neoangiogenesis," Oncogene 26(55):7692-9 (2007).
Tao et al., "Apelin in Plasma and Vitreous and in Fibrovascular Retinal Membranes of Patients with Proliferative Diabetic Retinopathy," Invest Ophthalmol Vis Sci. 51(8):4237-42 (2010).
Tatemoto et al., "Isolation and Characterization of a Novel Endogenous Peptide Ligand for the Human APJ Receptor," Biochem Biophys Res. Commun. 251(2):471-6 (1998).
Yokomori et al., "Overexpression of apelin receptor (APJ/AGTRL1) on hepatic stellate cells and sinusoidal angiogenesis in human cirrhotic liver," J Gastroenterol. 46(2):222-31 (2011).
Zuurbier et al., "Apelin: A putative novel predictive biomarker for bevacizumab response in colorectal cancer," Oncotarget. 8(26):42949-42961 (2017).
De Mota, et al., "Cloning, Pharmacological Characterization and Brain Distribution of the Rat Apelin Receptor," Neuroendocrinology 72(6):400-7 (2000).
International Search Report and Written Opinion dated Dec. 14, 2018 in International Application No. PCT/US2018/047144.
Polyketide Synthase [*Streptomyces* sp. SN-593]. GenBank: BAK64637.1. Jan. 9, 2011; downloaded from the Internet < https://www.ncbi.nlm.nih.gov/protein/BAK64637.1?report=genbank&log$=protalign&blast_rank=1&RID=X6GBJJFY014> on Oct. 26, 2018, pp. 1-4.
Antibody Variable Domain, Partial [Oryctolagus Cuniculus]. GenBank: AAO06456.1, Jul. 24, 2016; downloaded from the internet < https://www.ncbi.nlm.nih.gov/protein/AAO06456.1?report=genbank&log$=protalign&blast_rank=1&RID=X6GT12HG015> on Oct. 26, 2018, p. 1.

\* cited by examiner

SEQUENCE LISTING

<160> NUMBER OF SEQ ID NOS: 221

<210> SEQ ID NO 1
<211> LENGTH: 113
<212> TYPE: PRT
<213> ORGANISM: Artificial Sequence
<220> FEATURE:
<223> OTHER INFORMATION: C8 Heavy Chain Variable Region

<400> SEQUENCE: 1

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Tyr Ser Asn Arg

```
                    20                  25                  30
Met Ser Trp Val Arg Gln Ala Pro Gly Lys Gly Leu Glu Trp Ile Gly
                35                  40                  45

Ser Ile Gly Ser Ser Pro Trp Tyr Ala Ser Trp Ala Gln Gly Arg Phe
            50                  55                  60

Thr Ile Ser Lys Thr Ser Ser Thr Val Asn Leu Lys Ile Thr Ser
65                  70                  75                  80

Pro Thr Thr Glu Asp Thr Ala Thr Tyr Phe Cys Ala Lys Gly Gly Tyr
                85                  90                  95

Arg Pro Gly Ala Ser Val Trp Gly Pro Gly Thr Leu Val Thr Val Ser
                100                 105                 110

Ser
```

<210> SEQ ID NO 2
<211> LENGTH: 109
<212> TYPE: PRT
<213> ORGANISM: Artificial Sequence
<220> FEATURE:
<223> OTHER INFORMATION: C8 Light Chain Variable Region

<400> SEQUENCE: 2

```
Gln Val Leu Thr Gln Thr Glu Ser Pro Val Ser Ala Pro Val Gly Gly
1               5                   10                  15

Thr Val Thr Ile Ala Cys Gln Ser Ser Gln Ser Val Tyr Asp Asn Asn
                20                  25                  30

Asp Leu Ala Trp Tyr Gln Gln Lys Ala Gly Gln Thr Pro Lys Arg Leu
            35                  40                  45

Ile Tyr Leu Ala Ser Ser Leu Asp Ser Gly Val Pro Ser Arg Phe Lys
        50                  55                  60

Gly Ser Gly Ser Gly Thr Glu Phe Thr Leu Thr Ile Ser Asp Leu Glu
65                  70                  75                  80

Cys Asp Asp Ala Ala Thr Tyr Tyr Cys Ala Gly Gly Tyr Ser Gly Asp
                85                  90                  95

Ile Tyr Thr Phe Gly Gly Gly Thr Glu Val Val Val Glu
                100                 105
```

<210> SEQ ID NO 3
<211> LENGTH: 112
<212> TYPE: PRT
<213> ORGANISM: Artificial Sequence
<220> FEATURE:
<223> OTHER INFORMATION: C24 Heavy Chain Variable Region

<400> SEQUENCE: 3

```
Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Tyr Thr Asn Arg
                20                  25                  30

Val Ser Trp Val Arg Gln Ala Pro Gly Lys Gly Leu Asp Trp Ile Gly
            35                  40                  45

Ser Ile Gly Ser Ser Pro Trp Tyr Ala Ser Trp Ala Gln Gly Arg Phe
        50                  55                  60

Thr Ile Ser Lys Thr Ser Thr Val Asn Leu Lys Ile Thr Ser Ser
65                  70                  75                  80

Thr Thr Glu Asp Thr Ala Thr Tyr Phe Cys Ala Lys Gly Gly Tyr Arg
                85                  90                  95

Pro Gly Gly Ser Ile Trp Gly Pro Gly Thr Leu Val Thr Val Ser Ser
```

-continued

```
                100                 105                 110
```

<210> SEQ ID NO 4
<211> LENGTH: 109
<212> TYPE: PRT
<213> ORGANISM: Artificial Sequence
<220> FEATURE:
<223> OTHER INFORMATION: C24 Light Chain Variable Region

<400> SEQUENCE: 4

```
Gln Val Leu Thr Gln Ser Ala Ser Pro Val Ser Ala Val Gly Asp
1               5                   10                  15

Ser Val Thr Ile Ala Cys Gln Ser Gln Ser Val Tyr Asp Asn Asn
                20                  25                  30

Asp Leu Gly Trp Tyr Gln Gln Lys Pro Gly Gln Thr Pro Lys Arg Leu
            35                  40                  45

Ile Tyr Leu Ala Ser Ser Leu Asp Ser Gly Val Pro Ser Arg Phe Ser
        50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Ala Gly Gly Tyr Ser Gly Asp
                85                  90                  95

Ile Tyr Thr Phe Gly Gly Gly Thr Glu Val Val Val Lys
                100                 105
```

<210> SEQ ID NO 5
<211> LENGTH: 112
<212> TYPE: PRT
<213> ORGANISM: Artificial Sequence
<220> FEATURE:
<223> OTHER INFORMATION: C25 Heavy Chain Variable Region

<400> SEQUENCE: 5

```
Gln Ser Leu Glu Glu Ser Gly Gly Leu Val Thr Pro Gly Thr Pro
1               5                   10                  15

Leu Thr Leu Thr Cys Thr Val Ser Gly Ile Asp Leu Tyr Thr Asn Arg
                20                  25                  30

Met Ser Trp Val Arg Gln Ala Pro Gly Lys Gly Leu Glu Trp Ile Gly
            35                  40                  45

Ser Ile Gly Ser Ser Pro Trp Phe Ala Ser Trp Ala Leu Gly Arg Phe
        50                  55                  60

Thr Ile Ser Lys Thr Ser Thr Thr Val Asn Leu Lys Ile Thr Ser Pro
65                  70                  75                  80

Thr Thr Glu Asp Thr Ala Thr Tyr Phe Cys Ala Lys Gly Gly Tyr Arg
                85                  90                  95

Pro Gly Ala Ser Val Trp Gly Pro Gly Thr Leu Val Thr Val Ser Ser
                100                 105                 110
```

<210> SEQ ID NO 6
<211> LENGTH: 109
<212> TYPE: PRT
<213> ORGANISM: Artificial Sequence
<220> FEATURE:
<223> OTHER INFORMATION: C25 Light Chain Variable Region

<400> SEQUENCE: 6

```
Gln Val Leu Thr Gln Thr Glu Ser Pro Val Ser Ala Pro Val Gly Gly
1               5                   10                  15

Thr Val Thr Ile Ala Cys Gln Ser Ser Gln Ser Val Tyr Asp Asn Asn
                20                  25                  30
```

Asp Leu Ala Trp Tyr Gln Gln Lys Ala Gly Gln Thr Pro Lys Arg Leu
        35                  40                  45

Ile Phe Leu Ala Ser Ser Leu Asp Ser Gly Val Pro Ser Arg Phe Lys
    50                  55                  60

Gly Ser Gly Ser Gly Thr Glu Phe Thr Leu Thr Ile Ser Asp Leu Glu
65                  70                  75                  80

Cys Asp Asp Ala Ala Thr Tyr Tyr Cys Ala Gly Gly Tyr Asn Gly Asp
                85                  90                  95

Ile Tyr Thr Phe Gly Gly Gly Thr Glu Val Val Val Lys
            100                 105

<210> SEQ ID NO 7
<211> LENGTH: 115
<212> TYPE: PRT
<213> ORGANISM: Artificial Sequence
<220> FEATURE:
<223> OTHER INFORMATION: C7 Heavy Chain Variable Region

<400> SEQUENCE: 7

Gln Ser Leu Glu Glu Ser Gly Gly Arg Leu Ala Lys Pro Asp Glu Thr
1               5                   10                  15

Leu Thr Leu Thr Cys Thr Val Ser Gly Ile Asp Leu Asn Ser His Ala
            20                  25                  30

Met Asp Trp Val Arg Gln Ala Pro Gly Lys Gly Leu Glu Trp Ile Gly
        35                  40                  45

Val Ile Ala Pro Asp Thr Arg Thr Tyr Tyr Ala Thr Trp Ala Arg Gly
    50                  55                  60

Arg Phe Thr Ile Ser Lys Thr Ser Ser Thr Val Glu Leu Lys Met
65                  70                  75                  80

Thr Ser Leu Thr Thr Glu Asp Thr Ala Thr Tyr Phe Cys Ala Ala Tyr
                85                  90                  95

Pro Ile Glu Pro Gly Ala Asn Ile Trp Gly Pro Gly Thr Leu Val Thr
            100                 105                 110

Val Ser Ser
        115

<210> SEQ ID NO 8
<211> LENGTH: 110
<212> TYPE: PRT
<213> ORGANISM: Artificial Sequence
<220> FEATURE:
<223> OTHER INFORMATION: C7 Light Chain Variable Region

<400> SEQUENCE: 8

Asp Pro Val Leu Thr Gln Thr Pro Ser Pro Val Ser Ala Pro Val Gly
1               5                   10                  15

Gly Thr Val Thr Ile Gly Cys Gln Ala Ser Glu Ser Val Asp Tyr Asn
            20                  25                  30

Asn Gln Leu Ser Trp Tyr Gln Gln Lys Pro Gly Gln Ala Pro Lys Arg
        35                  40                  45

Leu Met Tyr Tyr Val Ser Thr Leu Asp Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Gln Gly Gly Tyr Pro Tyr
                85                  90                  95

Asn Ile Tyr Pro Phe Gly Gly Gly Thr Glu Val Val Val Lys

<210> SEQ ID NO 9
<211> LENGTH: 115
<212> TYPE: PRT
<213> ORGANISM: Artificial Sequence
<220> FEATURE:
<223> OTHER INFORMATION: C6 Heavy Chain Variable Region

<400> SEQUENCE: 9

```
Gln Ser Leu Glu Glu Ser Gly Gly Arg Leu Val Lys Pro Asp Glu Thr
1               5                   10                  15
Leu Thr Leu Thr Cys Thr Val Ser Gly Ile Asp Leu Ser Asn Tyr Ala
            20                  25                  30
Met Asp Trp Val Arg Gln Ala Pro Gly Lys Gly Leu Glu Trp Ile Gly
        35                  40                  45
Val Ile Ala Pro Asn Arg Arg Thr Tyr Tyr Pro Thr Trp Ala Arg Gly
    50                  55                  60
Arg Phe Thr Ile Ser Lys Thr Ser Thr Thr Val Asp Leu Lys Met
65                  70                  75                  80
Thr Ser Leu Thr Thr Glu Asp Thr Ala Thr Tyr Phe Cys Ala Thr Tyr
                85                  90                  95
Pro Ile Glu Pro Gly Ala Asn Ile Trp Gly Pro Gly Thr Leu Val Thr
            100                 105                 110
Val Ser Ser
        115
```

<210> SEQ ID NO 10
<211> LENGTH: 110
<212> TYPE: PRT
<213> ORGANISM: Artificial Sequence
<220> FEATURE:
<223> OTHER INFORMATION: C6 Light Chain Variable Region

<400> SEQUENCE: 10

```
Asp Pro Val Leu Thr Gln Thr Pro Ser Pro Val Ser Ala Pro Val Gly
1               5                   10                  15
Gly Thr Val Thr Ile Gly Cys Gln Ser Ser Glu Ser Val Asp Tyr Asn
            20                  25                  30
Asn Gln Leu Ser Trp Tyr Gln Gln Lys Pro Gly Gln Pro Pro Lys Arg
        35                  40                  45
Leu Met Tyr Tyr Val Ser Thr Leu Asp Ser Gly Val Pro Ser Arg Phe
    50                  55                  60
Lys Gly Ser Gly Ser Gly Thr Gln Phe Thr Leu Thr Ile Ser Asp Leu
65                  70                  75                  80
Glu Cys Asp Asp Ala Ala Thr Tyr Tyr Cys Gln Gly Gly Tyr Ile Ser
                85                  90                  95
Asn Ile Tyr Pro Phe Gly Gly Gly Thr Glu Val Val Val Lys
            100                 105                 110
```

<210> SEQ ID NO 11
<211> LENGTH: 114
<212> TYPE: PRT
<213> ORGANISM: Artificial Sequence
<220> FEATURE:
<223> OTHER INFORMATION: C1 Heavy Chain Variable Region

<400> SEQUENCE: 11

```
Gln Ser Leu Glu Glu Ser Gly Gly Arg Leu Val Thr Pro Gly Gly Ser
1               5                   10                  15
```

Leu Thr Leu Thr Cys Thr Val Ser Gly Phe Ser Leu Ser Ser Tyr Ala
                20                  25                  30

Met Asp Trp Val Arg Gln Ala Pro Gly Lys Gly Leu Glu Trp Ile Gly
            35                  40                  45

Val Ile Ala Pro Asn Gly Ala Thr Tyr Tyr Pro Thr Trp Ala Arg Gly
50                  55                  60

Arg Phe Thr Ile Ser Lys Thr Ser Thr Val Asp Leu Lys Met Thr
65                  70                  75                  80

Ser Leu Thr Ala Ala Asp Thr Ala Thr Tyr Phe Cys Ala Thr Tyr Pro
                85                  90                  95

Ile Asp Ala Gly Ala Asn Ile Trp Gly Pro Gly Thr Leu Val Thr Val
                100                 105                 110

Ser Ser

<210> SEQ ID NO 12
<211> LENGTH: 110
<212> TYPE: PRT
<213> ORGANISM: Artificial Sequence
<220> FEATURE:
<223> OTHER INFORMATION: C1 Light Chain Variable Region

<400> SEQUENCE: 12

Asp Pro Val Leu Thr Gln Thr Pro Ser Ser Val Ser Ala Ala Val Gly
1               5                   10                  15

Gly Thr Val Thr Ile Gly Cys Gln Ser Ser Glu Ser Val Asp Asn Asn
                20                  25                  30

Asn Gln Leu Ser Trp Tyr Gln Gln Lys Ser Gly Gln Pro Pro Lys Arg
            35                  40                  45

Leu Met Tyr Tyr Val Ser Thr Leu Asp Ser Gly Val Pro Ser Arg Phe
50                  55                  60

Lys Gly Ser Gly Ser Gly Thr His Phe Thr Leu Thr Ile Ser Gly Val
65                  70                  75                  80

Gln Cys Tyr Asp Ala Ala Thr Tyr Tyr Cys Gln Gly Gly Tyr Ile Ser
                85                  90                  95

Asn Leu Tyr Pro Phe Gly Gly Gly Thr Glu Val Val Val Lys
                100                 105                 110

<210> SEQ ID NO 13
<211> LENGTH: 114
<212> TYPE: PRT
<213> ORGANISM: Artificial Sequence
<220> FEATURE:
<223> OTHER INFORMATION: C16 Heavy Chain Variable Region

<400> SEQUENCE: 13

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Asn Ser Tyr Ala
                20                  25                  30

Met Asp Trp Val Arg Gln Ala Pro Gly Lys Gly Leu Glu Trp Ile Gly
            35                  40                  45

Val Ile Ala Pro Asn His Tyr Thr Tyr Tyr Pro Thr Trp Ala Arg Gly
50                  55                  60

Arg Phe Thr Ile Ser Lys Thr Ser Thr Val Asp Leu Lys Met Thr
65                  70                  75                  80

Arg Leu Thr Thr Glu Asp Thr Ala Thr Tyr Phe Cys Ala Thr Tyr Pro
                85                  90                  95

```
Ile Glu Ser Gly Ser Asn Ile Trp Gly Pro Gly Thr Leu Val Ile Val
            100                 105                 110

Ser Ser

<210> SEQ ID NO 14
<211> LENGTH: 110
<212> TYPE: PRT
<213> ORGANISM: Artificial Sequence
<220> FEATURE:
<223> OTHER INFORMATION: C16 Light Chain Variable Region

<400> SEQUENCE: 14

Asp Pro Val Leu Thr Gln Thr Pro Ser Ser Val Ser Ala Ala Val Gly
1               5                   10                  15

Gly Thr Val Thr Ile Gly Cys Gln Ser Ser Glu Ser Val Gly Met Asn
            20                  25                  30

Asn Gln Leu Ser Trp Tyr Gln Gln Lys Pro Gly Gln Pro Pro Lys Arg
        35                  40                  45

Leu Met Tyr Tyr Val Ser Thr Leu Asp Ser Gly Val Pro Ser Arg Phe
    50                  55                  60

Lys Gly Ser Gly Ser Gly Thr Gln Phe Ser Leu Thr Ile Ser Asp Leu
65                  70                  75                  80

Glu Cys Asp Asp Ala Gly Thr Tyr Tyr Cys Gln Gly Gly Tyr Ile Ser
                85                  90                  95

Asn Leu Tyr Pro Phe Gly Gly Gly Thr Glu Val Val Val Lys
            100                 105                 110

<210> SEQ ID NO 15
<211> LENGTH: 114
<212> TYPE: PRT
<213> ORGANISM: Artificial Sequence
<220> FEATURE:
<223> OTHER INFORMATION: C20 Heavy Chain Variable Region

<400> SEQUENCE: 15

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Asn Asn Tyr Ala
            20                  25                  30

Ile Asp Trp Val Arg Gln Ala Pro Gly Lys Gly Leu Glu Trp Ile Gly
        35                  40                  45

Val Ile Ala Pro Asn His Tyr Thr Cys Tyr Pro Thr Trp Ala Arg Gly
    50                  55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Ala Ala Tyr Pro
                85                  90                  95

Ile Glu Thr Gly Ser Asn Ile Trp Gly Pro Gly Thr Leu Val Ile Val
            100                 105                 110

Ser Ser

<210> SEQ ID NO 16
<211> LENGTH: 110
<212> TYPE: PRT
<213> ORGANISM: Artificial Sequence
<220> FEATURE:
<223> OTHER INFORMATION: C20 Light Chain Variable Region

<400> SEQUENCE: 16
```

Asp Pro Met Leu Thr Gln Thr Pro Ser Ser Val Ser Ala Ala Val Gly
1               5                   10                  15

Gly Thr Val Thr Ile Ser Cys Gln Ser Ser Glu Ser Val Asp Met Asn
                20                  25                  30

Asn Gln Leu Ser Trp Tyr Gln Gln Lys Pro Gly Gln Pro Pro Lys Arg
            35                  40                  45

Leu Met Tyr Tyr Val Ser Thr Leu Asp Ser Gly Val Pro Ser Arg Phe
50                      55                  60

Lys Gly Ser Gly Ser Gly Ile His Phe Ser Leu Thr Ile Ser Asp Leu
65                  70                  75                  80

Glu Cys Ala Asp Ala Gly Thr Tyr Tyr Cys Gln Gly Gly Tyr Ile Ser
                85                  90                  95

Asn Leu Tyr Pro Phe Gly Gly Gly Thr Glu Val Val Val Lys
            100                 105                 110

<210> SEQ ID NO 17
<211> LENGTH: 114
<212> TYPE: PRT
<213> ORGANISM: Artificial Sequence
<220> FEATURE:
<223> OTHER INFORMATION: C22 Heavy Chain Variable Region

<400> SEQUENCE: 17

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Asn Asn Tyr Ala
                20                  25                  30

Met Asp Trp Val Arg Gln Ala Pro Gly Lys Gly Leu Glu Trp Ile Gly
            35                  40                  45

Val Ile Ala Pro Asn His Tyr Thr Tyr Tyr Pro Thr Trp Ala Arg Gly
50                      55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Ala Thr Tyr Pro
                85                  90                  95

Ile Glu Thr Gly Ser Asn Ile Trp Gly Pro Gly Thr Leu Val Ile Val
            100                 105                 110

Ser Ser

<210> SEQ ID NO 18
<211> LENGTH: 110
<212> TYPE: PRT
<213> ORGANISM: Artificial Sequence
<220> FEATURE:
<223> OTHER INFORMATION: C22 Light Chain Variable Region

<400> SEQUENCE: 18

Asp Pro Val Leu Thr Gln Thr Pro Ser Ser Val Ser Ala Ala Val Gly
1               5                   10                  15

Gly Thr Val Thr Ile Ser Cys Gln Ser Ser Glu Ser Val Asp Met Asn
                20                  25                  30

Asn Gln Leu Ser Trp Tyr His Gln Lys Ser Gly Gln Pro Pro Lys Arg
            35                  40                  45

Leu Met Tyr Tyr Val Ser Thr Leu Asp Ser Gly Val Pro Ser Arg Phe
50                      55                  60

Lys Gly Ser Gly Ser Gly Thr Gln Phe Thr Leu Thr Ile Ser Gly Val
65                  70                  75                  80

Gln Cys Asp Asp Ala Gly Thr Tyr Tyr Cys Gln Gly Tyr Ile Ser
                85                  90                  95

Asn Leu Tyr Pro Phe Gly Gly Gly Thr Glu Val Val Val Lys
            100                 105                 110

<210> SEQ ID NO 19
<211> LENGTH: 114
<212> TYPE: PRT
<213> ORGANISM: Artificial Sequence
<220> FEATURE:
<223> OTHER INFORMATION: C10 Heavy Chain Variable Region

<400> SEQUENCE: 19

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Asn Ser Tyr Ala
                20                  25                  30

Ile Asp Trp Val Arg Gln Ala Pro Gly Lys Gly Leu Glu Trp Ile Gly
            35                  40                  45

Val Ile Ala Pro Ser Gly Thr Thr Tyr Tyr Pro Thr Trp Ala Lys Gly
        50                  55                  60

Arg Phe Thr Ile Ser Lys Thr Ser Thr Thr Val Asp Leu Lys Val Thr
65                  70                  75                  80

Gly Leu Thr Thr Glu Asp Thr Ala Thr Tyr Phe Cys Ala Ala Tyr Pro
                85                  90                  95

Ile Asp Pro Gly Ser Asn Ile Trp Gly Pro Gly Thr Leu Val Thr Val
            100                 105                 110

Ser Ser

<210> SEQ ID NO 20
<211> LENGTH: 110
<212> TYPE: PRT
<213> ORGANISM: Artificial Sequence
<220> FEATURE:
<223> OTHER INFORMATION: C10 Light Chain Variable Region

<400> SEQUENCE: 20

Asp Pro Val Leu Thr Gln Thr Pro Ser Ser Val Ser Ala Ala Val Gly
1               5                   10                  15

Gly Thr Ala Thr Ile Gly Cys Gln Ser Ser Glu Ser Val Asp Tyr Gly
                20                  25                  30

Asn Gln Leu Ser Trp Tyr Gln Gln Lys Pro Gly Gln Pro Pro Lys Arg
            35                  40                  45

Leu Ala Tyr Tyr Val Ser Ile Leu Asp Ala Gly Val Pro Ser Arg Phe
        50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Gln Gly Tyr Ile Ser
                85                  90                  95

Asn Leu Tyr Pro Phe Gly Gly Gly Thr Glu Val Val Val Gln
            100                 105                 110

<210> SEQ ID NO 21
<211> LENGTH: 115
<212> TYPE: PRT
<213> ORGANISM: Artificial Sequence
<220> FEATURE:
<223> OTHER INFORMATION: C12 Heavy Chain Variable Region

```
<400> SEQUENCE: 21

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Ser Ser Tyr Ala
            20                  25                  30

Ile Asp Trp Val Arg Gln Ala Pro Gly Lys Gly Leu Glu Trp Ile Gly
        35                  40                  45

Val Ile Ala Pro Ser Ser Thr Thr Tyr Tyr Pro Thr Trp Ala Lys Gly
    50                  55                  60

Arg Phe Thr Ile Ser Lys Thr Ser Ser Thr Thr Val Asp Leu Lys Val
65                  70                  75                  80

Ile Gly Leu Thr Thr Glu Asp Thr Ala Thr Tyr Phe Cys Ala Ala Tyr
                85                  90                  95

Pro Ile Asp Pro Gly Ser Asn Val Trp Gly Pro Gly Thr Leu Val Thr
            100                 105                 110

Val Ser Ser
        115

<210> SEQ ID NO 22
<211> LENGTH: 110
<212> TYPE: PRT
<213> ORGANISM: Artificial Sequence
<220> FEATURE:
<223> OTHER INFORMATION: C12 Light Chain Variable Region

<400> SEQUENCE: 22

Asp Pro Val Leu Thr Gln Thr Pro Ser Ser Val Ser Ala Ala Val Gly
1               5                   10                  15

Gly Thr Val Thr Ile Gly Cys Gln Ser Ser Glu Ser Val Asp Tyr Gly
            20                  25                  30

Asn Gln Leu Ser Trp Tyr Gln Gln Lys Pro Gly Gln Pro Pro Lys Arg
        35                  40                  45

Leu Thr Tyr Tyr Val Ser Ile Leu Asp Ala Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Gln Gly Gly Tyr Ile Ser
                85                  90                  95

Asn Leu Tyr Pro Phe Gly Gly Gly Thr Glu Val Val Val Gln
            100                 105                 110

<210> SEQ ID NO 23
<211> LENGTH: 115
<212> TYPE: PRT
<213> ORGANISM: Artificial Sequence
<220> FEATURE:
<223> OTHER INFORMATION: C13 Heavy Chain Variable Region

<400> SEQUENCE: 23

Gln Ser Leu Glu Glu Ser Gly Gly Arg Leu Ala Lys Pro Gly Glu Thr
1               5                   10                  15

Leu Thr Leu Thr Cys Thr Val Ser Gly Ile Asp Leu Asn Ser His Ala
            20                  25                  30

Val Asp Trp Val Arg Gln Ala Pro Gly Lys Gly Leu Glu Trp Ile Gly
        35                  40                  45

Val Ile Gly Pro Gly Gly Asn Thr Tyr Tyr Ala Ser Trp Ala Lys Gly
    50                  55                  60
```

```
Arg Phe Thr Ile Ser Lys Thr Ser Ser Thr Thr Val Asp Leu Lys Met
 65                  70                  75                  80

Thr Ser Leu Thr Ala Glu Asp Thr Ala Thr Phe Phe Cys Ala Thr Tyr
                 85                  90                  95

Pro Ile Tyr Ser Gly Asp Asn Ile Trp Gly Pro Gly Thr Leu Val Thr
            100                 105                 110

Val Ser Ser
        115

<210> SEQ ID NO 24
<211> LENGTH: 110
<212> TYPE: PRT
<213> ORGANISM: Artificial Sequence
<220> FEATURE:
<223> OTHER INFORMATION: C13 Light Chain Variable Region

<400> SEQUENCE: 24

Asp Pro Val Leu Thr Gln Thr Pro Pro Ser Val Ser Ala Ala Val Gly
  1               5                  10                  15

Gly Thr Val Thr Ile Asn Cys Gln Ser Ser Glu Ser Val Asp Asn Asn
                 20                  25                  30

Asn Gln Leu Ser Trp Tyr Gln Gln Lys Val Gly Gln Pro Pro Lys Arg
             35                  40                  45

Leu Met Tyr Tyr Ala Ser Thr Leu Asp Ser Gly Val Pro Ser Arg Phe
 50                  55                  60

Lys Gly Gly Gly Ser Gly Thr His Phe Thr Leu Thr Ile Thr Asp Leu
 65                  70                  75                  80

Glu Cys Asp Asp Ala Ala Thr Tyr Tyr Cys Gln Gly Gly Thr Ala Thr
                 85                  90                  95

Asn Ile Tyr Pro Phe Gly Gly Gly Thr Glu Val Val Val Lys
            100                 105                 110

<210> SEQ ID NO 25
<211> LENGTH: 114
<212> TYPE: PRT
<213> ORGANISM: Artificial Sequence
<220> FEATURE:
<223> OTHER INFORMATION: C14 Heavy Chain Variable Region

<400> SEQUENCE: 25

Gln Ser Pro Glu Glu Ser Gly Gly Arg Leu Val Thr Pro Gly Gly Ser
  1               5                  10                  15

Leu Thr Leu Thr Cys Lys Ile Ser Gly Val Asp Leu Ser Asn Tyr Ala
                 20                  25                  30

Met Asp Trp Val Arg Gln Ala Pro Gly Lys Gly Leu Glu Trp Ile Gly
             35                  40                  45

Val Ile Ala Pro Asn Asp Ala Thr Tyr Tyr Pro Thr Trp Ala Arg Gly
 50                  55                  60

Arg Leu Thr Ile Ser Lys Thr Ser Thr Thr Val Asp Leu Lys Met Thr
 65                  70                  75                  80

Arg Leu Thr Thr Glu Asp Thr Ala Thr Tyr Phe Cys Ala Ala Tyr Pro
                 85                  90                  95

Ile Asp Val Gly Ala Asn Val Trp Gly Pro Gly Thr Leu Val Thr Val
            100                 105                 110

Ser Ser

<210> SEQ ID NO 26
<211> LENGTH: 110
```

```
<212> TYPE: PRT
<213> ORGANISM: Artificial Sequence
<220> FEATURE:
<223> OTHER INFORMATION: C14 Light Chain Variable Region

<400> SEQUENCE: 26

Asp Pro Met Leu Thr Gln Thr Ala Ser Pro Val Ser Ala Ala Val Gly
1               5                   10                  15

Gly Thr Val Thr Ile Asn Cys Gln Ser Ser Glu Ser Val Asp Tyr Asn
                20                  25                  30

Asn Gln Leu Ser Trp Tyr Gln Gln Lys Pro Gly Gln Pro Pro Lys Arg
            35                  40                  45

Leu Met Tyr Tyr Val Ser Thr Leu Asp Ser Gly Val Pro Ser Arg Phe
        50                  55                  60

Lys Gly Ser Gly Ser Gly Thr Gln Phe Ser Leu Thr Ile Ser Asp Leu
65                  70                  75                  80

Glu Cys Asp Asp Ala Gly Thr Tyr Tyr Cys Gln Gly Gly Tyr Ile Ser
                85                  90                  95

Asn Leu Tyr Pro Phe Gly Gly Gly Thr Glu Val Val Val Lys
            100                 105                 110

<210> SEQ ID NO 27
<211> LENGTH: 114
<212> TYPE: PRT
<213> ORGANISM: Artificial Sequence
<220> FEATURE:
<223> OTHER INFORMATION: C11 Heavy Chain Variable Region

<400> SEQUENCE: 27

Gln Ser Leu Glu Glu Ser Gly Gly Arg Leu Val Ser Pro Gly Gly Ser
1               5                   10                  15

Leu Thr Leu Thr Cys Thr Val Ser Gly Ile Asp Leu Ser His Ala
                20                  25                  30

Met Asp Trp Val Arg Gln Ala Pro Gly Lys Gly Leu Glu Trp Ile Gly
            35                  40                  45

Val Ile Ala Pro Asn Asp Ala Thr Tyr Tyr Pro Thr Trp Ala Arg Gly
        50                  55                  60

Arg Phe Thr Ile Ser Lys Thr Ser Thr Thr Val Gly Leu Lys Met Thr
65                  70                  75                  80

Arg Leu Thr Thr Glu Asp Thr Ala Thr Tyr Phe Cys Ala Ala Tyr Pro
                85                  90                  95

Ile Asp Ala Gly Ala Asn Val Trp Gly Pro Gly Thr Leu Val Thr Val
            100                 105                 110

Ser Ser

<210> SEQ ID NO 28
<211> LENGTH: 110
<212> TYPE: PRT
<213> ORGANISM: Artificial Sequence
<220> FEATURE:
<223> OTHER INFORMATION: C11 Light Chain Variable Region

<400> SEQUENCE: 28

Asp Pro Met Leu Thr Gln Thr Ala Ser Pro Val Ser Ala His Val Gly
1               5                   10                  15

Gly Thr Val Thr Ile Asn Cys Gln Ser Ser Glu Ser Val Asp Tyr Asn
                20                  25                  30

Asn Gln Leu Ser Trp Tyr Gln Gln Lys Pro Gly Gln Pro Pro Lys Arg
            35                  40                  45
```

```
Leu Met Tyr Tyr Val Ser Thr Leu Asp Ser Gly Val Pro Ser Arg Phe
        50                  55                  60

Lys Gly Ser Gly Ser Gly Thr Gln Phe Ser Leu Thr Ile Ser Asp Leu
 65                  70                  75                  80

Glu Cys Asp Asp Ala Gly Thr Tyr Tyr Cys Gln Gly Gly Tyr Ile Ser
                     85                  90                  95

Asn Leu Tyr Pro Phe Gly Gly Gly Thr Glu Val Val Val Lys
                100                 105                 110

<210> SEQ ID NO 29
<211> LENGTH: 125
<212> TYPE: PRT
<213> ORGANISM: Artificial Sequence
<220> FEATURE:
<223> OTHER INFORMATION: C4 Heavy Chain Variable Region

<400> SEQUENCE: 29

Gln Glu Gln Leu Glu Gln Ser Gly Gly Gly Ala Glu Gly Gly Leu Val
 1               5                  10                  15

Lys Pro Gly Gly Ser Leu Glu Leu Cys Cys Lys Ala Ser Gly Phe Thr
                20                  25                  30

Leu Ser Ser Ser Tyr Trp Ile Cys Trp Val Arg Gln Ala Pro Gly Lys
            35                  40                  45

Gly Leu Glu Trp Ile Gly Cys Ile His Tyr Ser Gly Ser Thr Ala
        50                  55                  60

Tyr Tyr Ala Ser Trp Val Asn Gly Arg Phe Thr Leu Ser Arg Asp Ile
 65                  70                  75                  80

Asp Gln Ser Thr Gly Cys Leu Gln Leu Asn Ser Leu Thr Ala Ala Asp
                85                  90                  95

Thr Ala Met Tyr Tyr Cys Ala Arg Phe Leu Ser Asp Met Tyr Tyr Tyr
                100                 105                 110

Asn Leu Trp Gly Pro Gly Thr Leu Val Thr Val Ser Ser
            115                 120                 125

<210> SEQ ID NO 30
<211> LENGTH: 112
<212> TYPE: PRT
<213> ORGANISM: Artificial Sequence
<220> FEATURE:
<223> OTHER INFORMATION: C4 Light Chain Variable Region

<400> SEQUENCE: 30

Gln Val Leu Thr Gln Thr Pro Ala Ser Val Ser Ala Ala Val Gly Gly
 1               5                  10                  15

Thr Val Thr Ile Asn Cys Gln Ala Ser Gln Ser Ile Tyr Asn Asn Asn
                20                  25                  30

Gln Leu Ser Trp Tyr Gln Gln Lys Pro Gly Gln Pro Pro Lys Leu Leu
            35                  40                  45

Ile Tyr Tyr Ala Ser Thr Leu Ala Ser Gly Val Ser Ser Arg Phe Lys
        50                  55                  60

Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Gln Gly Gln Phe Asn Cys Arg
                85                  90                  95

Ser Ala Asp Cys His Ala Phe Gly Gly Gly Thr Glu Val Val Val Lys
                100                 105                 110
```

```
<210> SEQ ID NO 31
<211> LENGTH: 110
<212> TYPE: PRT
<213> ORGANISM: Artificial Sequence
<220> FEATURE:
<223> OTHER INFORMATION: C5 Heavy Chain Variable Region

<400> SEQUENCE: 31

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Gly Ala Trp
            20                  25                  30

Met Asn Trp Val Arg Gln Ala Pro Gly Lys Gly Leu Glu Trp Ile Gly
        35                  40                  45

Val Val Ser Ser Asp Asp Asn Ile Tyr Tyr Ala Asp Trp Ala Lys Gly
    50                  55                  60

Arg Phe Thr Ile Ser Lys Thr Ser Thr Thr Val Asp Leu Lys Leu Thr
65                  70                  75                  80

Ser Pro Thr Thr Glu Asp Thr Ala Thr Tyr Phe Cys Ala Arg Asn Leu
                85                  90                  95

Gly Thr Ile Trp Gly Pro Gly Thr Leu Val Thr Val Ser Ser
            100                 105                 110

<210> SEQ ID NO 32
<211> LENGTH: 108
<212> TYPE: PRT
<213> ORGANISM: Artificial Sequence
<220> FEATURE:
<223> OTHER INFORMATION: C5 Light Chain Variable Region

<400> SEQUENCE: 32

Gln Val Leu Thr Gln Thr Glu Ser Pro Val Ser Ala Ala Val Gly Gly
1               5                   10                  15

Thr Val Thr Ile Asn Cys Gln Ser Ser Gln Ser Val Trp Ser Asn Tyr
            20                  25                  30

Leu Ser Trp Phe Gln Gln Lys Pro Gly Gln Pro Pro Lys Val Leu Ile
        35                  40                  45

Tyr Gly Thr Ser Lys Leu Pro Ser Gly Val Pro Ser Arg Phe Ser Gly
    50                  55                  60

Ser Gly Ser Gly Thr Glu Phe Thr Leu Thr Ile Asn Asp Leu Glu Cys
65                  70                  75                  80

Asp Asp Ala Ala Thr Tyr Tyr Cys Ala Gly Gly Tyr Ser Gly His Ile
                85                  90                  95

Tyr Ser Phe Gly Gly Gly Thr Glu Val Val Val Lys
            100                 105

<210> SEQ ID NO 33
<211> LENGTH: 121
<212> TYPE: PRT
<213> ORGANISM: Artificial Sequence
<220> FEATURE:
<223> OTHER INFORMATION: C9 Heavy Chain Variable Region

<400> SEQUENCE: 33

Gln Glu Gln Leu Glu Glu Ser Gly Gly Asp Leu Val Lys Pro Glu Gly
1               5                   10                  15

Ser Leu Thr Leu Thr Cys Thr Ala Ser Gly Phe Ser Phe Ser Ser
            20                  25                  30

Tyr Trp Ile Cys Trp Val Arg Gln Ala Pro Gly Lys Gly Leu Glu Trp
        35                  40                  45
```

```
Ile Ala Cys Ile Tyr Gln Ser Gly Asp Gly Arg Thr Trp Tyr Ala Ser
 50                  55                  60
Trp Ala Glu Gly Arg Phe Thr Ile Ser Lys Thr Ser Pro Thr Thr Val
 65                  70                  75                  80
Thr Leu Gln Met Ala Ser Leu Thr Ala Ala Asp Thr Ala Thr Tyr Phe
                 85                  90                  95
Cys Ala Arg Cys Pro His Asn Thr Tyr Ser His Phe Asp Leu Trp Gly
                100                 105                 110
Pro Ser Thr Leu Val Thr Val Ser Ser
                115                 120
```

<210> SEQ ID NO 34
<211> LENGTH: 114
<212> TYPE: PRT
<213> ORGANISM: Artificial Sequence
<220> FEATURE:
<223> OTHER INFORMATION: C9 Light Chain Variable Region

<400> SEQUENCE: 34

```
Ala Asp Ile Val Met Thr Gln Thr Pro Ala Ser Val Glu Ala Ala Val
 1                5                  10                  15
Gly Gly Thr Val Thr Ile Lys Cys Gln Ala Ser Gln Ser Ile Asn Ser
                 20                  25                  30
Trp Leu Ser Trp Tyr Gln Gln Lys Pro Gly Gln Pro Lys Pro Leu
                 35                  40                  45
Ile Tyr Gly Ala Ser Asn Leu Ala Ser Gly Val Pro Ser Arg Phe Lys
 50                  55                  60
Gly Ser Gly Ser Gly Thr Gln Phe Thr Leu Thr Ile Ser Asp Leu Glu
 65                  70                  75                  80
Cys Ala Asp Ala Ala Thr Tyr Ser Cys Leu Gly Tyr Tyr Tyr Ser Ser
                 85                  90                  95
Tyr Asn Ser Val Gly Phe Trp Ala Phe Gly Gly Gly Thr Glu Val Val
                100                 105                 110
Val Lys
```

<210> SEQ ID NO 35
<211> LENGTH: 112
<212> TYPE: PRT
<213> ORGANISM: Artificial Sequence
<220> FEATURE:
<223> OTHER INFORMATION: C26 Heavy Chain Variable Region

<400> SEQUENCE: 35

```
Gln Glu Gln Leu Glu Glu Ser Gly Gly Gly Leu Val Gln Pro Glu Gly
 1                5                  10                  15
Ser Leu Thr Leu Thr Cys Thr Ala Ser Gly Phe Thr Leu Ser Asn Tyr
                 20                  25                  30
Trp Met Ser Trp Val Arg Gln Ala Pro Gly Lys Gly Leu Val Trp Ile
                 35                  40                  45
Gly Cys Ile Asp Ile Gly Ser Asp Asp Thr Tyr Tyr Ala Ser Trp Ala
 50                  55                  60
Lys Gly Arg Phe Thr Ile Ser Arg Thr Ser Thr Thr Val Thr Leu
 65                  70                  75                  80
Gln Val Thr Ser Leu Thr Ala Ala Asp Thr Ala Thr Tyr Phe Cys Ala
                 85                  90                  95
Arg Ser Gly Gly Leu Trp Gly Pro Gly Thr Leu Val Thr Val Ser Ser
                100                 105                 110
```

<210> SEQ ID NO 36
<211> LENGTH: 109
<212> TYPE: PRT
<213> ORGANISM: Artificial Sequence
<220> FEATURE:
<223> OTHER INFORMATION: C26 Light Chain Variable Region

<400> SEQUENCE: 36

```
Gln Val Leu Thr Gln Thr Pro Ser Ser Thr Ser Ala Ala Val Gly Gly
1               5                   10                  15

Thr Val Thr Ile Asn Cys Gln Ala Ser Gln Ser Val Tyr Asn Asn Asn
            20                  25                  30

Asp Leu Ala Trp Tyr Gln Gln Lys Pro Gly Gln Pro Pro Lys Arg Leu
        35                  40                  45

Ile Tyr Glu Ala Ser Lys Leu Ala Ser Gly Val Pro Ser Arg Phe Ser
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Ala Gly Gly Trp Ser Gly Asn
                85                  90                  95

Phe Tyr Val Phe Gly Gly Gly Thr Glu Val Val Val Lys
            100                 105
```

<210> SEQ ID NO 37
<211> LENGTH: 108
<212> TYPE: PRT
<213> ORGANISM: Artificial Sequence
<220> FEATURE:
<223> OTHER INFORMATION: C27 Heavy Chain Variable Region

<400> SEQUENCE: 37

```
Gln Ser Val Glu Glu Ser Gly Gly Arg Leu Val Thr Pro Gly Gly Ser
1               5                   10                  15

Leu Thr Leu Thr Cys Thr Val Ser Gly Ile Asp Leu Ile Asn Ala Trp
            20                  25                  30

Met Asn Trp Val Arg Gln Ala Pro Gly Lys Gly Leu Glu Trp Ile Gly
        35                  40                  45

Thr Thr Thr Asp Asp Asp Thr Ile Tyr Tyr Ala Asn Trp Ala Lys Gly
    50                  55                  60

Arg Phe Thr Ile Ser Arg Thr Ser Thr Thr Val Asp Leu Lys Val Thr
65                  70                  75                  80

Ser Leu Thr Ser Glu Asp Thr Ala Thr Tyr Phe Cys Ser Lys Gly Arg
                85                  90                  95

Ile Trp Gly Pro Gly Thr Leu Val Thr Val Ser Leu
            100                 105
```

<210> SEQ ID NO 38
<211> LENGTH: 109
<212> TYPE: PRT
<213> ORGANISM: Artificial Sequence
<220> FEATURE:
<223> OTHER INFORMATION: C27 Light Chain Variable Region

<400> SEQUENCE: 38

```
Gln Val Leu Thr Gln Thr Pro Ala Ser Val Ser Ala Ala Val Gly Gly
1               5                   10                  15

Thr Val Thr Ile Asn Cys Gln Ala Ser Gln Ser Val Tyr Asp Gly Asn
            20                  25                  30
```

```
Trp Leu Cys Trp Tyr Gln Gln Lys Pro Gly Gln Pro Pro Lys Arg Leu
            35                  40                  45

Ile Tyr Lys Ala Ser Thr Leu Glu Ser Gly Val Pro Ser Arg Phe Lys
 50                  55                  60

Gly Ser Gly Ser Gly Thr Gln Phe Thr Leu Thr Ile Ser Asp Leu Glu
 65                  70                  75                  80

Cys Asp Asp Ala Ala Thr Tyr Tyr Cys Gln Gly Gly Phe Thr Ser Asn
                 85                  90                  95

Ile Tyr Pro Phe Ala Gly Gly Thr Glu Val Val Lys
                100                 105
```

```
<210> SEQ ID NO 39
<211> LENGTH: 109
<212> TYPE: PRT
<213> ORGANISM: Artificial Sequence
<220> FEATURE:
<223> OTHER INFORMATION: C17 Heavy Chain Variable Region

<400> SEQUENCE: 39

Gln Ser Val Glu Glu Ser Gly Gly Arg Leu Val Lys Pro Asp Glu Thr
 1               5                  10                  15

Leu Thr Leu Thr Cys Ala Val Ser Gly Ile Asp Leu Ser Ser Asn Ala
                 20                  25                  30

Met Asn Trp Val Arg Gln Ala Pro Gly Glu Gly Leu Glu Trp Ile Gly
            35                  40                  45

Ser Met Tyr Thr Asp Gly Thr Thr Tyr Tyr Ala Asn Trp Ala Lys Gly
 50                  55                  60

Arg Phe Thr Ile Ser Arg Ala Ser Ser Thr Thr Val Asp Leu Lys Met
 65                  70                  75                  80

Thr Ser Leu Thr Ala Ala Asp Thr Ala Thr Tyr Phe Cys Ala Arg Gly
                 85                  90                  95

Asp Ile Trp Gly Pro Gly Thr Leu Val Thr Val Ser Ser
                100                 105
```

```
<210> SEQ ID NO 40
<211> LENGTH: 109
<212> TYPE: PRT
<213> ORGANISM: Artificial Sequence
<220> FEATURE:
<223> OTHER INFORMATION: C17 Light Chain Variable Region

<400> SEQUENCE: 40

Gln Val Leu Thr Gln Thr Ala Ser Pro Val Ser Ala Ala Val Gly Gly
 1               5                  10                  15

Thr Val Thr Ile Ser Cys Gln Ser Ser Gln Ser Val Tyr Asn Asn Asn
                 20                  25                  30

Trp Leu Ala Trp Phe Gln Gln Lys Pro Gly Gln Pro Pro Lys Arg Leu
            35                  40                  45

Ile Tyr Gly Thr Ser Glu Leu Ala Ser Gly Val Pro Ser Arg Phe Lys
 50                  55                  60

Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Leu Gly Thr Tyr Ser Ser Asn
                 85                  90                  95

Ile His Val Phe Gly Gly Gly Thr Glu Val Val Val Lys
                100                 105
```

```
<210> SEQ ID NO 41
```

```
<211> LENGTH: 5
<212> TYPE: PRT
<213> ORGANISM: Artificial Sequence
<220> FEATURE:
<223> OTHER INFORMATION: C8 HC CDR1

<400> SEQUENCE: 41

Ser Asn Arg Met Ser
1               5

<210> SEQ ID NO 42
<211> LENGTH: 14
<212> TYPE: PRT
<213> ORGANISM: Artificial Sequence
<220> FEATURE:
<223> OTHER INFORMATION: C8 HC CDR2

<400> SEQUENCE: 42

Ser Ile Gly Ser Ser Pro Trp Tyr Ala Ser Trp Ala Gln Gly
1               5                   10

<210> SEQ ID NO 43
<211> LENGTH: 9
<212> TYPE: PRT
<213> ORGANISM: Artificial Sequence
<220> FEATURE:
<223> OTHER INFORMATION: C8 HC CDR3

<400> SEQUENCE: 43

Gly Gly Tyr Arg Pro Gly Ala Ser Val
1               5

<210> SEQ ID NO 44
<211> LENGTH: 5
<212> TYPE: PRT
<213> ORGANISM: Artificial Sequence
<220> FEATURE:
<223> OTHER INFORMATION: C24 HC CDR1

<400> SEQUENCE: 44

Thr Asn Arg Val Ser
1               5

<210> SEQ ID NO 45
<211> LENGTH: 14
<212> TYPE: PRT
<213> ORGANISM: Artificial Sequence
<220> FEATURE:
<223> OTHER INFORMATION: C24 HC CDR2

<400> SEQUENCE: 45

Ser Ile Gly Ser Ser Pro Trp Tyr Ala Ser Trp Ala Gln Gly
1               5                   10

<210> SEQ ID NO 46
<211> LENGTH: 9
<212> TYPE: PRT
<213> ORGANISM: Artificial Sequence
<220> FEATURE:
<223> OTHER INFORMATION: C24 HC CDR3

<400> SEQUENCE: 46

Gly Gly Tyr Arg Pro Gly Gly Ser Ile
1               5

<210> SEQ ID NO 47
<211> LENGTH: 5
```

<212> TYPE: PRT
<213> ORGANISM: Artificial Sequence
<220> FEATURE:
<223> OTHER INFORMATION: C25 HC CDR1

<400> SEQUENCE: 47

Thr Asn Arg Met Ser
1               5

<210> SEQ ID NO 48
<211> LENGTH: 14
<212> TYPE: PRT
<213> ORGANISM: Artificial Sequence
<220> FEATURE:
<223> OTHER INFORMATION: C25 HC CDR2

<400> SEQUENCE: 48

Ser Ile Gly Ser Ser Pro Trp Phe Ala Ser Trp Ala Leu Gly
1               5                   10

<210> SEQ ID NO 49
<211> LENGTH: 9
<212> TYPE: PRT
<213> ORGANISM: Artificial Sequence
<220> FEATURE:
<223> OTHER INFORMATION: C25 HC CDR3

<400> SEQUENCE: 49

Gly Gly Tyr Arg Pro Gly Ala Ser Val
1               5

<210> SEQ ID NO 50
<211> LENGTH: 5
<212> TYPE: PRT
<213> ORGANISM: Artificial Sequence
<220> FEATURE:
<223> OTHER INFORMATION: C7 HC CDR1

<400> SEQUENCE: 50

Ser His Ala Met Asp
1               5

<210> SEQ ID NO 51
<211> LENGTH: 16
<212> TYPE: PRT
<213> ORGANISM: Artificial Sequence
<220> FEATURE:
<223> OTHER INFORMATION: C7 HC CDR2

<400> SEQUENCE: 51

Val Ile Ala Pro Asp Thr Arg Thr Tyr Tyr Ala Thr Trp Ala Arg Gly
1               5                   10                  15

<210> SEQ ID NO 52
<211> LENGTH: 9
<212> TYPE: PRT
<213> ORGANISM: Artificial Sequence
<220> FEATURE:
<223> OTHER INFORMATION: C7 HC CDR3

<400> SEQUENCE: 52

Tyr Pro Ile Glu Pro Gly Ala Asn Ile
1               5

<210> SEQ ID NO 53
<211> LENGTH: 5
<212> TYPE: PRT

```
<213> ORGANISM: Artificial Sequence
<220> FEATURE:
<223> OTHER INFORMATION: C6 HC CDR1

<400> SEQUENCE: 53

Asn Tyr Ala Met Asp
1               5

<210> SEQ ID NO 54
<211> LENGTH: 16
<212> TYPE: PRT
<213> ORGANISM: Artificial Sequence
<220> FEATURE:
<223> OTHER INFORMATION: C6 HC CDR2

<400> SEQUENCE: 54

Val Ile Ala Pro Asn Arg Arg Thr Tyr Tyr Pro Thr Trp Ala Arg Gly
1               5                   10                  15

<210> SEQ ID NO 55
<211> LENGTH: 9
<212> TYPE: PRT
<213> ORGANISM: Artificial Sequence
<220> FEATURE:
<223> OTHER INFORMATION: C6 HC CDR3

<400> SEQUENCE: 55

Tyr Pro Ile Glu Pro Gly Ala Asn Ile
1               5

<210> SEQ ID NO 56
<211> LENGTH: 5
<212> TYPE: PRT
<213> ORGANISM: Artificial Sequence
<220> FEATURE:
<223> OTHER INFORMATION: C1 HC CDR1

<400> SEQUENCE: 56

Ser Tyr Ala Met Asp
1               5

<210> SEQ ID NO 57
<211> LENGTH: 16
<212> TYPE: PRT
<213> ORGANISM: Artificial Sequence
<220> FEATURE:
<223> OTHER INFORMATION: C1 HC CDR2

<400> SEQUENCE: 57

Val Ile Ala Pro Asn Gly Ala Thr Tyr Tyr Pro Thr Trp Ala Arg Gly
1               5                   10                  15

<210> SEQ ID NO 58
<211> LENGTH: 9
<212> TYPE: PRT
<213> ORGANISM: Artificial Sequence
<220> FEATURE:
<223> OTHER INFORMATION: C1 HC CDR3

<400> SEQUENCE: 58

Tyr Pro Ile Asp Ala Gly Ala Asn Ile
1               5

<210> SEQ ID NO 59
<211> LENGTH: 5
<212> TYPE: PRT
<213> ORGANISM: Artificial Sequence
```

```
<220> FEATURE:
<223> OTHER INFORMATION: C16 HC CDR1

<400> SEQUENCE: 59

Ser Tyr Ala Met Asp
1               5

<210> SEQ ID NO 60
<211> LENGTH: 16
<212> TYPE: PRT
<213> ORGANISM: Artificial Sequence
<220> FEATURE:
<223> OTHER INFORMATION: C16 HC CDR2

<400> SEQUENCE: 60

Val Ile Ala Pro Asn His Tyr Thr Tyr Tyr Pro Thr Trp Ala Arg Gly
1               5                   10                  15

<210> SEQ ID NO 61
<211> LENGTH: 9
<212> TYPE: PRT
<213> ORGANISM: Artificial Sequence
<220> FEATURE:
<223> OTHER INFORMATION: C16 HC CDR3

<400> SEQUENCE: 61

Tyr Pro Ile Glu Ser Gly Ser Asn Ile
1               5

<210> SEQ ID NO 62
<211> LENGTH: 5
<212> TYPE: PRT
<213> ORGANISM: Artificial Sequence
<220> FEATURE:
<223> OTHER INFORMATION: C20 HC CDR1

<400> SEQUENCE: 62

Asn Tyr Ala Ile Asp
1               5

<210> SEQ ID NO 63
<211> LENGTH: 16
<212> TYPE: PRT
<213> ORGANISM: Artificial Sequence
<220> FEATURE:
<223> OTHER INFORMATION: C20 HC CDR2

<400> SEQUENCE: 63

Val Ile Ala Pro Asn His Tyr Thr Cys Tyr Pro Thr Trp Ala Arg Gly
1               5                   10                  15

<210> SEQ ID NO 64
<211> LENGTH: 9
<212> TYPE: PRT
<213> ORGANISM: Artificial Sequence
<220> FEATURE:
<223> OTHER INFORMATION: C20 HC CDR3

<400> SEQUENCE: 64

Tyr Pro Ile Glu Thr Gly Ser Asn Ile
1               5

<210> SEQ ID NO 65
<211> LENGTH: 5
<212> TYPE: PRT
<213> ORGANISM: Artificial Sequence
<220> FEATURE:
```

<223> OTHER INFORMATION: C22 HC CDR1

<400> SEQUENCE: 65

Asn Tyr Ala Met Asp
1               5

<210> SEQ ID NO 66
<211> LENGTH: 16
<212> TYPE: PRT
<213> ORGANISM: Artificial Sequence
<220> FEATURE:
<223> OTHER INFORMATION: C22 HC CDR2

<400> SEQUENCE: 66

Val Ile Ala Pro Asn His Tyr Thr Tyr Tyr Pro Thr Trp Ala Arg Gly
1               5                   10                  15

<210> SEQ ID NO 67
<211> LENGTH: 9
<212> TYPE: PRT
<213> ORGANISM: Artificial Sequence
<220> FEATURE:
<223> OTHER INFORMATION: C22 HC CDR3

<400> SEQUENCE: 67

Tyr Pro Ile Glu Thr Gly Ser Asn Ile
1               5

<210> SEQ ID NO 68
<211> LENGTH: 5
<212> TYPE: PRT
<213> ORGANISM: Artificial Sequence
<220> FEATURE:
<223> OTHER INFORMATION: C10 HC CDR1

<400> SEQUENCE: 68

Ser Tyr Ala Ile Asp
1               5

<210> SEQ ID NO 69
<211> LENGTH: 16
<212> TYPE: PRT
<213> ORGANISM: Artificial Sequence
<220> FEATURE:
<223> OTHER INFORMATION: C10 HC CDR2

<400> SEQUENCE: 69

Val Ile Ala Pro Ser Gly Thr Thr Tyr Tyr Pro Thr Trp Ala Lys Gly
1               5                   10                  15

<210> SEQ ID NO 70
<211> LENGTH: 9
<212> TYPE: PRT
<213> ORGANISM: Artificial Sequence
<220> FEATURE:
<223> OTHER INFORMATION: C10 HC CDR3

<400> SEQUENCE: 70

Tyr Pro Ile Asp Pro Gly Ser Asn Ile
1               5

<210> SEQ ID NO 71
<211> LENGTH: 5
<212> TYPE: PRT
<213> ORGANISM: Artificial Sequence
<220> FEATURE:
<223> OTHER INFORMATION: C12 HC CDR1

```
<400> SEQUENCE: 71

Ser Tyr Ala Ile Asp
1               5

<210> SEQ ID NO 72
<211> LENGTH: 16
<212> TYPE: PRT
<213> ORGANISM: Artificial Sequence
<220> FEATURE:
<223> OTHER INFORMATION: C12 HC CDR2

<400> SEQUENCE: 72

Val Ile Ala Pro Ser Ser Thr Thr Tyr Tyr Pro Thr Trp Ala Lys Gly
1               5                   10                  15

<210> SEQ ID NO 73
<211> LENGTH: 9
<212> TYPE: PRT
<213> ORGANISM: Artificial Sequence
<220> FEATURE:
<223> OTHER INFORMATION: C12 HC CDR3

<400> SEQUENCE: 73

Tyr Pro Ile Asp Pro Gly Ser Asn Val
1               5

<210> SEQ ID NO 74
<211> LENGTH: 5
<212> TYPE: PRT
<213> ORGANISM: Artificial Sequence
<220> FEATURE:
<223> OTHER INFORMATION: C13 HC CDR1

<400> SEQUENCE: 74

Ser His Ala Val Asp
1               5

<210> SEQ ID NO 75
<211> LENGTH: 16
<212> TYPE: PRT
<213> ORGANISM: Artificial Sequence
<220> FEATURE:
<223> OTHER INFORMATION: C13 HC CDR2

<400> SEQUENCE: 75

Val Ile Gly Pro Gly Gly Asn Thr Tyr Tyr Ala Ser Trp Ala Lys Gly
1               5                   10                  15

<210> SEQ ID NO 76
<211> LENGTH: 9
<212> TYPE: PRT
<213> ORGANISM: Artificial Sequence
<220> FEATURE:
<223> OTHER INFORMATION: C13 HC CDR3

<400> SEQUENCE: 76

Tyr Pro Ile Tyr Ser Gly Asp Asn Ile
1               5

<210> SEQ ID NO 77
<211> LENGTH: 5
<212> TYPE: PRT
<213> ORGANISM: Artificial Sequence
<220> FEATURE:
<223> OTHER INFORMATION: C14 HC CDR1
```

```
<400> SEQUENCE: 77

Asn Tyr Ala Met Asp
1               5

<210> SEQ ID NO 78
<211> LENGTH: 16
<212> TYPE: PRT
<213> ORGANISM: Artificial Sequence
<220> FEATURE:
<223> OTHER INFORMATION: C14 HC CDR2

<400> SEQUENCE: 78

Val Ile Ala Pro Asn Asp Ala Thr Tyr Tyr Pro Thr Trp Ala Arg Gly
1               5                   10                  15

<210> SEQ ID NO 79
<211> LENGTH: 9
<212> TYPE: PRT
<213> ORGANISM: Artificial Sequence
<220> FEATURE:
<223> OTHER INFORMATION: C14 HC CDR3

<400> SEQUENCE: 79

Tyr Pro Ile Asp Val Gly Ala Asn Val
1               5

<210> SEQ ID NO 80
<211> LENGTH: 5
<212> TYPE: PRT
<213> ORGANISM: Artificial Sequence
<220> FEATURE:
<223> OTHER INFORMATION: C11 HC CDR1

<400> SEQUENCE: 80

Ser His Ala Met Asp
1               5

<210> SEQ ID NO 81
<211> LENGTH: 16
<212> TYPE: PRT
<213> ORGANISM: Artificial Sequence
<220> FEATURE:
<223> OTHER INFORMATION: C11 HC CDR2

<400> SEQUENCE: 81

Val Ile Ala Pro Asn Asp Ala Thr Tyr Tyr Pro Thr Trp Ala Arg Gly
1               5                   10                  15

<210> SEQ ID NO 82
<211> LENGTH: 9
<212> TYPE: PRT
<213> ORGANISM: Artificial Sequence
<220> FEATURE:
<223> OTHER INFORMATION: C11 HC CDR3

<400> SEQUENCE: 82

Tyr Pro Ile Asp Ala Gly Ala Asn Val
1               5

<210> SEQ ID NO 83
<211> LENGTH: 6
<212> TYPE: PRT
<213> ORGANISM: Artificial Sequence
<220> FEATURE:
<223> OTHER INFORMATION: C4 HC CDR1

<400> SEQUENCE: 83
```

```
Ser Ser Tyr Trp Ile Cys
1               5

<210> SEQ ID NO 84
<211> LENGTH: 18
<212> TYPE: PRT
<213> ORGANISM: Artificial Sequence
<220> FEATURE:
<223> OTHER INFORMATION: C4 HC CDR2

<400> SEQUENCE: 84

Cys Ile His Tyr Gly Ser Ser Gly Thr Ala Tyr Tyr Ala Ser Trp Val
1               5                   10                  15

Asn Gly

<210> SEQ ID NO 85
<211> LENGTH: 10
<212> TYPE: PRT
<213> ORGANISM: Artificial Sequence
<220> FEATURE:
<223> OTHER INFORMATION: C4 HC CDR3

<400> SEQUENCE: 85

Phe Leu Ser Asp Met Tyr Tyr Tyr Asn Leu
1               5                   10

<210> SEQ ID NO 86
<211> LENGTH: 5
<212> TYPE: PRT
<213> ORGANISM: Artificial Sequence
<220> FEATURE:
<223> OTHER INFORMATION: C5 HC CDR1

<400> SEQUENCE: 86

Gly Ala Trp Met Asn
1               5

<210> SEQ ID NO 87
<211> LENGTH: 16
<212> TYPE: PRT
<213> ORGANISM: Artificial Sequence
<220> FEATURE:
<223> OTHER INFORMATION: C5 HC CDR2

<400> SEQUENCE: 87

Val Val Ser Ser Asp Asp Asn Ile Tyr Tyr Ala Asp Trp Ala Lys Gly
1               5                   10                  15

<210> SEQ ID NO 88
<211> LENGTH: 5
<212> TYPE: PRT
<213> ORGANISM: Artificial Sequence
<220> FEATURE:
<223> OTHER INFORMATION: C5 HC CDR3

<400> SEQUENCE: 88

Asn Leu Gly Thr Ile
1               5

<210> SEQ ID NO 89
<211> LENGTH: 6
<212> TYPE: PRT
<213> ORGANISM: Artificial Sequence
<220> FEATURE:
<223> OTHER INFORMATION: C9 HC CDR1
```

```
<400> SEQUENCE: 89

Ser Ser Tyr Trp Ile Cys
1               5

<210> SEQ ID NO 90
<211> LENGTH: 18
<212> TYPE: PRT
<213> ORGANISM: Artificial Sequence
<220> FEATURE:
<223> OTHER INFORMATION: C9 HC CDR2

<400> SEQUENCE: 90

Cys Ile Tyr Gln Ser Gly Asp Gly Arg Thr Trp Tyr Ala Ser Trp Ala
1               5                   10                  15

Glu Gly

<210> SEQ ID NO 91
<211> LENGTH: 11
<212> TYPE: PRT
<213> ORGANISM: Artificial Sequence
<220> FEATURE:
<223> OTHER INFORMATION: C9 HC CDR3

<400> SEQUENCE: 91

Cys Pro His Asn Thr Tyr Ser His Phe Asp Leu
1               5                   10

<210> SEQ ID NO 92
<211> LENGTH: 5
<212> TYPE: PRT
<213> ORGANISM: Artificial Sequence
<220> FEATURE:
<223> OTHER INFORMATION: C26 HC CDR1

<400> SEQUENCE: 92

Asn Tyr Trp Met Ser
1               5

<210> SEQ ID NO 93
<211> LENGTH: 17
<212> TYPE: PRT
<213> ORGANISM: Artificial Sequence
<220> FEATURE:
<223> OTHER INFORMATION: C26 HC CDR2

<400> SEQUENCE: 93

Cys Ile Asp Ile Gly Ser Asp Asp Thr Tyr Tyr Ala Ser Trp Ala Lys
1               5                   10                  15

Gly

<210> SEQ ID NO 94
<211> LENGTH: 4
<212> TYPE: PRT
<213> ORGANISM: Artificial Sequence
<220> FEATURE:
<223> OTHER INFORMATION: C26 HC CDR3

<400> SEQUENCE: 94

Ser Gly Gly Leu
1

<210> SEQ ID NO 95
<211> LENGTH: 5
<212> TYPE: PRT
<213> ORGANISM: Artificial Sequence
```

```
<220> FEATURE:
<223> OTHER INFORMATION: C27 HC CDR1

<400> SEQUENCE: 95

Asn Ala Trp Met Asn
1               5

<210> SEQ ID NO 96
<211> LENGTH: 16
<212> TYPE: PRT
<213> ORGANISM: Artificial Sequence
<220> FEATURE:
<223> OTHER INFORMATION: C27 HC CDR2

<400> SEQUENCE: 96

Thr Thr Thr Asp Asp Thr Ile Tyr Tyr Ala Asn Trp Ala Lys Gly
1               5                   10                  15

<210> SEQ ID NO 97
<211> LENGTH: 3
<212> TYPE: PRT
<213> ORGANISM: Artificial Sequence
<220> FEATURE:
<223> OTHER INFORMATION: C27 HC CDR3

<400> SEQUENCE: 97

Gly Arg Ile
1

<210> SEQ ID NO 98
<211> LENGTH: 5
<212> TYPE: PRT
<213> ORGANISM: Artificial Sequence
<220> FEATURE:
<223> OTHER INFORMATION: C17 HC CDR1

<400> SEQUENCE: 98

Ser Asn Ala Met Asn
1               5

<210> SEQ ID NO 99
<211> LENGTH: 16
<212> TYPE: PRT
<213> ORGANISM: Artificial Sequence
<220> FEATURE:
<223> OTHER INFORMATION: C17 HC CDR2

<400> SEQUENCE: 99

Ser Met Tyr Thr Asp Gly Thr Thr Tyr Tyr Ala Asn Trp Ala Lys Gly
1               5                   10                  15

<210> SEQ ID NO 100
<211> LENGTH: 3
<212> TYPE: PRT
<213> ORGANISM: Artificial Sequence
<220> FEATURE:
<223> OTHER INFORMATION: C17 HC CDR3

<400> SEQUENCE: 100

Gly Asp Ile
1

<210> SEQ ID NO 101
<211> LENGTH: 13
<212> TYPE: PRT
<213> ORGANISM: Artificial Sequence
<220> FEATURE:
```

<223> OTHER INFORMATION: C8 LC CDR1

<400> SEQUENCE: 101

Gln Ser Ser Gln Ser Val Tyr Asp Asn Asn Asp Leu Ala
1               5                   10

<210> SEQ ID NO 102
<211> LENGTH: 7
<212> TYPE: PRT
<213> ORGANISM: Artificial Sequence
<220> FEATURE:
<223> OTHER INFORMATION: C8 LC CDR2

<400> SEQUENCE: 102

Leu Ala Ser Ser Leu Asp Ser
1               5

<210> SEQ ID NO 103
<211> LENGTH: 10
<212> TYPE: PRT
<213> ORGANISM: Artificial Sequence
<220> FEATURE:
<223> OTHER INFORMATION: C8 LC CDR3

<400> SEQUENCE: 103

Ala Gly Gly Tyr Ser Gly Asp Ile Tyr Thr
1               5                   10

<210> SEQ ID NO 104
<211> LENGTH: 13
<212> TYPE: PRT
<213> ORGANISM: Artificial Sequence
<220> FEATURE:
<223> OTHER INFORMATION: C24 LC CDR1

<400> SEQUENCE: 104

Gln Ser Ser Gln Ser Val Tyr Asp Asn Asn Asp Leu Gly
1               5                   10

<210> SEQ ID NO 105
<211> LENGTH: 7
<212> TYPE: PRT
<213> ORGANISM: Artificial Sequence
<220> FEATURE:
<223> OTHER INFORMATION: C24 LC CDR2

<400> SEQUENCE: 105

Leu Ala Ser Ser Leu Asp Ser
1               5

<210> SEQ ID NO 106
<211> LENGTH: 10
<212> TYPE: PRT
<213> ORGANISM: Artificial Sequence
<220> FEATURE:
<223> OTHER INFORMATION: C24 LC CDR3

<400> SEQUENCE: 106

Ala Gly Gly Tyr Ser Gly Asp Ile Tyr Thr
1               5                   10

<210> SEQ ID NO 107
<211> LENGTH: 13
<212> TYPE: PRT
<213> ORGANISM: Artificial Sequence
<220> FEATURE:
<223> OTHER INFORMATION: C25 LC CDR1

```
<400> SEQUENCE: 107

Gln Ser Ser Gln Ser Val Tyr Asp Asn Asn Asp Leu Ala
1               5                   10

<210> SEQ ID NO 108
<211> LENGTH: 7
<212> TYPE: PRT
<213> ORGANISM: Artificial Sequence
<220> FEATURE:
<223> OTHER INFORMATION: C25 LC CDR2

<400> SEQUENCE: 108

Leu Ala Ser Ser Leu Asp Ser
1               5

<210> SEQ ID NO 109
<211> LENGTH: 10
<212> TYPE: PRT
<213> ORGANISM: Artificial Sequence
<220> FEATURE:
<223> OTHER INFORMATION: C25 LC CDR3

<400> SEQUENCE: 109

Ala Gly Gly Tyr Asn Gly Asp Ile Tyr Thr
1               5                   10

<210> SEQ ID NO 110
<211> LENGTH: 13
<212> TYPE: PRT
<213> ORGANISM: Artificial Sequence
<220> FEATURE:
<223> OTHER INFORMATION: C7 LC CDR1

<400> SEQUENCE: 110

Gln Ala Ser Glu Ser Val Asp Tyr Asn Asn Gln Leu Ser
1               5                   10

<210> SEQ ID NO 111
<211> LENGTH: 7
<212> TYPE: PRT
<213> ORGANISM: Artificial Sequence
<220> FEATURE:
<223> OTHER INFORMATION: C7 LC CDR2

<400> SEQUENCE: 111

Tyr Val Ser Thr Leu Asp Ser
1               5

<210> SEQ ID NO 112
<211> LENGTH: 10
<212> TYPE: PRT
<213> ORGANISM: Artificial Sequence
<220> FEATURE:
<223> OTHER INFORMATION: C7 LC CDR3

<400> SEQUENCE: 112

Gln Gly Gly Tyr Pro Tyr Asn Ile Tyr Pro
1               5                   10

<210> SEQ ID NO 113
<211> LENGTH: 13
<212> TYPE: PRT
<213> ORGANISM: Artificial Sequence
<220> FEATURE:
<223> OTHER INFORMATION: C6 LC CDR1
```

```
<400> SEQUENCE: 113

Gln Ser Ser Glu Ser Val Asp Tyr Asn Asn Gln Leu Ser
1               5                   10

<210> SEQ ID NO 114
<211> LENGTH: 7
<212> TYPE: PRT
<213> ORGANISM: Artificial Sequence
<220> FEATURE:
<223> OTHER INFORMATION: C6 LC CDR2

<400> SEQUENCE: 114

Tyr Val Ser Thr Leu Asp Ser
1               5

<210> SEQ ID NO 115
<211> LENGTH: 10
<212> TYPE: PRT
<213> ORGANISM: Artificial Sequence
<220> FEATURE:
<223> OTHER INFORMATION: C6 LC CDR3

<400> SEQUENCE: 115

Gln Gly Gly Tyr Ile Ser Asn Ile Tyr Pro
1               5                   10

<210> SEQ ID NO 116
<211> LENGTH: 13
<212> TYPE: PRT
<213> ORGANISM: Artificial Sequence
<220> FEATURE:
<223> OTHER INFORMATION: C1 LC CDR1

<400> SEQUENCE: 116

Gln Ser Ser Glu Ser Val Asp Asn Asn Asn Gln Leu Ser
1               5                   10

<210> SEQ ID NO 117
<211> LENGTH: 7
<212> TYPE: PRT
<213> ORGANISM: Artificial Sequence
<220> FEATURE:
<223> OTHER INFORMATION: C1 LC CDR2

<400> SEQUENCE: 117

Tyr Val Ser Thr Leu Asp Ser
1               5

<210> SEQ ID NO 118
<211> LENGTH: 10
<212> TYPE: PRT
<213> ORGANISM: Artificial Sequence
<220> FEATURE:
<223> OTHER INFORMATION: C1 LC CDR3

<400> SEQUENCE: 118

Gln Gly Gly Tyr Ile Ser Asn Leu Tyr Pro
1               5                   10

<210> SEQ ID NO 119
<211> LENGTH: 13
<212> TYPE: PRT
<213> ORGANISM: Artificial Sequence
<220> FEATURE:
<223> OTHER INFORMATION: C16 LC CDR1

<400> SEQUENCE: 119
```

Gln Ser Ser Glu Ser Val Gly Met Asn Asn Gln Leu Ser
1               5                   10

<210> SEQ ID NO 120
<211> LENGTH: 7
<212> TYPE: PRT
<213> ORGANISM: Artificial Sequence
<220> FEATURE:
<223> OTHER INFORMATION: C16 LC CDR2

<400> SEQUENCE: 120

Tyr Val Ser Thr Leu Asp Ser
1               5

<210> SEQ ID NO 121
<211> LENGTH: 10
<212> TYPE: PRT
<213> ORGANISM: Artificial Sequence
<220> FEATURE:
<223> OTHER INFORMATION: C16 LC CDR3

<400> SEQUENCE: 121

Gln Gly Gly Tyr Ile Ser Asn Leu Tyr Pro
1               5                   10

<210> SEQ ID NO 122
<211> LENGTH: 13
<212> TYPE: PRT
<213> ORGANISM: Artificial Sequence
<220> FEATURE:
<223> OTHER INFORMATION: C20 LC CDR1

<400> SEQUENCE: 122

Gln Ser Ser Glu Ser Val Asp Met Asn Asn Gln Leu Ser
1               5                   10

<210> SEQ ID NO 123
<211> LENGTH: 7
<212> TYPE: PRT
<213> ORGANISM: Artificial Sequence
<220> FEATURE:
<223> OTHER INFORMATION: C20 LC CDR2

<400> SEQUENCE: 123

Tyr Val Ser Thr Leu Asp Ser
1               5

<210> SEQ ID NO 124
<211> LENGTH: 10
<212> TYPE: PRT
<213> ORGANISM: Artificial Sequence
<220> FEATURE:
<223> OTHER INFORMATION: C20 LC CDR3

<400> SEQUENCE: 124

Gln Gly Gly Tyr Ile Ser Asn Leu Tyr Pro
1               5                   10

<210> SEQ ID NO 125
<211> LENGTH: 13
<212> TYPE: PRT
<213> ORGANISM: Artificial Sequence
<220> FEATURE:
<223> OTHER INFORMATION: C22 LC CDR1

<400> SEQUENCE: 125

Gln Ser Ser Glu Ser Val Asp Met Asn Asn Gln Leu Ser
1               5                   10

<210> SEQ ID NO 126
<211> LENGTH: 7
<212> TYPE: PRT
<213> ORGANISM: Artificial Sequence
<220> FEATURE:
<223> OTHER INFORMATION: C22 LC CDR2

<400> SEQUENCE: 126

Tyr Val Ser Thr Leu Asp Ser
1               5

<210> SEQ ID NO 127
<211> LENGTH: 10
<212> TYPE: PRT
<213> ORGANISM: Artificial Sequence
<220> FEATURE:
<223> OTHER INFORMATION: C22 LC CDR3

<400> SEQUENCE: 127

Gln Gly Gly Tyr Ile Ser Asn Leu Tyr Pro
1               5                   10

<210> SEQ ID NO 128
<211> LENGTH: 13
<212> TYPE: PRT
<213> ORGANISM: Artificial Sequence
<220> FEATURE:
<223> OTHER INFORMATION: C10 LC CDR1

<400> SEQUENCE: 128

Gln Ser Ser Glu Ser Val Asp Tyr Gly Asn Gln Leu Ser
1               5                   10

<210> SEQ ID NO 129
<211> LENGTH: 7
<212> TYPE: PRT
<213> ORGANISM: Artificial Sequence
<220> FEATURE:
<223> OTHER INFORMATION: C10 LC CDR2

<400> SEQUENCE: 129

Tyr Val Ser Ile Leu Asp Ala
1               5

<210> SEQ ID NO 130
<211> LENGTH: 10
<212> TYPE: PRT
<213> ORGANISM: Artificial Sequence
<220> FEATURE:
<223> OTHER INFORMATION: C10 LC CDR3

<400> SEQUENCE: 130

Gln Gly Gly Tyr Ile Ser Asn Leu Tyr Pro
1               5                   10

<210> SEQ ID NO 131
<211> LENGTH: 13
<212> TYPE: PRT
<213> ORGANISM: Artificial Sequence
<220> FEATURE:
<223> OTHER INFORMATION: C12 LC CDR1

<400> SEQUENCE: 131

Gln Ser Ser Glu Ser Val Asp Tyr Gly Asn Gln Leu Ser

```
1               5                  10

<210> SEQ ID NO 132
<211> LENGTH: 7
<212> TYPE: PRT
<213> ORGANISM: Artificial Sequence
<220> FEATURE:
<223> OTHER INFORMATION: C12 LC CDR2

<400> SEQUENCE: 132

Tyr Val Ser Ile Leu Asp Ala
1               5

<210> SEQ ID NO 133
<211> LENGTH: 10
<212> TYPE: PRT
<213> ORGANISM: Artificial Sequence
<220> FEATURE:
<223> OTHER INFORMATION: C12 LC CDR3

<400> SEQUENCE: 133

Gln Gly Gly Tyr Ile Ser Asn Leu Tyr Pro
1               5                  10

<210> SEQ ID NO 134
<211> LENGTH: 13
<212> TYPE: PRT
<213> ORGANISM: Artificial Sequence
<220> FEATURE:
<223> OTHER INFORMATION: C13 LC CDR1

<400> SEQUENCE: 134

Gln Ser Ser Glu Ser Val Asp Asn Asn Asn Gln Leu Ser
1               5                  10

<210> SEQ ID NO 135
<211> LENGTH: 7
<212> TYPE: PRT
<213> ORGANISM: Artificial Sequence
<220> FEATURE:
<223> OTHER INFORMATION: C13 LC CDR2

<400> SEQUENCE: 135

Tyr Ala Ser Thr Leu Asp Ser
1               5

<210> SEQ ID NO 136
<211> LENGTH: 10
<212> TYPE: PRT
<213> ORGANISM: Artificial Sequence
<220> FEATURE:
<223> OTHER INFORMATION: C13 LC CDR3

<400> SEQUENCE: 136

Gln Gly Gly Thr Ala Thr Asn Ile Tyr Pro
1               5                  10

<210> SEQ ID NO 137
<211> LENGTH: 13
<212> TYPE: PRT
<213> ORGANISM: Artificial Sequence
<220> FEATURE:
<223> OTHER INFORMATION: C14 LC CDR1

<400> SEQUENCE: 137

Gln Ser Ser Glu Ser Val Asp Tyr Asn Asn Gln Leu Ser
1               5                  10
```

```
<210> SEQ ID NO 138
<211> LENGTH: 7
<212> TYPE: PRT
<213> ORGANISM: Artificial Sequence
<220> FEATURE:
<223> OTHER INFORMATION: C14 LC CDR2

<400> SEQUENCE: 138

Tyr Val Ser Thr Leu Asp Ser
1               5

<210> SEQ ID NO 139
<211> LENGTH: 10
<212> TYPE: PRT
<213> ORGANISM: Artificial Sequence
<220> FEATURE:
<223> OTHER INFORMATION: C14 LC CDR3

<400> SEQUENCE: 139

Gln Gly Gly Tyr Ile Ser Asn Leu Tyr Pro
1               5                   10

<210> SEQ ID NO 140
<211> LENGTH: 13
<212> TYPE: PRT
<213> ORGANISM: Artificial Sequence
<220> FEATURE:
<223> OTHER INFORMATION: C11 LC CDR1

<400> SEQUENCE: 140

Gln Ser Ser Glu Ser Val Asp Tyr Asn Asn Gln Leu Ser
1               5                   10

<210> SEQ ID NO 141
<211> LENGTH: 7
<212> TYPE: PRT
<213> ORGANISM: Artificial Sequence
<220> FEATURE:
<223> OTHER INFORMATION: C11 LC CDR2

<400> SEQUENCE: 141

Tyr Val Ser Thr Leu Asp Ser
1               5

<210> SEQ ID NO 142
<211> LENGTH: 10
<212> TYPE: PRT
<213> ORGANISM: Artificial Sequence
<220> FEATURE:
<223> OTHER INFORMATION: C11 LC CDR3

<400> SEQUENCE: 142

Gln Gly Gly Tyr Ile Ser Asn Leu Tyr Pro
1               5                   10

<210> SEQ ID NO 143
<211> LENGTH: 13
<212> TYPE: PRT
<213> ORGANISM: Artificial Sequence
<220> FEATURE:
<223> OTHER INFORMATION: C4 LC CDR1

<400> SEQUENCE: 143

Gln Ala Ser Gln Ser Ile Tyr Asn Asn Asn Gln Leu Ser
1               5                   10
```

```
<210> SEQ ID NO 144
<211> LENGTH: 7
<212> TYPE: PRT
<213> ORGANISM: Artificial Sequence
<220> FEATURE:
<223> OTHER INFORMATION: C4 LC CDR2

<400> SEQUENCE: 144

Tyr Ala Ser Thr Leu Ala Ser
1               5

<210> SEQ ID NO 145
<211> LENGTH: 13
<212> TYPE: PRT
<213> ORGANISM: Artificial Sequence
<220> FEATURE:
<223> OTHER INFORMATION: C4 LC CDR3

<400> SEQUENCE: 145

Gln Gly Gln Phe Asn Cys Arg Ser Ala Asp Cys His Ala
1               5                   10

<210> SEQ ID NO 146
<211> LENGTH: 12
<212> TYPE: PRT
<213> ORGANISM: Artificial Sequence
<220> FEATURE:
<223> OTHER INFORMATION: C5 LC CDR1

<400> SEQUENCE: 146

Gln Ser Ser Gln Ser Val Trp Ser Asn Tyr Leu Ser
1               5                   10

<210> SEQ ID NO 147
<211> LENGTH: 7
<212> TYPE: PRT
<213> ORGANISM: Artificial Sequence
<220> FEATURE:
<223> OTHER INFORMATION: C5 LC CDR2

<400> SEQUENCE: 147

Gly Thr Ser Lys Leu Pro Ser
1               5

<210> SEQ ID NO 148
<211> LENGTH: 10
<212> TYPE: PRT
<213> ORGANISM: Artificial Sequence
<220> FEATURE:
<223> OTHER INFORMATION: C5 LC CDR3

<400> SEQUENCE: 148

Ala Gly Gly Tyr Ser Gly His Ile Tyr Ser
1               5                   10

<210> SEQ ID NO 149
<211> LENGTH: 11
<212> TYPE: PRT
<213> ORGANISM: Artificial Sequence
<220> FEATURE:
<223> OTHER INFORMATION: C9 LC CDR1

<400> SEQUENCE: 149

Gln Ala Ser Gln Ser Ile Asn Ser Trp Leu Ser
1               5                   10
```

```
<210> SEQ ID NO 150
<211> LENGTH: 7
<212> TYPE: PRT
<213> ORGANISM: Artificial Sequence
<220> FEATURE:
<223> OTHER INFORMATION: C9 LC CDR2

<400> SEQUENCE: 150

Gly Ala Ser Asn Leu Ala Ser
1               5

<210> SEQ ID NO 151
<211> LENGTH: 15
<212> TYPE: PRT
<213> ORGANISM: Artificial Sequence
<220> FEATURE:
<223> OTHER INFORMATION: C9 LC CDR3

<400> SEQUENCE: 151

Leu Gly Tyr Tyr Tyr Ser Ser Tyr Asn Ser Val Gly Phe Trp Ala
1               5                   10                  15

<210> SEQ ID NO 152
<211> LENGTH: 13
<212> TYPE: PRT
<213> ORGANISM: Artificial Sequence
<220> FEATURE:
<223> OTHER INFORMATION: C26 LC CDR1

<400> SEQUENCE: 152

Gln Ala Ser Gln Ser Val Tyr Asn Asn Asn Asp Leu Ala
1               5                   10

<210> SEQ ID NO 153
<211> LENGTH: 7
<212> TYPE: PRT
<213> ORGANISM: Artificial Sequence
<220> FEATURE:
<223> OTHER INFORMATION: C26 LC CDR2

<400> SEQUENCE: 153

Glu Ala Ser Lys Leu Ala Ser
1               5

<210> SEQ ID NO 154
<211> LENGTH: 10
<212> TYPE: PRT
<213> ORGANISM: Artificial Sequence
<220> FEATURE:
<223> OTHER INFORMATION: C26 LC CDR3

<400> SEQUENCE: 154

Ala Gly Gly Trp Ser Gly Asn Phe Tyr Val
1               5                   10

<210> SEQ ID NO 155
<211> LENGTH: 13
<212> TYPE: PRT
<213> ORGANISM: Artificial Sequence
<220> FEATURE:
<223> OTHER INFORMATION: C27 LC CDR1

<400> SEQUENCE: 155

Gln Ala Ser Gln Ser Val Tyr Asp Gly Asn Trp Leu Cys
1               5                   10

<210> SEQ ID NO 156
```

```
<211> LENGTH: 7
<212> TYPE: PRT
<213> ORGANISM: Artificial Sequence
<220> FEATURE:
<223> OTHER INFORMATION: C27 LC CDR2

<400> SEQUENCE: 156

Lys Ala Ser Thr Leu Glu Ser
1               5

<210> SEQ ID NO 157
<211> LENGTH: 10
<212> TYPE: PRT
<213> ORGANISM: Artificial Sequence
<220> FEATURE:
<223> OTHER INFORMATION: C27 LC CDR3

<400> SEQUENCE: 157

Gln Gly Gly Phe Thr Ser Asn Ile Tyr Pro
1               5                   10

<210> SEQ ID NO 158
<211> LENGTH: 13
<212> TYPE: PRT
<213> ORGANISM: Artificial Sequence
<220> FEATURE:
<223> OTHER INFORMATION: C17 LC CDR1

<400> SEQUENCE: 158

Gln Ser Ser Gln Ser Val Tyr Asn Asn Asn Trp Leu Ala
1               5                   10

<210> SEQ ID NO 159
<211> LENGTH: 7
<212> TYPE: PRT
<213> ORGANISM: Artificial Sequence
<220> FEATURE:
<223> OTHER INFORMATION: C17 LC CDR2

<400> SEQUENCE: 159

Gly Thr Ser Glu Leu Ala Ser
1               5

<210> SEQ ID NO 160
<211> LENGTH: 10
<212> TYPE: PRT
<213> ORGANISM: Artificial Sequence
<220> FEATURE:
<223> OTHER INFORMATION: C17 LC CDR3

<400> SEQUENCE: 160

Leu Gly Thr Tyr Ser Ser Asn Ile His Val
1               5                   10

<210> SEQ ID NO 161
<211> LENGTH: 18
<212> TYPE: PRT
<213> ORGANISM: Artificial Sequence
<220> FEATURE:
<223> OTHER INFORMATION: Cys-apelin-17

<400> SEQUENCE: 161

Cys Lys Phe Arg Arg Gln Arg Pro Arg Leu Ser His Lys Gly Pro Met
1               5                   10                  15

Pro Phe
```

```
<210> SEQ ID NO 162
<211> LENGTH: 14
<212> TYPE: PRT
<213> ORGANISM: Artificial Sequence
<220> FEATURE:
<223> OTHER INFORMATION: pyr-apelin-13-Cys
<220> FEATURE:
<221> NAME/KEY: MISC_FEATURE
<222> LOCATION: (1)..(1)
<223> OTHER INFORMATION: Glu is a pyroglutamic acid

<400> SEQUENCE: 162

Glu Arg Pro Arg Leu Ser His Lys Gly Pro Met Pro Phe Cys
1               5                   10

<210> SEQ ID NO 163
<211> LENGTH: 13
<212> TYPE: PRT
<213> ORGANISM: Artificial Sequence
<220> FEATURE:
<223> OTHER INFORMATION: pyr-apelin-13
<220> FEATURE:
<221> NAME/KEY: MISC_FEATURE
<222> LOCATION: (1)..(1)
<223> OTHER INFORMATION: Glu is a pyroglutamic acid

<400> SEQUENCE: 163

Glu Arg Pro Arg Leu Ser His Lys Gly Pro Met Pro Phe
1               5                   10

<210> SEQ ID NO 164
<211> LENGTH: 14
<212> TYPE: PRT
<213> ORGANISM: Artificial Sequence
<220> FEATURE:
<223> OTHER INFORMATION: Cys(Q) apelin-13

<400> SEQUENCE: 164

Cys Gln Arg Pro Arg Leu Ser His Lys Gly Pro Met Pro Phe
1               5                   10

<210> SEQ ID NO 165
<211> LENGTH: 13
<212> TYPE: PRT
<213> ORGANISM: Artificial Sequence
<220> FEATURE:
<223> OTHER INFORMATION: biotin-apelin-13

<400> SEQUENCE: 165

Gln Arg Pro Arg Leu Ser His Lys Gly Pro Met Pro Phe
1               5                   10

<210> SEQ ID NO 166
<211> LENGTH: 17
<212> TYPE: PRT
<213> ORGANISM: Artificial Sequence
<220> FEATURE:
<223> OTHER INFORMATION: biotin-apelin-17

<400> SEQUENCE: 166

Lys Phe Arg Arg Gln Arg Pro Arg Leu Ser His Lys Gly Pro Met Pro
1               5                   10                  15

Phe

<210> SEQ ID NO 167
<211> LENGTH: 14
<212> TYPE: PRT
<213> ORGANISM: Artificial Sequence
```

-continued

```
<220> FEATURE:
<223> OTHER INFORMATION: biotin-apelin-(27-14)

<400> SEQUENCE: 167

Gly Pro Gly Ala Trp Gln Gly Gly Arg Arg Lys Phe Arg Arg
1               5                   10

<210> SEQ ID NO 168
<211> LENGTH: 5
<212> TYPE: PRT
<213> ORGANISM: Artificial Sequence
<220> FEATURE:
<223> OTHER INFORMATION: HC CDR1
<220> FEATURE:
<221> NAME/KEY: MISC_FEATURE
<222> LOCATION: (1)..(1)
<223> OTHER INFORMATION: Xaa is Ser or Thr
<220> FEATURE:
<221> NAME/KEY: MISC_FEATURE
<222> LOCATION: (4)..(4)
<223> OTHER INFORMATION: Xaa is Met or Val

<400> SEQUENCE: 168

Xaa Arg Asn Xaa Ser
1               5

<210> SEQ ID NO 169
<211> LENGTH: 14
<212> TYPE: PRT
<213> ORGANISM: Artificial Sequence
<220> FEATURE:
<223> OTHER INFORMATION: HC CDR2
<220> FEATURE:
<221> NAME/KEY: MISC_FEATURE
<222> LOCATION: (8)..(8)
<223> OTHER INFORMATION: Xaa is Tyr or Phe
<220> FEATURE:
<221> NAME/KEY: MISC_FEATURE
<222> LOCATION: (13)..(13)
<223> OTHER INFORMATION: Xaa is Lys or Gln

<400> SEQUENCE: 169

Ser Ile Gly Ser Ser Pro Trp Xaa Ala Ser Trp Ala Xaa Gly
1               5                   10

<210> SEQ ID NO 170
<211> LENGTH: 9
<212> TYPE: PRT
<213> ORGANISM: Artificial Sequence
<220> FEATURE:
<223> OTHER INFORMATION: HC CDR3
<220> FEATURE:
<221> NAME/KEY: MISC_FEATURE
<222> LOCATION: (7)..(7)
<223> OTHER INFORMATION: Xaa is Ala and Gly
<220> FEATURE:
<221> NAME/KEY: MISC_FEATURE
<222> LOCATION: (9)..(9)
<223> OTHER INFORMATION: Xaa is Val or Ile

<400> SEQUENCE: 170

Gly Gly Tyr Arg Pro Gly Xaa Ser Xaa
1               5

<210> SEQ ID NO 171
<211> LENGTH: 13
<212> TYPE: PRT
<213> ORGANISM: Artificial Sequence
<220> FEATURE:
<223> OTHER INFORMATION: LC CDR1
<220> FEATURE:
```

<221> NAME/KEY: MISC_FEATURE
<222> LOCATION: (13)..(13)
<223> OTHER INFORMATION: Xaa is Ala or Gly

<400> SEQUENCE: 171

Gln Ser Ser Gln Ser Val Tyr Asp Asn Asn Asp Leu Xaa
1               5                   10

<210> SEQ ID NO 172
<211> LENGTH: 10
<212> TYPE: PRT
<213> ORGANISM: Artificial Sequence
<220> FEATURE:
<223> OTHER INFORMATION: LC CDR3
<220> FEATURE:
<221> NAME/KEY: MISC_FEATURE
<222> LOCATION: (5)..(5)
<223> OTHER INFORMATION: Xaa is Ser or Asn

<400> SEQUENCE: 172

Ala Gly Gly Tyr Xaa Gly Asp Ile Tyr Thr
1               5                   10

<210> SEQ ID NO 173
<211> LENGTH: 5
<212> TYPE: PRT
<213> ORGANISM: Artificial Sequence
<220> FEATURE:
<223> OTHER INFORMATION: HC CDR1
<220> FEATURE:
<221> NAME/KEY: MISC_FEATURE
<222> LOCATION: (1)..(1)
<223> OTHER INFORMATION: Xaa is Asn or Ser
<220> FEATURE:
<221> NAME/KEY: MISC_FEATURE
<222> LOCATION: (4)..(4)
<223> OTHER INFORMATION: Xaa is Met or Ile

<400> SEQUENCE: 173

Xaa Tyr Ala Xaa Asp
1               5

<210> SEQ ID NO 174
<211> LENGTH: 16
<212> TYPE: PRT
<213> ORGANISM: Artificial Sequence
<220> FEATURE:
<223> OTHER INFORMATION: HC CDR2
<220> FEATURE:
<221> NAME/KEY: MISC_FEATURE
<222> LOCATION: (6)..(6)
<223> OTHER INFORMATION: Xaa is Arg, Gly, or His
<220> FEATURE:
<221> NAME/KEY: MISC_FEATURE
<222> LOCATION: (7)..(7)
<223> OTHER INFORMATION: Xaa is Arg, Ala, or Tyr
<220> FEATURE:
<221> NAME/KEY: MISC_FEATURE
<222> LOCATION: (9)..(9)
<223> OTHER INFORMATION: Xaa is Tyr or Cys

<400> SEQUENCE: 174

Val Ile Ala Pro Asn Xaa Xaa Thr Xaa Tyr Pro Thr Trp Ala Arg Gly
1               5                   10                  15

<210> SEQ ID NO 175
<211> LENGTH: 9
<212> TYPE: PRT
<213> ORGANISM: Artificial Sequence
<220> FEATURE:
<223> OTHER INFORMATION: HC CDR3

```
<220> FEATURE:
<221> NAME/KEY: MISC_FEATURE
<222> LOCATION: (4)..(4)
<223> OTHER INFORMATION: Xaa is Glu or Asp
<220> FEATURE:
<221> NAME/KEY: MISC_FEATURE
<222> LOCATION: (5)..(5)
<223> OTHER INFORMATION: Xaa is Pro, Ala, Ser, or Thr
<220> FEATURE:
<221> NAME/KEY: MISC_FEATURE
<222> LOCATION: (7)..(7)
<223> OTHER INFORMATION: Xaa is Ala or Ser

<400> SEQUENCE: 175

Tyr Pro Ile Xaa Xaa Gly Xaa Asn Ile
1               5

<210> SEQ ID NO 176
<211> LENGTH: 13
<212> TYPE: PRT
<213> ORGANISM: Artificial Sequence
<220> FEATURE:
<223> OTHER INFORMATION: LC CDR1
<220> FEATURE:
<221> NAME/KEY: MISC_FEATURE
<222> LOCATION: (7)..(7)
<223> OTHER INFORMATION: Xaa is Asp or Gly
<220> FEATURE:
<221> NAME/KEY: MISC_FEATURE
<222> LOCATION: (8)..(8)
<223> OTHER INFORMATION: Xaa is Tyr, Asn, or Met

<400> SEQUENCE: 176

Gln Ser Ser Glu Ser Val Xaa Xaa Asn Asn Gln Leu Ser
1               5                   10

<210> SEQ ID NO 177
<211> LENGTH: 16
<212> TYPE: PRT
<213> ORGANISM: Artificial Sequence
<220> FEATURE:
<223> OTHER INFORMATION: HC CDR2
<220> FEATURE:
<221> NAME/KEY: MISC_FEATURE
<222> LOCATION: (6)..(6)
<223> OTHER INFORMATION: Xaa is Gly or Ser

<400> SEQUENCE: 177

Val Ile Ala Pro Ser Xaa Thr Thr Tyr Tyr Pro Thr Trp Ala Lys Gly
1               5                   10                  15

<210> SEQ ID NO 178
<211> LENGTH: 9
<212> TYPE: PRT
<213> ORGANISM: Artificial Sequence
<220> FEATURE:
<223> OTHER INFORMATION: HC CDR2
<220> FEATURE:
<221> NAME/KEY: MISC_FEATURE
<222> LOCATION: (9)..(9)
<223> OTHER INFORMATION: Xaa is Ile or Val

<400> SEQUENCE: 178

Tyr Pro Ile Asp Pro Gly Ser Asn Xaa
1               5

<210> SEQ ID NO 179
<211> LENGTH: 5
<212> TYPE: PRT
<213> ORGANISM: Artificial Sequence
<220> FEATURE:
```

```
<223> OTHER INFORMATION: HC CDR1
<220> FEATURE:
<221> NAME/KEY: MISC_FEATURE
<222> LOCATION: (1)..(1)
<223> OTHER INFORMATION: Xaa is Asn or Ser
<220> FEATURE:
<221> NAME/KEY: MISC_FEATURE
<222> LOCATION: (2)..(2)
<223> OTHER INFORMATION: Xaa is Tyr or His

<400> SEQUENCE: 179

Xaa Xaa Ala Met Asp
1               5

<210> SEQ ID NO 180
<211> LENGTH: 9
<212> TYPE: PRT
<213> ORGANISM: Artificial Sequence
<220> FEATURE:
<223> OTHER INFORMATION: HC CDR3
<220> FEATURE:
<221> NAME/KEY: MISC_FEATURE
<222> LOCATION: (5)..(5)
<223> OTHER INFORMATION: Xaa is Val or Ala

<400> SEQUENCE: 180

Tyr Pro Ile Asp Xaa Gly Ala Asn Val
1               5

<210> SEQ ID NO 181
<211> LENGTH: 12
<212> TYPE: PRT
<213> ORGANISM: Artificial Sequence
<220> FEATURE:
<223> OTHER INFORMATION: Apelin Peptide 1-12

<400> SEQUENCE: 181

Gln Arg Pro Arg Leu Ser His Lys Gly Pro Met Pro
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Apelin Peptide 2-13

<400> SEQUENCE: 182

Arg Pro Arg Leu Ser His Lys Gly Pro Met Pro Phe
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Apelin Peptide 3-13

<400> SEQUENCE: 183

Pro Arg Leu Ser His Lys Gly Pro Met Pro Phe
1               5                   10

<210> SEQ ID NO 184
<211> LENGTH: 10
<212> TYPE: PRT
<213> ORGANISM: Artificial Sequence
<220> FEATURE:
<223> OTHER INFORMATION: Apelin Peptide 4-13
```

```
<400> SEQUENCE: 184

Arg Leu Ser His Lys Gly Pro Met Pro Phe
1               5                   10

<210> SEQ ID NO 185
<211> LENGTH: 9
<212> TYPE: PRT
<213> ORGANISM: Artificial Sequence
<220> FEATURE:
<223> OTHER INFORMATION: Apelin Peptide 5-13

<400> SEQUENCE: 185

Leu Ser His Lys Gly Pro Met Pro Phe
1               5

<210> SEQ ID NO 186
<211> LENGTH: 8
<212> TYPE: PRT
<213> ORGANISM: Artificial Sequence
<220> FEATURE:
<223> OTHER INFORMATION: Apelin Peptide 6-13

<400> SEQUENCE: 186

Ser His Lys Gly Pro Met Pro Phe
1               5

<210> SEQ ID NO 187
<211> LENGTH: 7
<212> TYPE: PRT
<213> ORGANISM: Artificial Sequence
<220> FEATURE:
<223> OTHER INFORMATION: Apelin Peptide 7-13

<400> SEQUENCE: 187

His Lys Gly Pro Met Pro Phe
1               5

<210> SEQ ID NO 188
<211> LENGTH: 6
<212> TYPE: PRT
<213> ORGANISM: Artificial Sequence
<220> FEATURE:
<223> OTHER INFORMATION: Apelin Peptide 8-13

<400> SEQUENCE: 188

Lys Gly Pro Met Pro Phe
1               5

<210> SEQ ID NO 189
<211> LENGTH: 5
<212> TYPE: PRT
<213> ORGANISM: Artificial Sequence
<220> FEATURE:
<223> OTHER INFORMATION: Apelin Peptide 9-13

<400> SEQUENCE: 189

Gly Pro Met Pro Phe
1               5

<210> SEQ ID NO 190
<211> LENGTH: 4
<212> TYPE: PRT
<213> ORGANISM: Artificial Sequence
<220> FEATURE:
<223> OTHER INFORMATION: Apelin Peptide 10-13

<400> SEQUENCE: 190
```

```
Pro Met Pro Phe
1

<210> SEQ ID NO 191
<211> LENGTH: 3
<212> TYPE: PRT
<213> ORGANISM: Artificial Sequence
<220> FEATURE:
<223> OTHER INFORMATION: Apelin Peptide 11-13

<400> SEQUENCE: 191

Met Pro Phe
1

<210> SEQ ID NO 192
<211> LENGTH: 6
<212> TYPE: PRT
<213> ORGANISM: Artificial Sequence
<220> FEATURE:
<223> OTHER INFORMATION: Peptide 8A

<400> SEQUENCE: 192

Ala Gly Pro Met Pro Phe
1               5

<210> SEQ ID NO 193
<211> LENGTH: 6
<212> TYPE: PRT
<213> ORGANISM: Artificial Sequence
<220> FEATURE:
<223> OTHER INFORMATION: Peptide 9A

<400> SEQUENCE: 193

Lys Ala Pro Met Pro Phe
1               5

<210> SEQ ID NO 194
<211> LENGTH: 6
<212> TYPE: PRT
<213> ORGANISM: Artificial Sequence
<220> FEATURE:
<223> OTHER INFORMATION: Peptide 10A

<400> SEQUENCE: 194

Lys Gly Ala Met Pro Phe
1               5

<210> SEQ ID NO 195
<211> LENGTH: 6
<212> TYPE: PRT
<213> ORGANISM: Artificial Sequence
<220> FEATURE:
<223> OTHER INFORMATION: Peptide 11A

<400> SEQUENCE: 195

Lys Gly Pro Ala Pro Phe
1               5

<210> SEQ ID NO 196
<211> LENGTH: 6
<212> TYPE: PRT
<213> ORGANISM: Artificial Sequence
<220> FEATURE:
<223> OTHER INFORMATION: Peptide 12A

<400> SEQUENCE: 196
```

```
Lys Gly Pro Met Ala Phe
1               5

<210> SEQ ID NO 197
<211> LENGTH: 6
<212> TYPE: PRT
<213> ORGANISM: Artificial Sequence
<220> FEATURE:
<223> OTHER INFORMATION: Peptide 13A

<400> SEQUENCE: 197

Lys Gly Pro Met Pro Ala
1               5

<210> SEQ ID NO 198
<211> LENGTH: 11
<212> TYPE: PRT
<213> ORGANISM: Artificial Sequence
<220> FEATURE:
<223> OTHER INFORMATION: Apelin Peptide 1-11

<400> SEQUENCE: 198

Gln Arg Pro Arg Leu Ser His Lys Gly Pro Met
1               5                   10

<210> SEQ ID NO 199
<211> LENGTH: 10
<212> TYPE: PRT
<213> ORGANISM: Artificial Sequence
<220> FEATURE:
<223> OTHER INFORMATION: Apelin Peptide 1-10

<400> SEQUENCE: 199

Gln Arg Pro Arg Leu Ser His Lys Gly Pro
1               5                   10

<210> SEQ ID NO 200
<211> LENGTH: 9
<212> TYPE: PRT
<213> ORGANISM: Artificial Sequence
<220> FEATURE:
<223> OTHER INFORMATION: Apelin Peptide 1-9

<400> SEQUENCE: 200

Gln Arg Pro Arg Leu Ser His Lys Gly
1               5

<210> SEQ ID NO 201
<211> LENGTH: 8
<212> TYPE: PRT
<213> ORGANISM: Artificial Sequence
<220> FEATURE:
<223> OTHER INFORMATION: Apelin Peptide 1-8

<400> SEQUENCE: 201

Gln Arg Pro Arg Leu Ser His Lys
1               5

<210> SEQ ID NO 202
<211> LENGTH: 7
<212> TYPE: PRT
<213> ORGANISM: Artificial Sequence
<220> FEATURE:
<223> OTHER INFORMATION: Apelin Peptide 1-7

<400> SEQUENCE: 202

Gln Arg Pro Arg Leu Ser His
```

```
1               5

<210> SEQ ID NO 203
<211> LENGTH: 6
<212> TYPE: PRT
<213> ORGANISM: Artificial Sequence
<220> FEATURE:
<223> OTHER INFORMATION: Apelin Peptide 1-6

<400> SEQUENCE: 203

Gln Arg Pro Arg Leu Ser
1               5

<210> SEQ ID NO 204
<211> LENGTH: 5
<212> TYPE: PRT
<213> ORGANISM: Artificial Sequence
<220> FEATURE:
<223> OTHER INFORMATION: Apelin Peptide 1-5

<400> SEQUENCE: 204

Gln Arg Pro Arg Leu
1               5

<210> SEQ ID NO 205
<211> LENGTH: 4
<212> TYPE: PRT
<213> ORGANISM: Artificial Sequence
<220> FEATURE:
<223> OTHER INFORMATION: Apelin Peptide 1-4

<400> SEQUENCE: 205

Gln Arg Pro Arg
1

<210> SEQ ID NO 206
<211> LENGTH: 5
<212> TYPE: PRT
<213> ORGANISM: Artificial Sequence
<220> FEATURE:
<223> OTHER INFORMATION: 1A

<400> SEQUENCE: 206

Ala Arg Pro Arg Leu
1               5

<210> SEQ ID NO 207
<211> LENGTH: 5
<212> TYPE: PRT
<213> ORGANISM: Artificial Sequence
<220> FEATURE:
<223> OTHER INFORMATION: 2A

<400> SEQUENCE: 207

Gln Ala Pro Arg Leu
1               5

<210> SEQ ID NO 208
<211> LENGTH: 5
<212> TYPE: PRT
<213> ORGANISM: Artificial Sequence
<220> FEATURE:
<223> OTHER INFORMATION: 3A

<400> SEQUENCE: 208

Gln Arg Ala Arg Leu
1               5
```

<210> SEQ ID NO 209
<211> LENGTH: 5
<212> TYPE: PRT
<213> ORGANISM: Artificial Sequence
<220> FEATURE:
<223> OTHER INFORMATION: 4A

<400> SEQUENCE: 209

Gln Arg Pro Ala Leu
1               5

<210> SEQ ID NO 210
<211> LENGTH: 5
<212> TYPE: PRT
<213> ORGANISM: Artificial Sequence
<220> FEATURE:
<223> OTHER INFORMATION: 5A

<400> SEQUENCE: 210

Gln Arg Pro Arg Ala
1               5

<210> SEQ ID NO 211
<211> LENGTH: 113
<212> TYPE: PRT
<213> ORGANISM: Artificial Sequence
<220> FEATURE:
<223> OTHER INFORMATION: Humanized VH

<400> SEQUENCE: 211

Gln Ser Leu Glu Glu Ser Gly Gly Gly Leu Val Gln Pro Gly Gly Ser
1               5                   10                  15

Leu Arg Leu Ser Cys Ala Val Ser Gly Ile Asp Leu Tyr Ser Asn Arg
            20                  25                  30

Met Ser Trp Val Arg Gln Ala Pro Gly Lys Gly Leu Glu Trp Val Ser
        35                  40                  45

Ser Ile Gly Ser Ser Pro Trp Tyr Ala Ser Trp Ala Gln Gly Arg Phe
    50                  55                  60

Thr Ile Ser Arg Asp Asn Ser Asn Thr Leu Tyr Leu Gln Met Asn Ser
65                  70                  75                  80

Leu Thr Ala Glu Asp Thr Ala Val Tyr Tyr Cys Ala Lys Gly Gly Tyr
                85                  90                  95

Arg Pro Gly Ala Ser Val Trp Gly Gln Gly Thr Leu Val Thr Val Ser
            100                 105                 110

Ser

<210> SEQ ID NO 212
<211> LENGTH: 113
<212> TYPE: PRT
<213> ORGANISM: Artificial Sequence
<220> FEATURE:
<223> OTHER INFORMATION: Humanized VH

<400> SEQUENCE: 212

Gln Ser Leu Glu Glu Ser Gly Gly Gly Leu Val Gln Pro Gly Gly Ser
1               5                   10                  15

Leu Arg Leu Ser Cys Ala Val Ser Gly Ile Asp Leu Tyr Ser Asn Arg
            20                  25                  30

Met Ser Trp Val Arg Gln Ala Pro Gly Lys Gly Leu Glu Trp Val Ser
        35                  40                  45

Ser Ile Gly Ser Ser Pro Trp Tyr Ala Ser Trp Ala Gln Gly Arg Phe
                50                  55                  60

Thr Ile Ser Arg Asp Asn Ser Asn Thr Val Tyr Leu Gln Met Asn Ser
 65                  70                  75                  80

Leu Thr Ala Glu Asp Thr Ala Thr Tyr Phe Cys Ala Lys Gly Gly Tyr
                 85                  90                  95

Arg Pro Gly Ala Ser Val Trp Gly Gln Gly Thr Leu Val Thr Val Ser
                100                 105                 110

Ser

<210> SEQ ID NO 213
<211> LENGTH: 113
<212> TYPE: PRT
<213> ORGANISM: Artificial Sequence
<220> FEATURE:
<223> OTHER INFORMATION: Humanized VH

<400> SEQUENCE: 213

Gln Ser Leu Glu Glu Ser Gly Gly Gly Leu Val Gln Pro Gly Gly Ser
 1               5                  10                  15

Leu Arg Leu Ser Cys Ala Val Ser Gly Ile Asp Leu Tyr Ser Asn Arg
                 20                  25                  30

Met Ser Trp Val Arg Gln Ala Pro Gly Lys Gly Leu Glu Trp Val Gly
             35                  40                  45

Ser Ile Gly Ser Ser Pro Trp Tyr Ala Ser Trp Ala Gln Gly Arg Phe
                50                  55                  60

Thr Ile Ser Arg Asp Asn Ser Asn Thr Val Tyr Leu Gln Met Asn Ser
 65                  70                  75                  80

Leu Thr Ala Glu Asp Thr Ala Thr Tyr Phe Cys Ala Lys Gly Gly Tyr
                 85                  90                  95

Arg Pro Gly Ala Ser Val Trp Gly Gln Gly Thr Leu Val Thr Val Ser
                100                 105                 110

Ser

<210> SEQ ID NO 214
<211> LENGTH: 113
<212> TYPE: PRT
<213> ORGANISM: Artificial Sequence
<220> FEATURE:
<223> OTHER INFORMATION: Humanized VH

<400> SEQUENCE: 214

Gln Ser Leu Glu Glu Ser Gly Gly Gly Leu Val Gln Pro Gly Gly Ser
 1               5                  10                  15

Leu Arg Leu Ser Cys Thr Val Ser Gly Ile Asp Leu Tyr Ser Asn Arg
                 20                  25                  30

Met Ser Trp Val Arg Gln Ala Pro Gly Lys Gly Leu Glu Trp Val Gly
             35                  40                  45

Ser Ile Gly Ser Ser Pro Trp Tyr Ala Ser Trp Ala Gln Gly Arg Phe
                50                  55                  60

Thr Ile Ser Arg Asp Asn Ser Asn Thr Val Tyr Leu Lys Met Asn Ser
 65                  70                  75                  80

Pro Thr Ala Glu Asp Thr Ala Thr Tyr Phe Cys Ala Lys Gly Gly Tyr
                 85                  90                  95

Arg Pro Gly Ala Ser Val Trp Gly Gln Gly Thr Leu Val Thr Val Ser
                100                 105                 110

Ser

<210> SEQ ID NO 215
<211> LENGTH: 110
<212> TYPE: PRT
<213> ORGANISM: Artificial Sequence
<220> FEATURE:
<223> OTHER INFORMATION: Humanized VL

<400> SEQUENCE: 215

```
Asp Ile Gln Leu Thr Gln Ser Pro Ser Ser Leu Ser Ala Ser Val Gly
1               5                   10                  15

Asp Arg Val Thr Ile Thr Cys Gln Ser Gln Ser Ile Tyr Asp Asn
            20                  25                  30

Asn Asp Leu Ala Trp Tyr Gln Gln Lys Pro Gly Lys Thr Pro Lys Arg
        35                  40                  45

Leu Ile Tyr Leu Ala Ser Ser Leu Asp Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Gly Tyr Ser Gly
                85                  90                  95

Asp Ile Tyr Thr Phe Gly Gly Gly Thr Lys Val Glu Ile Lys
            100                 105                 110
```

<210> SEQ ID NO 216
<211> LENGTH: 110
<212> TYPE: PRT
<213> ORGANISM: Artificial Sequence
<220> FEATURE:
<223> OTHER INFORMATION: Humanized VL

<400> SEQUENCE: 216

```
Ala Gln Val Leu Thr Gln Ser Pro Ser Ser Leu Ser Ala Ser Val Gly
1               5                   10                  15

Asp Arg Val Thr Ile Ala Cys Gln Ser Ser Gln Ser Val Tyr Asp Asn
            20                  25                  30

Asn Asp Leu Ala Trp Tyr Gln Gln Lys Ala Gly Gln Thr Pro Lys Arg
        35                  40                  45

Leu Ile Tyr Leu Ala Ser Ser Leu Asp Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Cys Glu Asp Val Ala Thr Tyr Tyr Cys Ala Gly Gly Tyr Ser Gly
                85                  90                  95

Asp Ile Tyr Thr Phe Gly Gly Gly Thr Glu Val Val Val Glu
            100                 105                 110
```

<210> SEQ ID NO 217
<211> LENGTH: 113
<212> TYPE: PRT
<213> ORGANISM: Artificial Sequence
<220> FEATURE:
<223> OTHER INFORMATION: B24 Heavy Chain Variable Region

<400> SEQUENCE: 217

```
Gln Ser Leu Glu Glu Ser Gly Gly Gly Leu Val Gln Pro Gly Gly Ser
1               5                   10                  15

Leu Arg Leu Ser Cys Thr Val Ser Gly Ile Asp Leu Tyr Thr Asn Arg
            20                  25                  30
```

Val Ser Trp Val Arg Gln Ala Pro Gly Lys Gly Leu Glu Trp Val Gly
        35                  40                  45

Ser Ile Gly Ser Ser Pro Trp Tyr Ala Ser Trp Ala Gln Gly Arg Phe
 50                  55                  60

Thr Ile Ser Arg Asp Asn Ser Asn Thr Val Tyr Leu Lys Met Asn Ser
65                  70                  75                  80

Pro Thr Ala Glu Asp Thr Ala Thr Tyr Phe Cys Ala Lys Gly Gly Tyr
                85                  90                  95

Arg Pro Gly Gly Ser Ile Trp Gly Gln Gly Thr Leu Val Thr Val Ser
            100                 105                 110

Ser

<210> SEQ ID NO 218
<211> LENGTH: 113
<212> TYPE: PRT
<213> ORGANISM: Artificial Sequence
<220> FEATURE:
<223> OTHER INFORMATION: B25 Heavy Chain Variable Region

<400> SEQUENCE: 218

Gln Ser Leu Glu Glu Ser Gly Gly Gly Leu Val Gln Pro Gly Gly Ser
1               5                   10                  15

Leu Arg Leu Ser Cys Thr Val Ser Gly Ile Asp Leu Tyr Thr Asn Arg
            20                  25                  30

Met Ser Trp Val Arg Gln Ala Pro Gly Lys Gly Leu Glu Trp Val Gly
        35                  40                  45

Ser Ile Gly Ser Ser Pro Trp Phe Ala Ser Trp Ala Leu Gly Arg Phe
 50                  55                  60

Thr Ile Ser Arg Asp Asn Ser Asn Thr Val Tyr Leu Lys Met Asn Ser
65                  70                  75                  80

Pro Thr Ala Glu Asp Thr Ala Thr Tyr Phe Cys Ala Lys Gly Gly Tyr
                85                  90                  95

Arg Pro Gly Ala Ser Val Trp Gly Gln Gly Thr Leu Val Thr Val Ser
            100                 105                 110

Ser

<210> SEQ ID NO 219
<211> LENGTH: 110
<212> TYPE: PRT
<213> ORGANISM: Artificial Sequence
<220> FEATURE:
<223> OTHER INFORMATION: B24 Light Chain Variable Region

<400> SEQUENCE: 219

Asp Ile Gln Leu Thr Gln Ser Pro Ser Ser Leu Ser Ala Ser Val Gly
1               5                   10                  15

Asp Arg Val Thr Ile Thr Cys Gln Ser Ser Gln Ser Ile Tyr Asp Asn
            20                  25                  30

Asn Asp Leu Gly Trp Tyr Gln Gln Lys Pro Gly Lys Thr Pro Lys Arg
        35                  40                  45

Leu Ile Tyr Leu Ala Ser Ser Leu Asp Ser Gly Val Pro Ser Arg Phe
 50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Gly Tyr Ser Gly
                85                  90                  95

Asp Ile Tyr Thr Phe Gly Gly Gly Thr Lys Val Glu Ile Lys

```
                      100                 105                 110

<210> SEQ ID NO 220
<211> LENGTH: 110
<212> TYPE: PRT
<213> ORGANISM: Artificial Sequence
<220> FEATURE:
<223> OTHER INFORMATION: B25 Light Chain Variable Region

<400> SEQUENCE: 220

Asp Ile Gln Leu Thr Gln Ser Pro Ser Ser Leu Ser Ala Ser Val Gly
1               5                   10                  15

Asp Arg Val Thr Ile Thr Cys Gln Ser Ser Gln Ser Ile Tyr Asp Asn
            20                  25                  30

Asn Asp Leu Ala Trp Tyr Gln Gln Lys Pro Gly Lys Thr Pro Lys Arg
        35                  40                  45

Leu Ile Tyr Leu Ala Ser Ser Leu Asp Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Ala Gly Gly Tyr Asn Gly
                85                  90                  95

Asp Ile Tyr Thr Phe Gly Gly Gly Thr Lys Val Glu Ile Lys
            100                 105                 110

<210> SEQ ID NO 221
<211> LENGTH: 77
<212> TYPE: PRT
<213> ORGANISM: Homo sapiens

<400> SEQUENCE: 221

Met Asn Leu Arg Leu Cys Val Gln Ala Leu Leu Leu Leu Trp Leu Ser
1               5                   10                  15

Leu Thr Ala Val Cys Gly Gly Ser Leu Met Pro Leu Pro Asp Gly Asn
            20                  25                  30

Gly Leu Glu Asp Gly Asn Val Arg His Leu Val Gln Pro Arg Gly Ser
        35                  40                  45

Arg Asn Gly Pro Gly Pro Trp Gln Gly Gly Arg Arg Lys Phe Arg Arg
    50                  55                  60

Gln Arg Pro Arg Leu Ser His Lys Gly Pro Met Pro Phe
65                  70                  75
```

ANTI-APELIN ANTIBODIES AND USES THEREOF

CROSS REFERENCE TO RELATED APPLICATIONS

This application is a Section 371 of International Application No. PCT/US2018/047144, filed Aug. 21, 2018, which published in the English language on Feb. 28, 2019 under International Publication No. WO 2019/040390 A1, which claims priority to U.S. Provisional Application No. 62/549,523, filed on Aug. 24, 2017; U.S. Provisional Application No. 62/579,287, filed on Oct. 31, 2017; U.S. Provisional Application No. 62/656,586, filed on Apr. 12, 2018; and U.S. Provisional Application No. 62/658,111, filed on Apr. 16, 2018. Each disclosure is incorporated herein by reference in its entirety.

FIELD OF THE INVENTION

This invention relates to monoclonal anti-apelin antibodies, nucleic acids and expression vectors encoding the antibodies, recombinant cells containing the vectors, and compositions comprising the antibodies. Methods of making the antibodies, methods of using the antibodies for diagnostic purposes in measuring apelin levels in blood and/or tissue, and methods of using the antibodies to treat diseases including diabetic retinopathy (DR; including proliferative diabetic retinopathy (PDR) and non-proliferative diabetic retinopathy (NPDR)), age-related macular degeneration (AMD), diabetic macular edema (DME), macular edema following retinal vein occlusion (RVO), retinal degeneration, myopic choroidal neovascularization (mCNV), diabetic nephropathy, chronic kidney disease (CKD), non-alcoholic steatohepatitis (NASH), liver cirrhosis, plaque neovascularization, rubeosis iridis, neovascular glaucoma, corneal neovascularization (CNV), retinopathy of prematurity (ROP), retinopathy, macular degeneration, ovarian hyperstimulation syndrome (OHSS), uterine bleeding, endometriosis, endometrial hyperplasia and cancer, myometrial leiomyomas, adenomyosis, cancer (e.g., solid tumors and hematologic malignancies), fibrosis (e.g., pathological and physiological fibrosis, renal fibrosis, cardiac fibrosis, liver fibrosis, and pulmonary fibrosis), and/or associated complications are also provided.

REFERENCE TO SEQUENCE LISTING SUBMITTED ELECTRONICALLY

This application contains a sequence listing, which is submitted electronically via EFS-Web as an ASCII formatted sequence listing with a file name "689204.1U1 Sequence Listing" and a creation date of Feb. 5, 2020 and having a size of 88 kb. The sequence listing submitted via EFS-Web is part of the specification and is herein incorporated by reference in its entirety.

BACKGROUND OF THE INVENTION

Apelin is a naturally occurring peptide with several endogenous forms. It is initially produced as a 77-amino acid precursor, preproapelin, which is proteolytically processed into apelin-36 (or apelin 36) (containing the C-terminal 36 amino acids of the apelin precursor), apelin-17 (or apelin 17) (containing the C-terminal 17 amino acids of preproapelin; K17F) and apelin-13 (or apelin 13) (containing the C-terminal 13 amino acids of preproapelin) (Tatemoto et al., Biochem Biophys Res. Commun. 251(2):471-6 (1998); Habata et al., Biochim Biophys Acta 1452(1):25-35 (1999); Lee et al., J. Neurochem. 74(1):34-41 (2000)). Other forms of apelin derived from the 77-amino acid precursor have been reported as well (Mesmin et al., J Proteome Res. 10(11):5222-31 (2011); Shin et al., Biochim Biophys Acta. 1861(8):1901-12 (2017)). The N-terminal glutamine residue of apelin 13 can be pyroglutamylated, producing the pyroglutamyl form of apelin 13 (pE13F). Apelin is the endogenous ligand of apelin receptor APJ (also named apelinR, AGTRL1, or APLNR). APJ is a member of the G protein-coupled receptor gene family. Apelin binds to and activates APJ and triggers a wide range of downstream signaling events, including downregulation of forskolin-induced cAMP production and promotion of phosphorylation of extracellular signal-regulated kinases (ERKs), Akt, and p70 S6 kinase (De Mota, Neuroendocrinology 72(6):400-7 (2000); Li et al., Front Biosci. 13:3786-92 (2008); Masri et al., Biochem Biophys Res Commun. 290(1):539-45 (2002); Liu et al., Biochem Biophys Res Commun. 468(4):617-21 (2015); Masri et al., FASEB J. 18(15):1909-11 (2004); O'Carroll et al., J Endocrinol. 219(1):R13-35 (2013)). Both K17F and pE13F can induce APJ receptor internalization. K17F has higher affinity than pE13F for APJ, whereas apelin-36 has similar affinity to pE13F (Iturrioz et al., J Biol Chem. 285(42):32627-37 (2010); Medhurst et al., J Neurochem. 84(5):1162-72 (2003)). Both apelin and APJ are expressed in the central nervous system and peripheral tissues (O'Carroll et al., J Endocrinol. 219(1):R13-35 (2013)). The apelin/APJ axis regulates many physiological functions including cardiac contractibility, blood pressure, cardiovascular tone, tissue angiogenesis, water homeostasis, gastrointestinal track physiology, proliferation of vascular smooth muscle cells (VSMCs) and other cell types, monocyte adhesion to human umbilical vein endothelial cells, cardiac repair post-myocardial infarction, and pathological fibrosis in several tissues or organs (O'Carroll et al., J Endocrinol. 219(1):R13-35 (2013)).

Apelin plays an important role in angiogenesis and cell proliferation of endothelial cells (ECs) (Kalin et al., Dev Biol. 305(2):599-614 (2007); Kasai et al., Biochem Biophys Res Commun. 325(2):395-400 (2004)). Both apelin and APJ are expressed on ECs of newly developing blood vessels during angiogenesis (Kidoya et al., EMBO J. 27(3):522-34 (2008); Saint-Geniez et al., Mech Dev. 110(1-2):183-6 (2002)) and the expression of apelin is induced by hypoxia (Kasai et al., Arterioscler Thromb Vasc Biol. 30(11):2182-7 (2010)). Apelin knockout mice have impaired retinal vascularization and ocular development (Kasai et al., Arterioscler Thromb Vasc Biol. 28(10):1717-22 (2008)), implicating an important role for apelin in retinal development. The vitreous concentration of apelin is higher in patients with proliferative diabetic retinopathy (PDR) than in individuals without diabetes (Tao et al., Invest Ophthalmol Vis Sci. 51(8):4237-42 (2010)). The elevated apelin level can exert strong angiogenic and proliferative effects and lead to pathological changes in the retina of diabetes and other eye diseases. An apelin-neutralizing monoclonal antibody (mAb) can specifically bind to apelin and block its biological activity on cells that express the apelin receptor APJ; it can also be called an anti-apelin mAb with neutralizing activity. Agents such as an apelin-neutralizing mAb could be used to treat diabetic retinopathy (DR), age-related macular degeneration (AMD), and diabetic macular edema (DME). Since the apelin/APJ axis could work with the VEGF pathway in a cooperative manner, a combination of an apelin-neutralizing mAb with a VEGF blocker such as ranibizumab (Lucentis®) could have an additive or even synergistic therapeutic effect in patients with DR, DME, AMD, and/or other eye diseases. A bispecific antibody that targets both apelin and VEGF could have a similar effect.

Apelin-13 has been shown to promote tumor proliferation in various types of cancers, including breast, hepatocellular, lymphatic, lung and ovarian cancer. Apelin and APJ expression is upregulated in various tumors (Sorli et al., Oncogene. 26(55):7692-9 (2007); Picault et al., Eur J Cancer. 50(3):663-74 (2014); Zuurbier et al., Oncotarget. 8(26):42949-42961 (2017); Muto et al., Anticancer Res. 34(10):5313-20 (2014)). Apelin is a potent activator of tumor neoangiogenesis and proliferation through binding and activation of its receptor APJ (Sorli et al., Drug Discov Today. 11(23-24):1100-6 (2006)). Thus, blockade of apelin action with an apelin-neutralizing mAb could be employed to treat various cancers where the apelin/APJ axis plays a role in cancer cell growth and/or angiogenesis near the tumor site. An apelin-neutralizing mAb could be combined with Avastin® or other anti-VEGF and/or anti-angiogenic agents to achieve an additive or even synergistic effect in cancer treatment. Further, an apelin-neutralizing mAb could be combined with other anti-cancer agents such as those for chemotherapy, inhibition of tumor growth or immune-oncology therapy to achieve greater efficacy.

Apelin is also associated with hepatic diseases. It is overexpressed in activated hepatic stellate cells (HSCs) of cirrhotic rats and plays an important role in both angiogenesis and fibrosis in these animals (Principe et al., Hepatology. 48(4):1193-201 (2008)). Apelin is also overexpressed in the HSCs of human cirrhotic liver (Melgar-Lesmes et al., Endocrinology. 151(11):5306-14 (2010)) as does APJ (Yokomori et al., J Gastroenterol. 46(2):222-31 (2011)). On the other hand, both hypoxia and proinflammatory factors upregulate APJ expression in human HSCs and hepatocytes. Patients with liver cirrhosis have increased serum levels of apelin. Moreover, serum apelin level is associated with the severity of chronic liver disease. These findings suggest that apelin can play an important role in the pathogenesis of liver diseases such as non-alcoholic steatohepatitis (NASH), liver fibrosis and liver cirrhosis. An apelin-neutralizing mAb could be used to treat these liver diseases.

Apelin has been shown to promote diabetic nephropathy in rodents by enhancing the permeability of glomerular endothelial cells and inducing podocyte dysfunction (Guo et al., J Cell Mol Med. 19(9):2273-85 (2015)). It has also been found to be involved in the progression of diabetic nephropathy by inhibiting autophagy in podocytes (Liu et al., Cell Death Dis. 8(8):e3006 (2017)). Thus, an apelin-neutralizing mAb could be used in the treatment of diabetic nephropathy and chronic kidney disease.

BRIEF SUMMARY OF THE INVENTION

In one general aspect, the invention relates to isolated monoclonal antibodies or antigen-binding fragments thereof that specifically bind apelin.

Provided are isolated monoclonal antibodies or antigen-binding fragments thereof comprising a heavy chain complementarity determining region 1 (HCDR1), HCDR2, HCDR3, a light chain complementarity determining region 1 (LCDR1), LCDR2, and LCDR3, having the polypeptide sequences of:

(1) SEQ ID NOs:168, 169, 170, 171, 102, and 172, respectively;
(2) SEQ ID NOs:50, 51, 52, 110, 111, and 112, respectively;
(3) SEQ ID NOs:173, 174, 175, 176, 114, and 115, respectively;
(4) SEQ ID NOs:68, 177, 178, 128, 129, and 130, respectively;
(5) SEQ ID NOs:74, 75, 76, 134, 135, and 136, respectively;
(6) SEQ ID NOs:179, 78, 180, 137, 138, and 139, respectively;
(7) SEQ ID NOs:83, 84, 85, 143, 144, and 145, respectively;
(8) SEQ ID NOs:86, 87, 88, 146, 147, and 148, respectively;
(9) SEQ ID NOs:89, 90, 91, 149, 150, and 151, respectively;
(10) SEQ ID NOs:92, 93, 94, 152, 153, and 154, respectively;
(11) SEQ ID NOs:95, 96, 97, 155, 156, and 157, respectively; or
(12) SEQ ID NOs:98, 99, 100, 158, 159, and 160, respectively;

wherein the antibody or antigen-binding fragment thereof specifically binds apelin, preferably human apelin. SEQ ID NO:168 is represented by the amino acid sequence $X_1NRX_2S$, wherein $X_1$ is an amino acid selected from S or T, and $X_2$ is an amino acid selected from M or V. SEQ ID NO:169 is represented by amino acid sequence $SIGSSPWX_1ASWAX_2G$, wherein $X_1$ is an amino acid selected from Y or F, and $X_2$ is selected from Q or L. SEQ ID NO:170 is represented by amino acid sequence $GGYRPGX_1SX_2$, wherein $X_1$ is an amino acid selected from A or G, and $X_2$ is an amino acid selected from V or I. SEQ ID NO:171 is represented by amino acid sequence $QSSQSVYDNNDLX_1$, wherein $X_1$ is an amino acid selected from A or G. SEQ ID NO:172 is represented by amino acid sequence $AGGYX_1GDIYT$, wherein $X_1$ is an amino acid selected from S or N. SEQ ID NO:173 is represented by amino acid sequence $X_1YAX_2D$, wherein $X_1$ is an amino acid selected from N or S, and $X_2$ is selected from M or I. SEQ ID NO:174 is represented by amino acid sequence $VIAPNX_1X_2TX_3YPTWARG$, wherein $X_1$ is an amino acid selected from R, G, or H; $X_2$ is an amino acid selected from R, A, or Y; and $X_3$ is an amino acid selected from Y or C. SEQ ID NO:175 is represented by amino acid sequence $YPIX_1X_2GX_3NI$, wherein $X_1$ is an amino acid selected from E or D; $X_2$ is an amino acid selected from P, A, S, or T; and $X_3$ is an amino acid selected from A or S. SEQ ID NO:176 is represented by amino acid sequence $QSSESVX_1X_2NNQLS$, wherein $X_1$ is an amino acid selected from D or G, and $X_2$ is an amino acid selected from Y, N, or M. SEQ ID NO:177 is represented by amino acid sequence $VIAPSX_1TTYYPTWAKG$, wherein $X_1$ is an amino acid selected from G or S. SEQ ID NO:178 is represented by amino acid sequence $YPIDPGSNX_1$, wherein $X_1$ is an amino acid selected from I or V. SEQ ID NO:179 is represented by amino acid sequence $X_1X_2AMD$, wherein $X_1$ is an amino acid selected from N or S, and $X_2$ is an amino acid selected from Y or H. SEQ ID NO:180 is represented by amino acid sequence $YPIDX_1GANV$, wherein $X_1$ is an amino acid selected from V or A.

Also provided are isolated monoclonal antibodies or antigen-binding fragments thereof comprising:

a. a heavy chain variable region having the polypeptide sequence of SEQ ID NO:1, and a light chain variable region having the polypeptide sequence of SEQ ID NO:2;

b. a heavy chain variable region having the polypeptide sequence of SEQ ID NO:3, and a light chain variable region having the polypeptide sequence of SEQ ID NO:4;
c. a heavy chain variable region having the polypeptide sequence of SEQ ID NO:5, and a light chain variable region having the polypeptide sequence of SEQ ID NO:6;
d. a heavy chain variable region having the polypeptide sequence of SEQ ID NO:7, and a light chain variable region having the polypeptide sequence of SEQ ID NO:8;
e. a heavy chain variable region having the polypeptide sequence of SEQ ID NO:9, and a light chain variable region having the polypeptide sequence of SEQ ID NO:10;
f. a heavy chain variable region having the polypeptide sequence of SEQ ID NO:11, and a light chain variable region having the polypeptide sequence of SEQ ID NO:12;
g. a heavy chain variable region having the polypeptide sequence of SEQ ID NO:13, and a light chain variable region having the polypeptide sequence of SEQ ID NO:14;
h. a heavy chain variable region having the polypeptide sequence of SEQ ID NO:15, and a light chain variable region having the polypeptide sequence of SEQ ID NO:16;
i. a heavy chain variable region having the polypeptide sequence of SEQ ID NO:17, and a light chain variable region having the polypeptide sequence of SEQ ID NO:18;
j. a heavy chain variable region having the polypeptide sequence of SEQ ID NO:19, and a light chain variable region having the polypeptide sequence of SEQ ID NO:20;
k. a heavy chain variable region having the polypeptide sequence of SEQ ID NO:21, and a light chain variable region having the polypeptide sequence of SEQ ID NO:22;
l. a heavy chain variable region having the polypeptide sequence of SEQ ID NO:23, and a light chain variable region having the polypeptide sequence of SEQ ID NO:24;
m. a heavy chain variable region having the polypeptide sequence of SEQ ID NO:25, and a light chain variable region having the polypeptide sequence of SEQ ID NO:26;
n. a heavy chain variable region having the polypeptide sequence of SEQ ID NO:27, and a light chain variable region having the polypeptide sequence of SEQ ID NO:28;
o. a heavy chain variable region having the polypeptide sequence of SEQ ID NO:29, and a light chain variable region having the polypeptide sequence of SEQ ID NO:30;
p. a heavy chain variable region having the polypeptide sequence of SEQ ID NO:31, and a light chain variable region having the polypeptide sequence of SEQ ID NO:32;
q. a heavy chain variable region having the polypeptide sequence of SEQ ID NO:33, and a light chain variable region having the polypeptide sequence of SEQ ID NO:34;
r. a heavy chain variable region having the polypeptide sequence of SEQ ID NO:35, and a light chain variable region having the polypeptide sequence of SEQ ID NO:36;
s. a heavy chain variable region having the polypeptide sequence of SEQ ID NO:37, and a light chain variable region having the polypeptide sequence of SEQ ID NO:38; or
t. a heavy chain variable region having the polypeptide sequence of SEQ ID NO:39, and a light chain variable region having the polypeptide sequence of SEQ ID NO:40.

Also provided are isolated monoclonal antibodies or antigen-binding fragments thereof to apelin that specifically bind to an epitope comprising the amino acid sequence of SEQ ID NO:188. The isolated monoclonal antibody or antigen-binding fragment thereof can, for example, inhibit apelin activity. The isolated monoclonal antibody or antigen-binding fragment thereof can, for example, specifically bind pyro-apelin-13, apelin-13, apelin-17, apelin-36, apelin-55, and/or other forms of apelin that share the same C-terminal end with apelin-13.

Also provided are isolated monoclonal antibodies or antigen-binding fragments thereof to apelin that specifically bind to an epitope comprising the amino acid sequence of SEQ ID NO:204. The isolated monoclonal antibody or antigen-binding fragment thereof can, for example, inhibit apelin activity. The isolated monoclonal antibody or antigen-binding fragment thereof can, for example, specifically bind apelin-13 and pyro-apelin-13.

In certain embodiments, the isolated monoclonal antibody or antigen-binding fragment thereof is chimeric.

In certain embodiments, the isolated monoclonal antibody or antigen-binding fragment thereof is human or humanized. In certain embodiments, the humanized monoclonal antibody or antigen-binding fragment thereof comprises:
a. a heavy chain variable region having the polypeptide sequence of SEQ ID NO:211, and a light chain variable region having the polypeptide sequence of SEQ ID NO:215;
b. a heavy chain variable region having the polypeptide sequence of SEQ ID NO:212, and a light chain variable region having the polypeptide sequence of SEQ ID NO:215;
c. a heavy chain variable region having the polypeptide sequence of SEQ ID NO:213, and a light chain variable region having the polypeptide sequence of SEQ ID NO:215;
d. a heavy chain variable region having the polypeptide sequence of SEQ ID NO:214, and a light chain variable region having the polypeptide sequence of SEQ ID NO:215;
e. a heavy chain variable region having the polypeptide sequence of SEQ ID NO:213, and a light chain variable region having the polypeptide sequence of SEQ ID NO:216;
f. a heavy chain variable region having the polypeptide sequence of SEQ ID NO:214, and a light chain variable region having the polypeptide sequence of SEQ ID NO:216;
g. a heavy chain variable region having the polypeptide sequence of SEQ ID NO:217, and a light chain variable region having the polypeptide sequence of SEQ ID NO:219; or h. a heavy chain variable region having the polypeptide sequence of SEQ ID NO:218, and a light chain variable region having the polypeptide sequence of SEQ ID NO:220.

Also provided are isolated nucleic acids encoding the monoclonal antibodies or antigen-binding fragment thereof of the invention disclosed herein.

Also provided are vectors comprising the isolated nucleic acids encoding the monoclonal antibodies or antigen-binding fragments thereof of the invention.

Also provided are host cells comprising the vectors comprising the isolated nucleic acids encoding the monoclonal antibodies or antigen-binding fragments thereof of the invention.

In certain embodiments, provided is a pharmaceutical composition comprising an isolated monoclonal antibody or antigen-binding fragment thereof of the invention and a pharmaceutically acceptable carrier.

Also provided are methods of blocking binding of apelin to an apelin receptor in a subject in need thereof, comprising administering to the subject the pharmaceutical compositions of the invention.

Also provided are methods of treating a diabetic retinopathy (DR) in a subject in need thereof, comprising administering to the subject the pharmaceutical compositions of the invention.

Also provided are methods of treating an age-related macular degeneration (AMD) in a subject in need thereof, comprising administering to the subject the pharmaceutical compositions of the invention.

Also provided are methods of treating a diabetic macular edema (DME) in a subject in need thereof, comprising administering to the subject the pharmaceutical compositions of the invention.

Also provided are methods of treating a macular edema following retinal vein occlusion (RVO) in a subject in need thereof, comprising administering to the subject the pharmaceutical compositions of the invention.

Also provided are methods of treating retinal degeneration in a subject in need thereof, comprising administering to the subject the pharmaceutical compositions of the invention.

Also provided are methods of treating myopic choroidal neovascularization (mCNV) in a subject in need thereof, comprising administering to the subject the pharmaceutical compositions of the invention.

Also provided are methods of treating a diabetic nephropathy in a subject in need thereof, comprising administering to the subject the pharmaceutical compositions of the invention.

Also provided are methods of treating a chronic kidney disease (CKD) in a subject in need thereof, comprising administering to the subject the pharmaceutical compositions of the invention.

Also provided are methods of treating a non-alcoholic steatohepatitis (NASH) in a subject in need thereof, comprising administering to the subject the pharmaceutical compositions of the invention.

Also provided are methods of treating a tissue fibrosis in a subject in need thereof, comprising administering to the subject the pharmaceutical compositions of the invention.

Also provided are methods of treating liver cirrhosis in a subject in need thereof, comprising administering to the subject the pharmaceutical compositions of the invention.

Also provided are methods of treating plaque neovascularization in a subject in need thereof, comprising administering to the subject the pharmaceutical compositions of the invention.

Also provided are methods of treating rubeosis iridis in a subject in need thereof, comprising administering to the subject the pharmaceutical compositions of the invention.

Also provided are methods of treating neovascular glaucoma in a subject in need thereof, comprising administering to the subject the pharmaceutical compositions of the invention.

Also provided are methods of treating corneal neovascularization (CNV) in a subject in need thereof, comprising administering to the subject the pharmaceutical compositions of the invention.

Also provided are methods of treating retinopathy of prematurity (ROP) in a subject in need thereof, comprising administering to the subject the pharmaceutical compositions of the invention.

Also provided are methods of treating retinopathy in a subject in need thereof, comprising administering to the subject the pharmaceutical compositions of the invention.

Also provided are methods of treating macular degeneration in a subject in need thereof, comprising administering to the subject the pharmaceutical compositions of the invention.

Also provided are methods of treating ovarian hyperstimulation syndrome (OHSS) in a subject in need thereof, comprising administering to the subject the pharmaceutical compositions of the invention.

Also provided are methods of treating uterine bleeding in a subject in need thereof, comprising administering to the subject the pharmaceutical compositions of the invention.

Also provided are methods of treating endometriosis in a subject in need thereof, comprising administering to the subject the pharmaceutical compositions of the invention.

Also provided are methods of treating endometrial hyperplasia and cancer in a subject in need thereof, comprising administering to the subject the pharmaceutical compositions of the invention.

Also provided are methods of treating myometrial leiomyomas in a subject in need thereof, comprising administering to the subject the pharmaceutical compositions of the invention.

Also provided are methods of treating adenomyosis in a subject in need thereof, comprising administering to the subject the pharmaceutical compositions of the invention.

Also provided are methods of treating cancer in a subject in need thereof, comprising administering to the subject the pharmaceutical compositions of the invention. The cancer can be any liquid or solid cancer, for example, it can be selected from but not limited to, a lung cancer, a gastric cancer, a colon cancer, a hepatocellular carcinoma, a renal cell carcinoma, a bladder urothelial carcinoma, a cholangiocarcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

In certain embodiments, the pharmaceutical composition further comprises a second therapeutic anti-cancer agent. The second therapeutic anti-cancer agent can, for example, be an anti-VEGF agent. The anti-VEGF agent can, for example, be Avastin® or a bevacizumab biosimilar agent. The anti-VEGF agent can, for example, be a VEGFR1 and/or VEGFR2 blocker.

Also provided are methods of determining a level of apelin in a subject. The methods comprise (a) obtaining a sample from the subject; (b) contacting the sample with an antibody or antigen-binding fragment thereof of the invention; and (c) determining a level of apelin in the subject. In certain embodiments, the sample is a tissue sample. The tissue sample can, for example, be a cancer tissue sample, a hepatic tissue sample, or a kidney tissue sample.

Also provided are methods of producing the monoclonal antibody or antigen-binding fragment thereof of the invention, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or culture.

Also provided are methods of producing a pharmaceutical composition comprising the monoclonal antibody or antigen-binding fragment thereof of the invention, comprising combining the monoclonal antibody or antigen-binding fragment with a pharmaceutically acceptable carrier to obtain the pharmaceutical composition.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 1A shows a graph demonstrating the binding of anti-apelin mAbs C5, C8, C17, C24, C25, C26, C27, C4 and C9 to various biotinylated apelin peptides as measured by ELISA. FIG. 1B shows a graph demonstrating the binding of anti-apelin mAbs C1, C6, C7, C10, C12, and C16 to various biotinylated apelin peptides as measured by ELISA. FIG. 1C shows a graph demonstrating the binding of anti-apelin mAbs C11, C14, C22, C20, and C13 to various biotinylated apelin peptides as measured by ELISA.

FIG. 2A shows a graph of the activity of the anti-apelin mAb C1. FIG. 2B shows a graph of the activity of the anti-apelin mAb C6. FIG. 2C shows a graph of the activity of the anti-apelin mAb C7. FIG. 2D shows a graph of the activity of the anti-apelin mAb C8. FIG. 2E shows a graph of the activity of the anti-apelin mAb C24. FIG. 2F shows a graph of the activity of the anti-apelin mAb C25. FIG. 2G shows a graph of the activity of the anti-apelin mAb C10. FIG. 2H shows a graph of the activity of the anti-apelin mAb C11. FIG. 2I shows a graph of the activity of the anti-apelin mAb C12. FIG. 2J shows a graph of the activity of the anti-apelin mAb C22. FIG. 2K shows a graph of the activity of the anti-apelin mAb C26.

FIG. 7A shows an IC50 graph when apelin 13 (APL13) was used in the assay. FIG. 7B shows an IC50 graph when pyro-apelin 13 (pyroAPL13) was used in the assay. CPS, counts per second.

DETAILED DESCRIPTION OF THE INVENTION

Figure 1A:
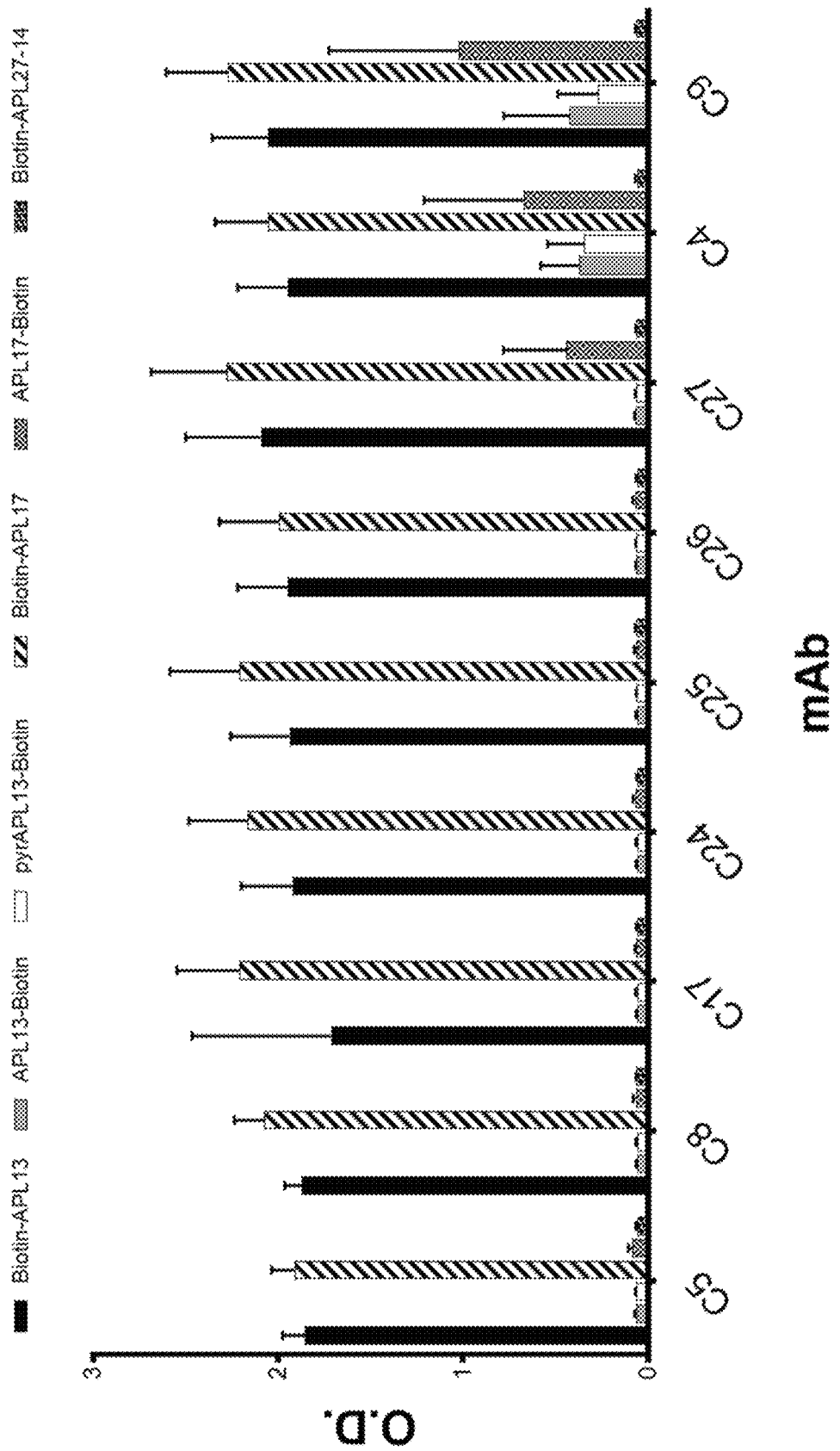
FIGS. 1A-1C show binding of anti-apelin mAbs to various biotinylated apelin peptides measured by ELISA. Biotinylated apelin peptides were immobilized on ELISA plates coated with neutravidin and purified recombinant rabbit anti-apelin mAbs were added for binding to the peptides on the plates. The binding was detected by adding a goat anti-rabbit IgG Fc-conjugated to alkaline phosphatase and PNPP substrate, and measured as the absorbance at 405 nm.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The words "right," "left," "lower," and "upper" designate directions in the drawings to which reference is made.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., anti-apelin antibodies, apelin polypeptides, and polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F.M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the terms "inhibit," "inhibiting," and "inhibition," mean to decrease an activity, response, condition, disease or other biological parameter. This can include, but is not limited to complete ablation of the activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels. By way of a non-limiting example, an antibody of the invention can inhibit the activity of an apelin protein. The activity of the apelin protein can be reduced or ablated relative to the native apelin protein activity.

Antibodies

The invention generally relates to isolated anti-apelin antibodies, nucleic acids and expression vectors encoding the antibodies, recombinant cells containing the vectors, and compositions comprising the antibodies. Methods of making the antibodies, and methods of using the antibodies to treat diseases including diabetic retinopathy (DR) (including proliferative diabetic retinopathy (PDR) and non-proliferative diabetic retinopathy (NPDR)), age-related macular degeneration (AMD), diabetic macular edema (DME), macular edema following retinal vein occlusion (RVO), retinal degeneration, myopic choroidal neovascularization (mCNV), diabetic nephropathy, chronic kidney disease (CKD), non-alcoholic steatohepatitis (NASH), liver cirrhosis, plaque neovascularization, rubeosis iridis, neovascular glaucoma, corneal neovascularization (CNV), retinopathy of prematurity (ROP), retinopathy, macular degeneration, ovarian hyperstimulation syndrome (OHSS), uterine bleeding, endometriosis, endometrial hyperplasia and cancer, myometrial leiomyomas, adenomyosis, cancer (e.g., solid tumors and hematologic malignancies), and fibrosis (e.g., pathological and physiological fibrosis, renal fibrosis, cardiac fibrosis, liver fibrosis, and pulmonary fibrosis), are also provided. The antibodies of the invention possess one or more desirable functional properties, including but not limited to high-affinity binding to apelin, high specificity to apelin, and the ability to block the binding of apelin to an apelin receptor.

In a general aspect, the invention relates to isolated monoclonal antibodies or antigen-binding fragments thereof that specifically bind apelin.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., complementarity determining regions 1-3; (CDR1, CDR2, and CDR3)). The light chain variable region domains are alternatively referred to as LCDR1, LCDR2, and LCDR3, and the heavy chain variable region domains are alternatively referred to as HCDR1, HCDR2, and HCDR3.

As used herein, the term an "isolated antibody" refers to an antibody which is substantially free of other antibodies having different antigenic specificities (e.g., an isolated antibody that specifically binds to apelin and is substantially free of antibodies that do not bind to apelin). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that can be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody, or a tetraspecific antibody molecule.

As used herein, the term "bispecifc antibody" refers to a multispecific antibody that binds no more than two epitopes or two antigens. A bispecific antibody is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment the first and second epitopes are on different antigens, e.g., the different proteins (or different subunits of a multimeric protein). In an embodiment a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on apelin and the second epitope is located on VEGF, Angiopoietin-2 (ANG-2), leucine-rich alpha-2-glycoprotein 1 (LRG1), PD-1, PD-L1, LAG-3, TIM-3, CTLA-4, HER-2, EGFR, CD19, CD73, CD47, CD20, CD33, DLL3, claudin18.2, TIP-1, CD3, PDGFβ, collagen type VI receptor, TGF-beta receptors, LOXL2, p75 neurotrophin receptor (NGFR p75), and/or Insulin-like growth factor 2 receptor (IGF2R). In certain embodiments, an anti-apelin monoclonal antibody or antigen-binding fragment thereof of the invention and an anti-VEGF antibody (e.g., Avastin® or a bevacizumab biosimilar agent) or antigen-binding fragment thereof are engineered to form a bispecific antibody that targets both apelin and VEGF.

As used herein, the term "apelin" refers to a 77 amino acid precursor protein, termed preproapelin, and its processed isoforms, which include apelin-13, apelin-16, apelin-17, apelin-36, apelin-55, and other forms derived from the 77-amino acid precursor. Each isoform has a distinct activity and acts by being a ligand for the apelin receptor APJ (also referred to as apelinR, AGTRL1, or APLNR), which is a class A, rhodopsin-like, G-protein coupled receptor (GPCR). The receptor binding affinities for apelin isoforms are different, which can account for different potencies in triggering intracellular signaling of the apelin receptor APJ. The apelin/APJ system plays important and various roles in the physiology and pathophysiology of many organs, including, but not limited to, regulation of blood pressure, cardiac contractility, cardiovascular tone, tissue angiogenesis, water homeostasis, gastrointestinal track physiology, metabolic balance, proliferation of vascular smooth muscle cell (VSMC) and other cell types, monocyte adhesion of human umbilical vein endothelial cells, cardiac repair post myocardial infarction, and pathological fibrosis in several tissues or organs. The term "human apelin" refers to a apelin originated from a human. An exemplary amino acid sequence of the precursor human apelin is represented in GenBank Accession No. AAF25815.1 (SEQ ID NO:221).

As used herein, an antibody that "specifically binds to apelin" refers to an antibody that binds to a apelin, preferably a human apelin, with a KD of $1 \times 10^{-7}$ M or less, preferably $1 \times 10^{-8}$ M or less, more preferably $5 \times 10^{-9}$ M or less, $1 \times 10^{-9}$ M or less, $5 \times 10^{-10}$ M or less, or $1 \times 10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as a Octet RED96 system.

The smaller the value of the KD of an antibody, the higher affinity that the antibody binds to a target antigen.

According to a particular aspect, the invention relates to an isolated monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of:

(1) SEQ ID NOs:168, 169, 170, 171, 102, and 172, respectively;
(2) SEQ ID NOs:50, 51, 52, 110, 111, and 112, respectively;
(3) SEQ ID NOs:173, 174, 175, 176, 114, and 115, respectively;
(4) SEQ ID NOs:68, 177, 178, 128, 129, and 130, respectively;
(5) SEQ ID NOs:74, 75, 76, 134, 135, and 136, respectively;
(6) SEQ ID NOs:179, 78, 180, 137, 138, and 139, respectively;
(7) SEQ ID NOs:83, 84, 85, 143, 144, and 145, respectively;
(8) SEQ ID NOs:86, 87, 88, 146, 147, and 148, respectively;
(9) SEQ ID NOs:89, 90, 91, 149, 150, and 151, respectively;
(10) SEQ ID NOs:92, 93, 94, 152, 153, and 154, respectively;
(11) SEQ ID NOs:95, 96, 97, 155, 156, and 157, respectively; or
(12) SEQ ID NOs:98, 99, 100, 158, 159, and 160, respectively;
wherein the antibody or antigen-binding fragment thereof specifically binds apelin, preferably human apelin.

SEQ ID NO:168 is represented by the amino acid sequence $X_1NRX_2S$, wherein $X_1$ is an amino acid selected from S or T, and $X_2$ is an amino acid selected from M or V.

SEQ ID NO:169 is represented by amino acid sequence $SIGSSPWX_1ASWAX_2G$, wherein $X_1$ is an amino acid selected from Y or F, and $X_2$ is selected from Q or L.

SEQ ID NO:170 is represented by amino acid sequence $GGYRPGX_1SX_2$, wherein $X_1$ is an amino acid selected from A or G, and $X_2$ is an amino acid selected from V or I.

SEQ ID NO:171 is represented by amino acid sequence $QSSQSVYDNNDLX_1$, wherein $X_1$ is an amino acid selected from A or G.

SEQ ID NO:172 is represented by amino acid sequence $AGGYX_1GDIYT$, wherein $X_1$ is an amino acid selected from S or N.

SEQ ID NO:173 is represented by amino acid sequence $X_1YAX_2D$, wherein $X_1$ is an amino acid selected from N or S, and $X_2$ is selected from M or I.

SEQ ID NO:174 is represented by amino acid sequence $VIAPNX_1X_2TX_3YPTWARG$, wherein $X_1$ is an amino acid selected from R, G, or H; $X_2$ is an amino acid selected from R, A, or Y; and $X_3$ is an amino acid selected from Y or C.

SEQ ID NO:175 is represented by amino acid sequence $YPIX_1X_2GX_3NI$, wherein $X_1$ is an amino acid selected from E or D; $X_2$ is an amino acid selected from P, A, S, or T; and $X_3$ is an amino acid selected from A or S.

SEQ ID NO:176 is represented by amino acid sequence $QSSESVX_1X_2NNQLS$, wherein $X_1$ is an amino acid selected from D or G, and $X_2$ is an amino acid selected from Y, N, or M.

SEQ ID NO:177 is represented by amino acid sequence $VIAPSX_1TTYYPTWAKG$, wherein $X_1$ is an amino acid selected from G or S.

SEQ ID NO:178 is represented by amino acid sequence $YPIDPGSNX_1$, wherein $X_1$ is an amino acid selected from I or V.

SEQ ID NO:179 is represented by amino acid sequence $X_1X_2AMD$, wherein $X_1$ is an amino acid selected from N or S, and $X_2$ is an amino acid selected from Y or H.

SEQ ID NO:180 is represented by amino acid sequence $YPIDX_1GANV$, wherein $X_1$ is an amino acid selected from V or A.

According to another particular aspect, the invention relates to an isolated monoclonal antibody or antigen-binding fragment thereof comprising a heavy chain variable region having a polypeptide sequence at least 85%, preferably 90%, more preferably 95% identical to one of SEQ ID NOs:1, 3, 5, 7, 9, 11, 13, 15, 17, 19, 21, 23, 25, 27, 29, 31, 33, 35, 37, or 39, or a light chain variable region having a polypeptide sequence at least 85%, preferably 90%, more preferably 95% identical to one of SEQ ID NOs:2, 4, 6, 8, 10, 12, 14, 16, 18, 20, 22, 24, 26, 28, 30, 32, 34, 36, 38, or 40. According to one preferred embodiment, the isolated monoclonal antibody or antigen-binding fragment thereof of the invention comprises a heavy chain variable region having the polypeptide sequence at least 85%, preferably 90%, more preferably 95% identical to SEQ ID NO:1, 3, 5, 7, 9, 11, 13, 15, 17, 19, 21, 23, 25, 27, 29, 31, 33, 35, 37, or 39, and a light chain variable region having a polypeptide sequence at least 85%, preferably 90%, more preferably 95% identical to SEQ ID NO:2, 4, 6, 8, 10, 12, 14, 16, 18, 20, 22, 24, 26, 28, 30, 32, 34, 36, 38, or 40, respectively.

According to another particular aspect, the invention relates to an isolated monoclonal antibody or antigen-binding fragment thereof of the invention, comprising:
- a. a heavy chain variable region having the polypeptide sequence of SEQ ID NO:1, and a light chain variable region having the polypeptide sequence of SEQ ID NO:2;
- b. a heavy chain variable region having the polypeptide sequence of SEQ ID NO:3, and a light chain variable region having the polypeptide sequence of SEQ ID NO:4;
- c. a heavy chain variable region having the polypeptide sequence of SEQ ID NO:5, and a light chain variable region having the polypeptide sequence of SEQ ID NO:6;
- d. a heavy chain variable region having the polypeptide sequence of SEQ ID NO:7, and a light chain variable region having the polypeptide sequence of SEQ ID NO:8;
- e. a heavy chain variable region having the polypeptide sequence of SEQ ID NO:9, and a light chain variable region having the polypeptide sequence of SEQ ID NO:10;
- f. a heavy chain variable region having the polypeptide sequence of SEQ ID NO:11, and a light chain variable region having the polypeptide sequence of SEQ ID NO:12;
- g. a heavy chain variable region having the polypeptide sequence of SEQ ID NO:13, and a light chain variable region having the polypeptide sequence of SEQ ID NO:14;
- h. a heavy chain variable region having the polypeptide sequence of SEQ ID NO:15, and a light chain variable region having the polypeptide sequence of SEQ ID NO:16;
- i. a heavy chain variable region having the polypeptide sequence of SEQ ID NO:17, and a light chain variable region having the polypeptide sequence of SEQ ID NO:18;
- j. a heavy chain variable region having the polypeptide sequence of SEQ ID NO:19, and a light chain variable region having the polypeptide sequence of SEQ ID NO:20;
- k. a heavy chain variable region having the polypeptide sequence of SEQ ID NO:21, and a light chain variable region having the polypeptide sequence of SEQ ID NO:22;
- l. a heavy chain variable region having the polypeptide sequence of SEQ ID NO:23, and a light chain variable region having the polypeptide sequence of SEQ ID NO:24;
- m. a heavy chain variable region having the polypeptide sequence of SEQ ID NO:25, and a light chain variable region having the polypeptide sequence of SEQ ID NO:26;
- n. a heavy chain variable region having the polypeptide sequence of SEQ ID NO:27, and a light chain variable region having the polypeptide sequence of SEQ ID NO:28;
- o. a heavy chain variable region having the polypeptide sequence of SEQ ID NO:29, and a light chain variable region having the polypeptide sequence of SEQ ID NO:30;
- p. a heavy chain variable region having the polypeptide sequence of SEQ ID NO:31, and a light chain variable region having the polypeptide sequence of SEQ ID NO:32;
- q. a heavy chain variable region having the polypeptide sequence of SEQ ID NO:33, and a light chain variable region having the polypeptide sequence of SEQ ID NO:34;
- r. a heavy chain variable region having the polypeptide sequence of SEQ ID NO:35, and a light chain variable region having the polypeptide sequence of SEQ ID NO:36;
- s. a heavy chain variable region having the polypeptide sequence of SEQ ID NO:37, and a light chain variable region having the polypeptide sequence of SEQ ID NO:38; or
- t. a heavy chain variable region having the polypeptide sequence of SEQ ID NO:39, and a light chain variable region having the polypeptide sequence of SEQ ID NO:40.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:41, 42, 43, 101, 102, and 103, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:1, and a light chain variable region having a polypeptide sequence at least 85%, preferably 90%, more preferably 95% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:44, 45, 46, 104, 105, and 106, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:3, and a light chain variable region having a polypeptide sequence at least 85%, preferably 90%, more preferably 95% identical to SEQ ID NO:4. Preferably, the isolated monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:47, 48, 49, 107, 108, and 109, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:5, and a light chain variable region having a polypeptide sequence at least 85%, preferably 90%, more preferably 95% identical to SEQ ID NO:6. Preferably, the isolated monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:50, 51, 52, 110, 111, and 112, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:7, and a light chain variable region having a polypeptide sequence at least 85%, preferably 90%, more preferably 95% identical to SEQ ID NO:8. Preferably, the isolated monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:53, 54, 55, 113, 114, and 115, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:9, and a light chain variable region having a polypeptide sequence at least 85%, preferably 90%, more preferably 95% identical to SEQ ID NO:10. Preferably, the isolated monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:56, 57, 58, 116, 117, and 118, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:11, and a light chain variable region having a polypeptide sequence at least 85%, preferably 90%, more preferably 95% identical to SEQ ID NO:12. Preferably, the isolated monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:59, 60, 61, 119, 120, and 121, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:13, and a light chain variable region having a polypeptide sequence at least 85%, preferably 90%, more preferably 95% identical to SEQ ID NO:14. Preferably, the isolated monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:62, 63, 64, 122, 123, and 124, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:15, and a light chain variable region having a polypeptide sequence at least 85%, preferably 90%, more preferably 95% identical to SEQ ID NO:16. Preferably, the isolated monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:65, 66, 67, 125, 126, and 127, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:17, and a light chain variable region having a polypeptide sequence at least 85%, preferably 90%, more preferably 95% identical to SEQ ID NO:18. Preferably, the isolated monoclonal antibody or antigen-binding fragment thereof comprises a heavy chain variable region having the polypeptide sequence of SEQ ID NO:17; and a light chain variable region having the polypeptide sequence of SEQ ID NO:18.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:68, 69, 70, 128, 129, and 130, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:19, and a light chain variable region having a polypeptide sequence at least 85%, preferably 90%, more preferably 95% identical to SEQ ID NO:20. Preferably, the isolated monoclonal antibody or antigen-binding fragment thereof comprises a heavy chain variable region having the polypeptide sequence of SEQ ID NO:19; and a light chain variable region having the polypeptide sequence of SEQ ID NO:20.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:71, 72, 73, 131, 132, and 133, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:21, and a light chain variable region having a polypeptide sequence at least 85%, preferably 90%, more preferably 95% identical to SEQ ID NO:22. Preferably, the isolated monoclonal antibody or antigen-binding fragment thereof comprises a heavy chain variable region having the polypeptide sequence of SEQ ID NO:21; and a light chain variable region having the polypeptide sequence of SEQ ID NO:22.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:74, 75, 76, 134, 135, and 136, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:23, and a light chain variable region having a polypeptide sequence at least 85%, preferably 90%, more preferably 95% identical to SEQ ID NO:24. Preferably, the isolated monoclonal antibody or antigen-binding fragment thereof comprises a heavy chain variable region having the polypeptide sequence of SEQ ID NO:23; and a light chain variable region having the polypeptide sequence of SEQ ID NO:24.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:77, 78, 79, 137, 138, and 139, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:25, and a light chain variable region having a polypeptide sequence at least 85%, preferably 90%, more preferably 95% identical to SEQ ID NO:26. Preferably, the isolated monoclonal antibody or antigen-binding fragment thereof comprises a heavy chain variable region having the polypeptide sequence of SEQ ID NO:25; and a light chain variable region having the polypeptide sequence of SEQ ID NO:26.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:80, 81, 82, 140, 141, and 142, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:27, and a light chain variable region having a polypeptide sequence at least 85%, preferably 90%, more preferably 95% identical to SEQ ID NO:28. Preferably, the isolated monoclonal antibody or antigen-binding fragment thereof comprises a heavy chain variable region having the polypeptide sequence of SEQ ID NO:27; and a light chain variable region having the polypeptide sequence of SEQ ID NO:28.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:83, 84, 85, 143, 144, and 145, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:29, and a light chain variable region having a polypeptide sequence at least 85%, preferably 90%, more preferably 95% identical to SEQ ID NO:30. Preferably, the isolated monoclonal antibody or antigen-binding fragment thereof comprises a heavy chain variable region having the polypeptide sequence of SEQ ID NO:29; and a light chain variable region having the polypeptide sequence of SEQ ID NO:30.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:86, 87, 88, 146, 147, and 148, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:31, and a light chain variable region having a polypeptide sequence at least 85%, preferably 90%, more preferably 95% identical to SEQ ID NO:32. Preferably, the isolated monoclonal antibody or antigen-binding fragment thereof comprises a heavy chain variable region having the polypeptide sequence of SEQ ID NO:31; and a light chain variable region having the polypeptide sequence of SEQ ID NO:32.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:89, 90, 91, 149, 150, and 151, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:33, and a light chain variable region having a polypeptide sequence at least 85%, preferably 90%, more preferably 95% identical to SEQ ID NO:34. Preferably, the isolated monoclonal antibody or antigen-binding fragment thereof comprises a heavy chain variable region having the polypeptide sequence of SEQ ID NO:33; and a light chain variable region having the polypeptide sequence of SEQ ID NO:34.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:92, 93, 94, 152, 153, and 154, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:35, and a light chain variable region having a polypeptide sequence at least 85%, preferably 90%, more preferably 95% identical to SEQ ID NO:36. Preferably, the isolated monoclonal antibody or antigen-binding fragment thereof comprises a heavy chain variable region having the polypeptide sequence of SEQ ID NO:35; and a light chain variable region having the polypeptide sequence of SEQ ID NO:36.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:95, 96, 97, 155, 156, and 157, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:37, and a light chain variable region having a polypeptide sequence at least 85%, preferably 90%, more preferably 95% identical to SEQ ID NO:38. Preferably, the isolated monoclonal antibody or antigen-binding fragment thereof comprises a heavy chain variable region having the polypeptide sequence of SEQ ID NO:37; and a light chain variable region having the polypeptide sequence of SEQ ID NO:38.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:98, 99, 100, 158, 159, and 160, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO:39, and a light chain variable region having a polypeptide sequence at least 85%, preferably 90%, more preferably 95% identical to SEQ ID NO:40. Preferably, the isolated monoclonal antibody or antigen-binding fragment thereof comprises a heavy chain variable region having the polypeptide sequence of SEQ ID NO:39; and a light chain variable region having the polypeptide sequence of SEQ ID NO:40.

According to another particular aspect, the invention relates to an isolated monoclonal antibody or antigen-binding fragment thereof to apelin that specifically binds to an epitope comprising the amino acid sequence of SEQ ID NO:188. The isolated monoclonal antibody or antigen-binding fragment thereof can, for example, inhibit apelin activity. The monoclonal antibody or antigen-binding fragment thereof can, for example, specifically bind pyro-apelin-13, apelin-13, apelin-17, apelin-36, apelin-55, and/or other forms of apelin that share the same C-terminal end with apelin-13.

According to another particular aspect, the invention relates to an isolated monoclonal antibody or antigen-binding fragment thereof to apelin that specifically binds to an epitope comprising the amino acid sequence of SEQ ID NO:204. The isolated monoclonal antibody or antigen-binding fragment thereof can, for example, inhibit apelin activity. The monoclonal antibody or antigen-binding fragment thereof can, for example, specifically bind apelin-13 and/or pyro-apelin-13.

According to another particular aspect, the invention relates to an isolated monoclonal antibody or antigen-binding fragment thereof of the invention, wherein the antibody or antigen-binding fragment thereof is chimeric.

According to another particular aspect, the invention relates to an isolated monoclonal antibody or antigen-binding fragment thereof of the invention, wherein the antibody or antigen-binding fragment thereof is human or humanized.

According to another particular aspect, the invention relates to an isolated humanized monoclonal antibody or antigen-binding fragment, wherein the isolated humanized antibody or antigen-binding fragment thereof comprises:

a. a heavy chain variable region having the polypeptide sequence of SEQ ID NO:211, and a light chain variable region having the polypeptide sequence of SEQ ID NO:215;

b. a heavy chain variable region having the polypeptide sequence of SEQ ID NO:212, and a light chain variable region having the polypeptide sequence of SEQ ID NO:215;

c. a heavy chain variable region having the polypeptide sequence of SEQ ID NO:213, and a light chain variable region having the polypeptide sequence of SEQ ID NO:215;

d. a heavy chain variable region having the polypeptide sequence of SEQ ID NO:214, and a light chain variable region having the polypeptide sequence of SEQ ID NO:215;

e. a heavy chain variable region having the polypeptide sequence of SEQ ID NO:213, and a light chain variable region having the polypeptide sequence of SEQ ID NO:216;

f. a heavy chain variable region having the polypeptide sequence of SEQ ID NO:214, and a light chain variable region having the polypeptide sequence of SEQ ID NO:216;

g. a heavy chain variable region having the polypeptide sequence of SEQ ID NO:217, and a light chain variable region having the polypeptide sequence of SEQ ID NO:219; or h. a heavy chain variable region having the polypeptide sequence of SEQ ID NO:218, and a light chain variable region having the polypeptide sequence of SEQ ID NO:220.

In another general aspect, the invention relates to an isolated nucleic acid encoding a monoclonal antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies or antigen-binding fragments thereof of the invention can be altered without changing the amino acid sequences of the proteins.

In another general aspect, the invention relates to a vector comprising an isolated nucleic acid encoding a monoclonal antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention.

In another general aspect, the invention relates to a host cell comprising an isolated nucleic acid encoding a monoclonal antibody or antigen-binding fragment thereof of the invention. Any host cell known to those skilled in the art in view of the present disclosure can be used for recombinant expression of antibodies or antigen-binding fragments thereof of the invention. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a monoclonal antibody or antigen-binding fragment thereof of the invention, comprising culturing a cell comprising a nucleic acid encoding the monoclonal antibody or antigen-binding fragment thereof under conditions to produce a monoclonal antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Pharmaceutical Compositions

In another general aspect, the invention relates to a pharmaceutical composition, comprising an isolated monoclonal antibody or antigen-binding fragment thereof of the invention and a pharmaceutically acceptable carrier. The term "pharmaceutical composition" as used herein means a product comprising an antibody of the invention together with a pharmaceutically acceptable carrier. Antibodies of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carriers can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, intravitreally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the embodiment include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars can be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments of the invention.

In another general aspect, the invention relates to a method of producing a pharmaceutical composition comprising a monoclonal antibody or antigen-binding fragment thereof of the invention, comprising combining a monoclonal antibody or antigen-binding fragment thereof with a pharmaceutically acceptable carrier to obtain the pharmaceutical composition.

Methods of Use

In another general aspect, the invention relates to a method of blocking the binding of apelin to an apelin receptor, the method comprising administering to the subject a pharmaceutical composition of the invention.

The functional activity of antibodies and antigen-binding fragments thereof that bind apelin can be characterized by methods known in the art and as described herein. Methods for characterizing antibodies and antigen-binding fragments thereof that bind apelin include, but are not limited to, affinity and specificity assays including Biacore, ELISA, and OctetRed analysis; receptor ligand binding assays to detect blocking of the binding of apelin to an apelin receptor; cell-based assays to detect neutralizing activity of a mAb on apelin-stimulated intracellular signaling. According to particular embodiments, the methods for characterizing antibodies and antigen-binding fragments thereof that bind apelin include those described below.

In another general aspect, the invention relates to a method of treating a diabetic retinopathy (DR) in a subject in need thereof, comprising administering to the subject a pharmaceutical composition of the invention.

In another general aspect, the invention relates to a method of treating an age-related macular degeneration (AMD) in a subject in need thereof, comprising administering to the subject a pharmaceutical composition of the invention.

In another general aspect, the invention relates to a method of treating a diabetic macular edema (DME) in a subject in need thereof, comprising administering to the subject a pharmaceutical composition of the invention.

In another general aspect, the invention relates to a method of treating a macular edema following retinal vein occlusion (RVO) in a subject in need thereof, comprising administering to the subject a pharmaceutical composition of the invention.

In another general aspect, the invention relates to a method of treating a retinal degeneration in a subject in need thereof, comprising administering to the subject a pharmaceutical composition of the invention.

In another general aspect, the invention relates to a method of a myopic choroidal neovascularization (mCNV) in a subject in need thereof, comprising administering to the subject a pharmaceutical composition of the invention.

In another general aspect, the invention relates to a method of treating a diabetic nephropathy in a subject in need thereof, comprising administering to the subject a pharmaceutical composition of the invention.

In another general aspect, the invention relates to a method of treating a chronic kidney disease (CKD) in a subject in need thereof, comprising administering to the subject a pharmaceutical composition of the invention.

In another general aspect, the invention relates to a method of treating a non-alcoholic steatohepatitis (NASH) in a subject in need thereof, comprising administering to the subject a pharmaceutical composition of the invention.

In another general aspect, the invention relates to a method of treating liver cirrhosis in a subject in need thereof, comprising administering to the subject a pharmaceutical composition of the invention.

In another general aspect, the invention relates to a method of treating plaque neovascularization in a subject in need thereof, comprising administering to the subject a pharmaceutical composition of the invention.

In another general aspect, the invention relates to a method of treating rubeosis iridis in a subject in need thereof, comprising administering to the subject a pharmaceutical composition of the invention.

In another general aspect, the invention relates to a method of treating neovascular glaucoma in a subject in need thereof, comprising administering to the subject a pharmaceutical composition of the invention.

In another general aspect, the invention relates to a method of treating corneal neovascularization (CNV) in a subject in need thereof, comprising administering to the subject a pharmaceutical composition of the invention.

In another general aspect, the invention relates to a method of treating retinopathy of prematurity (ROP) in a subject in need thereof, comprising administering to the subject a pharmaceutical composition of the invention.

In another general aspect, the invention relates to a method of treating retinopathy in a subject in need thereof, comprising administering to the subject a pharmaceutical composition of the invention.

In another general aspect, the invention relates to a method of treating macular degeneration in a subject in need thereof, comprising administering to the subject a pharmaceutical composition of the invention.

In another general aspect, the invention relates to a method of treating ovarian hyperstimulation syndrome (OHSS) in a subject in need thereof, comprising administering to the subject a pharmaceutical composition of the invention.

In another general aspect, the invention relates to a method of treating uterine bleeding in a subject in need thereof, comprising administering to the subject a pharmaceutical composition of the invention.

In another general aspect, the invention relates to a method of treating endometriosis in a subject in need thereof, comprising administering to the subject a pharmaceutical composition of the invention.

In another general aspect, the invention relates to a method of treating endometrial hyperplasia and cancer in a subject in need thereof, comprising administering to the subject a pharmaceutical composition of the invention.

In another general aspect, the invention relates to a method of treating myometrial leiomyomas in a subject in need thereof, comprising administering to a subject the pharmaceutical composition of the invention.

In another general aspect, the invention relates to a method of treating adenomyosis in a subject in need thereof, comprising administering to the subject a pharmaceutical composition of the invention.

In another general aspect, the invention relates to a method of treating a fibrosis in a subject in need thereof, comprising administering to the subject a pharmaceutical composition of the invention. The fibrosis can, for example, be selected from a pathological and physiological fibrosis, a renal fibrosis, a cardiac fibrosis, a liver fibrosis, or a pulmonary fibrosis.

In another general aspect, the invention relates to a method of treating a cancer in a subject in need thereof, comprising administering to the subject a pharmaceutical composition of the invention. The cancer can be any liquid or solid cancer, for example, it can be selected from but not limited to, a lung cancer, a gastric cancer, a colon cancer, a hepatocellular carcinoma, a renal cell carcinoma, a bladder urothelial carcinoma, a cholangiocarcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

In certain embodiments, the pharmaceutical composition further comprises a second therapeutic anti-cancer agent. The second therapeutic anti-cancer agent can, for example be an anti-VEGF agent. The anti-VEGF agent can, for example, be Avastin® or a bevacizumab biosimilar agent. The anti-VEGF agent can, for example, be a VEGFR1 and/or VEFR2 blocker. In certain embodiments, the anti-apelin monoclonal antibody or antigen-binding fragment thereof and the second therapeutic anti-cancer agent are co-administered in separate formulations. In certain embodiments, the anti-apelin monoclonal antibody or antigen-binding fragment thereof and the second therapeutic anti-cancer agent are co-administered in a single formulation. In certain embodiments, the anti-apelin monoclonal antibody or antigen-binding fragment thereof and the second therapeutic anti-cancer agent, e.g., the anti-VEGF agent, such as Avastin®, are engineered to be a bispecifc antibody that targets both VEGF and apelin.

According to embodiments of the invention, the pharmaceutical composition comprises a therapeutically effective amount of the anti-apelin antibody or antigen-binding fragment thereof. As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein with reference to anti-apelin antibodies or antigen-binding fragments thereof, a therapeutically effective amount means an amount of the anti-apelin antibody or antigen-binding fragment thereof that modulates an immune response in a subject in need thereof. Also as used herein with reference to anti-apelin antibodies or antigen-binding fragments thereof, a therapeutically effective amount means an amount of the anti-apelin antibody or antigen-binding fragment thereof that results in treatment of a disease, disorder, or condition; prevents or slows the progression of the disease, disorder, or condition; or reduces or completely alleviates symptoms associated with the disease, disorder, or condition.

According to particular embodiments, the disease, disorder or condition to be treated is a diabetic retinopathy (DR), an age-related macular degeneration (AMD), a diabetic macular edema (DME), a macular edema following retinal vein occlusion (RVO), a retinal degeneration, a myopic choroidal neovascularization (mCNV), a diabetic nephropathy, a chronic kidney disease (CKD), a non-alcoholic steatohepatitis (NASH), a liver cirrhosis, a plaque neovascularization, a rubeosis iridis, a neovascular glaucoma, a corneal neovascularization (CNV), a retinopathy of prematurity (ROP), a retinopathy, a macular degeneration, an ovarian hyperstimulation syndrome (OHSS), a uterine bleeding, an endometriosis, an endometrial hyperplasia and cancer, a myometrial leiomyomas, an adenomyosis, a fibrosis (e.g., a pathological and physiological fibrosis, a renal fibrosis, a cardiac fibrosis, a liver fibrosis, and a pulmonary fibrosis), and/or associated complications. According to other particular embodiments, the disease, disorder or condition to be treated is cancer, preferably a cancer selected from the group consisting of lung cancer, gastric cancer, colon cancer, hepatocellular carcinoma, renal cell carcinoma, bladder urothelial carcinoma, cholangiocarcinoma, metastatic melanoma, breast cancer, ovarian cancer, cervical cancer, head and neck cancer, pancreatic cancer, glioma, glioblastoma, and other solid tumors, and non-Hodgkin's lymphoma (NHL), acute lymphocytic leukemia (ALL), chronic lymphocytic leukemia (CLL), chronic myelogenous leukemia (CML), multiple myeloma (MM), acute myeloid leukemia (AML), and other liquid tumors.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer, a diabetic retinopathy (DR) disease, disorder or condition, an age-related macular degeneration (AMD) disease, disorder or condition, a diabetic macular edema (DME) disease, disorder or condition, a macular edema following retinal vein occlusion (RVO) disease, disorder or condition, a retinal degeneration disease, disorder or condition, a myopic choroidal neovascularization (mCNV) disease, disorder or condition, a diabetic nephropathy disease, disorder or condition, a chronic kidney disease (CKD), disorder or condition, a non-alcoholic steatohepatitis (NASH) disease, disorder or condition, a liver cirrhosis disease, disorder or condition, a plaque neovascularization disease, disorder or condition, a rubeosis iridis disease, disorder or condition, a neovascular glaucoma disease, disorder or condition, a corneal neovascularization (CNV) disease, disorder or condition, a retinopathy of prematurity (ROP) disease, disorder or condition, a retinopathy disease, disorder or condition, a macular degeneration disease, disorder or condition, an ovarian hyperstimulation syndrome (OHSS) disease, disorder or condition, a uterine bleeding disease, disorder or condition, an endometriosis disease, disorder or condition, an endometrial hyperplasia and cancer disease, disorder or condition, a myometrial leiomyomas disease, disorder or condition, an adenomyosis disease, disorder or condition, and/or a fibrosis disease, disorder or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, a composition used in the treatment of a cancer, a diabetic retinopathy (DR) disease, disorder or condition, an age-related macular degeneration (AMD) disease, disorder or condition, a diabetic macular edema (DME) disease, disorder or condition, a macular edema following retinal vein occlusion (RVO) disease, disorder or condition, a retinal degeneration disease, disorder or condition, a myopic choroidal neovascularization (mCNV) disease, disorder or condition, a diabetic nephropathy disease, disorder or condition, a chronic kidney disease (CKD), disorder or condition, a non-alcoholic steatohepatitis (NASH) disease, disorder or condition, a liver cirrhosis disease, disorder or condition, a plaque neovascularization disease, disorder or condition, a rubeosis iridis disease, disorder or condition, a neovascular glaucoma disease, disorder or condition, a corneal neovascularization (CNV) disease, disorder or condition, a retinopathy of prematurity (ROP) disease, disorder or condition, a retinopathy disease, disorder or condition, a macular degeneration disease, disorder or condition, an ovarian hyperstimulation syndrome (OHSS) disease, disorder or condition, a uterine bleeding disease, disorder or condition, an endometriosis disease, disorder or condition, an endometrial hyperplasia and cancer disease, disorder or condition, a myometrial leiomyomas disease, disorder or condition, an adenomyosis disease, disorder or condition, and/or a fibrosis disease, disorder or condition, can be used in combination with another treatment. For cancer treatment, the composition can be used in combination with another treatment including, but not limited to, a chemotherapy, a therapy that blocks the VEGF/VEGFR1/VEGFR2 axis such as AVASTIN®, an anti-CD20 mAb, an anti-CTLA-4 antibody, an anti-LAG-3 mAb, an anti-EGFR mAb, an anti-HER-2 mAb, an anti-CD19 mAb, an anti-CD33 mAb, an anti-CD73 mAb, an anti-CD47 mAb, an anti-DLL-3 mAb, an anti-apelin mAb, an anti-TIP-1 mAb, an anti-CLDN18.2 mAb, an anti-FOLR1 mAb, an anti-PD-L1 antibody, an anti-PD-1 antibody, a PD-1/PD-L1 therapy, or other immuno-oncology drugs, a targeted therapy, an antiangiogenic agent, a radiation therapy, or other anticancer drugs. Anti-apelin antibodies can be used to construct bispecific antibodies with partner mAbs against VEGF, angiopoietin-2 (ANG-2), leucine-rich alpha-2-glycoprotein 1 (LRG1), CD73, PD-1, PD-L1, LAG-3, TIM-3, CTLA-4, EGFR, HER-2, CD19, CD20, CD33, CD47, DLL3, claudin18.2, TIP-1, CD3, PDGFβ, collagen type VI receptor, TGF-beta receptors, LOXL2, p75 neurotrophin receptor (NGFR p'75), Insulin-like growth factor 2 receptor (IGF2R), and/or other mAbs to tumor surface antigens to treat cancers/tumors. For treatment of a diabetic retinopathy (DR), an age-related macular degeneration (AMD), and/or a diabetic macular edema (DME), the composition can be used in combination with another treatment including, but not limited to a VEGF blocker (e.g., ranibizumab (LUCENTIS®), aflibercept (EYLEA®, conbercept) or another anti-DR, anti-AMD, and/or anti-DME drug. Anti-apelin antibodies can be used to construct bispecific antibodies with partner mAbs against VEGF, ANG-2, and/or other mAbs to DR, AMD, and/or DME specific antigens to treat DR, AMD, and/or DME that express both apelin and the specific DR, AMD, and/or DME antigen.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a method of determining a level of apelin in a subject. The methods comprise (a) obtaining a sample from the subject; (b) contacting the sample with an antibody or antigen-binding fragment thereof of the invention; and (c) determining a level of apelin in the subject.

As used herein, "sample" refers to a biological sample isolated from a subject and can include, but is not limited to, whole blood, serum, plasma, blood cells, endothelial cells, tissue biopsies (e.g., a cancer tissue, a hepatic tissue, etc.), lymphatic fluid, ascites fluid, interstitial fluid, bone marrow, cerebrospinal fluid, saliva, mucous, sputum, sweat, urine, or any other secretion, excretion, or other bodily fluids. A "blood sample" refers to whole blood or any fraction thereof, including blood cells, serum, and plasma.

In certain embodiments, the level of apelin in the subject can be determined utilizing assays selected from, but not limited to, a Western blot assay, an ELISA assay, and/or a radioimmunoassay (RIA). Relative protein levels can be determined by utilizing Western blot analysis and immunohistochemistry (IHC), and absolute protein levels can be determined by utilizing an ELISA assay or a RIA assay. When determining the relative levels of apelin, the levels of apelin can be determined between at least two samples, e.g., between samples from the same subject at different time points, between samples from different tissues in the same subject, and/or between samples from different subjects. Alternatively, when determining absolute levels of apelin, such as by an ELISA assay, the absolute level of apelin in the sample can be determined by creating a standard for the ELISA assay prior to testing the sample, and when utilizing a RIA assay, the absolute level of apelin in the sample can be determined by mixing the sample with radiolabeled apelin and a known amount of the antibodies or antigen-binding fragments thereof of the invention to allow them to bind, separating the bound apelin (including the radiolabeled and native ones) from the free (unbound) ones (also including the radiolabeled and native ones), and measuring the radioactivity of the free (unbound) apelin. A person skilled in the art would understand which analytical techniques to utilize to determine the level of apelin in a sample from the subject utilizing the antibodies or antigen-binding fragments thereof of the invention.

Utilizing methods of determining a level of apelin in a sample from a subject can lead to the diagnosis of abnormal (elevated, reduced, or insufficient) apelin levels in a disease and making appropriate therapeutic decisions. Such a disease can be selected from, but not limited to, a cardiovascular disease, a heart failure, a diabetes, an obesity, a diabetic retinopathy (DR), an age-related macular degeneration (AMD), a diabetic macular edema (DME), a macular edema following retinal vein occlusion (RVO), a retinal degeneration, a myopic choroidal neovascularization (mCNV), a diabetic nephropathy, a chronic kidney disease (CKD), a non-alcoholic steatohepatitis (NASH), a liver cirrhosis, a plaque neovascularization, a rubeosis iridis, a neovascular glaucoma, a corneal neovascularization (CNV), a retinopathy of prematurity (ROP), a retinopathy, a macular degeneration, an ovarian hyperstimulation syndrome (OHSS), a uterine bleeding, an endometriosis, an endometrial hyperplasia and cancer, a myometrial leiomyomas, an adenomyosis, a fibrosis (e.g., a pathological and physiological fibrosis, a renal fibrosis, a cardiac fibrosis, a liver fibrosis, and a pulmonary fibrosis), and/or a cancer. Additionally, by monitoring the levels of apelin in a subject, the risk of developing a disease as indicated above can be determined based on the knowledge of the level of apelin in a particular disease and/or during the progression of the particular disease.

EMBODIMENTS

The invention provides also the following non-limiting embodiments.

Embodiment 1 is an isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequences of:

(1) SEQ ID NOs:168, 169, 170, 171, 102, and 172, respectively;

(2) SEQ ID NOs:50, 51, 52, 110, 111, and 112, respectively;

(3) SEQ ID NOs:173, 174, 175, 176, 114, and 115, respectively;

(4) SEQ ID NOs:68, 177, 178, 128, 129, and 130, respectively;

(5) SEQ ID NOs:74, 75, 76, 134, 135, and 136, respectively;

(6) SEQ ID NOs:179, 78, 180, 137, 138, and 139, respectively;

(7) SEQ ID NOs:83, 84, 85, 143, 144, and 145, respectively;

(8) SEQ ID NOs:86, 87, 88, 146, 147, and 148, respectively;

(9) SEQ ID NOs:89, 90, 91, 149, 150, and 151, respectively;

(10) SEQ ID NOs:92, 93, 94, 152, 153, and 154, respectively;

(11) SEQ ID NOs:95, 96, 97, 155, 156, and 157, respectively; or

(12) SEQ ID NOs:98, 99, 100, 158, 159, and 160, respectively;

wherein the antibody or antigen-binding fragment thereof specifically binds apelin, preferably human apelin.

Embodiment 2 is the isolated monoclonal antibody or antigen-binding fragment of embodiment 1, comprising a heavy chain variable region having a polypeptide sequence at least 95% identical to SEQ ID NO:1, 3, 5, 7, 9, 11, 13, 15, 17, 19, 21, 23, 25, 27, 29, 31, 33, 35, 37, or 39, or a light chain variable region having a polypeptide sequence at least 95% identical to SEQ ID NO:2, 4, 6, 8, 10, 12, 14, 16, 18, 20, 22, 24, 26, 28, 30, 32, 34, 36, 38, or 40.

Embodiment 3 is the isolated monoclonal antibody or antigen-binding fragment of embodiment 1 or 2, comprising (a) a heavy chain variable region having the polypeptide sequence of SEQ ID NO:1, and a light chain variable region having the polypeptide sequence of SEQ ID NO:2;

(b) a heavy chain variable region having the polypeptide sequence of SEQ ID NO:3, a light chain variable region having the polypeptide sequence of SEQ ID NO:4;

(c) a heavy chain variable region having the polypeptide sequence of SEQ ID NO:5, a light chain variable region having the polypeptide sequence of SEQ ID NO:6;

(d) a heavy chain variable region having the polypeptide sequence of SEQ ID NO:7, a light chain variable region having the polypeptide sequence of SEQ ID NO:8;

(e) a heavy chain variable region having the polypeptide sequence of SEQ ID NO:9, a light chain variable region having the polypeptide sequence of SEQ ID NO:10;

(f) a heavy chain variable region having the polypeptide sequence of SEQ ID NO:11, a light chain variable region having the polypeptide sequence of SEQ ID NO:12;

(g) a heavy chain variable region having the polypeptide sequence of SEQ ID NO:13, a light chain variable region having the polypeptide sequence of SEQ ID NO:14;

(h) a heavy chain variable region having the polypeptide sequence of SEQ ID NO:15, a light chain variable region having the polypeptide sequence of SEQ ID NO:16;

(i) a heavy chain variable region having the polypeptide sequence of SEQ ID NO:17, a light chain variable region having the polypeptide sequence of SEQ ID NO:18;

(j) a heavy chain variable region having the polypeptide sequence of SEQ ID NO:19, a light chain variable region having the polypeptide sequence of SEQ ID NO:20;

(k) a heavy chain variable region having the polypeptide sequence of SEQ ID NO:21, a light chain variable region having the polypeptide sequence of SEQ ID NO:22;

(l) a heavy chain variable region having the polypeptide sequence of SEQ ID NO:23, a light chain variable region having the polypeptide sequence of SEQ ID NO:24;

(m) a heavy chain variable region having the polypeptide sequence of SEQ ID NO:25, a light chain variable region having the polypeptide sequence of SEQ ID NO:26;

(n) a heavy chain variable region having the polypeptide sequence of SEQ ID NO:27, a light chain variable region having the polypeptide sequence of SEQ ID NO:28;

(o) a heavy chain variable region having the polypeptide sequence of SEQ ID NO:29, a light chain variable region having the polypeptide sequence of SEQ ID NO:30;

(p) a heavy chain variable region having the polypeptide sequence of SEQ ID NO:31, a light chain variable region having the polypeptide sequence of SEQ ID NO:32;

(q) a heavy chain variable region having the polypeptide sequence of SEQ ID NO:33, a light chain variable region having the polypeptide sequence of SEQ ID NO:34;

(r) a heavy chain variable region having the polypeptide sequence of SEQ ID NO:35, a light chain variable region having the polypeptide sequence of SEQ ID NO:36;

(s) a heavy chain variable region having the polypeptide sequence of SEQ ID NO:37, a light chain variable region having the polypeptide sequence of SEQ ID NO:38; or (t) a heavy chain variable region having the polypeptide sequence of SEQ ID NO:39, a light chain variable region having the polypeptide sequence of SEQ ID NO:40.

Embodiment 4 is an isolated monoclonal antibody or antigen-binding fragment thereof to apelin that specifically binds to an epitope comprising the amino acid sequence of SEQ ID NO:188.

Embodiment 5 is an isolated monoclonal antibody or antigen-binding fragment thereof to apelin that specifically binds to an epitope comprising the amino acid sequence of SEQ ID NO:204.

Embodiment 6 is the isolated monoclonal antibody or antigen-binding fragment thereof of embodiment 4 or 5, wherein the antibody or antigen-binding fragment thereof inhibits apelin activity.

Embodiment 7 is the isolated monoclonal antibody or antigen-binding fragment thereof of embodiment 4, wherein the antibody or antigen-binding fragment thereof is capable of binding pyro-apelin-13, apelin-13, apelin-17, apelin-36, apelin-55, and/or other forms of apelin that share the same C-terminal end with apelin-13.

Embodiment 8 is the isolated monoclonal antibody or antigen-binding fragment thereof of embodiment 5, wherein the antibody or antigen-binding fragment thereof is capable of binding apelin-13 and/or pyro-apelin-13.

Embodiment 9 is the isolated monoclonal antibody or antigen-binding fragment of any one of embodiments 1 to 8, wherein the antibody or antigen-binding fragment thereof is chimeric.

Embodiment 10 is the isolated monoclonal antibody or antigen-binding fragment of any one of embodiments 1 to 9, wherein the antibody or antigen-binding fragment thereof is human or humanized.

Embodiment 11 is the isolated monoclonal antibody or antigen-binding fragment of embodiment 10, wherein the antibody or antigen-binding fragment thereof comprises:

a. a heavy chain variable region having the polypeptide sequence of SEQ ID NO:211, and a light chain variable region having the polypeptide sequence of SEQ ID NO:215;

b. a heavy chain variable region having the polypeptide sequence of SEQ ID NO:212, and a light chain variable region having the polypeptide sequence of SEQ ID NO:215;
c. a heavy chain variable region having the polypeptide sequence of SEQ ID NO:213, and a light chain variable region having the polypeptide sequence of SEQ ID NO:215;
d. a heavy chain variable region having the polypeptide sequence of SEQ ID NO:214, and a light chain variable region having the polypeptide sequence of SEQ ID NO:215;
e. a heavy chain variable region having the polypeptide sequence of SEQ ID NO:213, and a light chain variable region having the polypeptide sequence of SEQ ID NO:216;
f. a heavy chain variable region having the polypeptide sequence of SEQ ID NO:214, and a light chain variable region having the polypeptide sequence of SEQ ID NO:216;
g. a heavy chain variable region having the polypeptide sequence of SEQ ID NO:217, and a light chain variable region having the polypeptide sequence of SEQ ID NO:219; or
h. a heavy chain variable region having the polypeptide sequence of SEQ ID NO:218, and a light chain variable region having the polypeptide sequence of SEQ ID NO:220.

Embodiment 12 is an isolated nucleic acid encoding the monoclonal antibody or antigen-binding fragment of any one of embodiments 1 to 11.

Embodiment 13 is a vector comprising the isolated nucleic acid of embodiment 12.

Embodiment 14 is a host cell comprising the vector of embodiment 13.

Embodiment 15 is a pharmaceutical composition, comprising the isolated monoclonal antibody or antigen-binding fragment of any one of embodiments 1 to 11 and a pharmaceutically acceptable carrier.

Embodiment 16 is a method of blocking binding of apelin to an apelin receptor in a subject in need thereof, comprising administering to the subject the pharmaceutical composition of embodiment 15.

Embodiment 17 is a method of treating a diabetic retinopathy (DR) in a subject in need thereof, comprising administering to the subject the pharmaceutical composition of embodiment 15.

Embodiment 18 is a method of treating an age-related macular degeneration (AMID) in a subject in need thereof, comprising administering to the subject the pharmaceutical composition of embodiment 15.

Embodiment 19 is a method of treating a diabetic macular edema (DME) in a subject in need thereof, comprising administering to the subject the pharmaceutical composition of embodiment 15.

Embodiment 20 is a method of treating a macular edema following retinal vein occlusion (RVO) in a subject in need thereof, comprising administering to the subject the pharmaceutical composition of embodiment 15.

Embodiment 21 is a method of treating a retinal degeneration in a subject in need thereof, comprising administering to the subject the pharmaceutical composition of embodiment 15.

Embodiment 22 is a method of treating a myopic choroidal neovascularization (mCNV) in a subject in need thereof, comprising administering to the subject the pharmaceutical composition of embodiment 15.

Embodiment 23 is a method of treating a diabetic nephropathy in a subject in need thereof, comprising administering to the subject the pharmaceutical composition of embodiment 15.

Embodiment 24 is a method of treating a chronic kidney disease (CKD) in a subject in need thereof, comprising administering to the subject the pharmaceutical composition of embodiment 15.

Embodiment 25 is a method of treating a non-alcoholic steatohepatitis (NASH) in a subject in need thereof, comprising administering to the subject the pharmaceutical composition of embodiment 15.

Embodiment 26 is a method of treating a liver cirrhosis in a subject in need thereof, comprising administering to the subject the pharmaceutical composition of embodiment 15.

Embodiment 27 is a method of treating a plaque neovascularization in a subject in need thereof, comprising administering to the subject the pharmaceutical composition of embodiment 15.

Embodiment 28 is a method of treating a rubeosis iridis in a subject in need thereof, comprising administering to the subject the pharmaceutical composition of embodiment 15.

Embodiment 29 is a method of treating a neovascular glaucoma in a subject in need thereof, comprising administering to the subject the pharmaceutical composition of embodiment 15.

Embodiment 30 is a method of treating a corneal neovascularization (CNV) in a subject in need thereof, comprising administering to the subject the pharmaceutical composition of embodiment 15.

Embodiment 31 is a method of treating a retinopathy of prematurity (ROP) in a subject in need thereof, comprising administering to the subject the pharmaceutical composition of embodiment 15.

Embodiment 32 is a method of treating a retinopathy in a subject in need thereof, comprising administering to the subject the pharmaceutical composition of embodiment 15.

Embodiment 33 is a method of treating a macular degeneration in a subject in need thereof, comprising administering to the subject the pharmaceutical composition of embodiment 15.

Embodiment 34 is a method of treating a ovarian hyperstimulation syndrome (OHSS) in a subject in need thereof, comprising administering to the subject the pharmaceutical composition of embodiment 15.

Embodiment 35 is a method of treating a uterine bleeding in a subject in need thereof, comprising administering to the subject the pharmaceutical composition of embodiment 15.

Embodiment 36 is a method of treating an endometriosis in a subject in need thereof, comprising administering to the subject the pharmaceutical composition of embodiment 15.

Embodiment 37 is a method of treating an endometrial hyperplasia and cancer in a subject in need thereof, comprising administering to the subject the pharmaceutical composition of embodiment 15.

Embodiment 38 is a method of treating a myometrial leiomyomas in a subject in need thereof, comprising administering to the subject the pharmaceutical composition of embodiment 15.

Embodiment 39 is a method of treating an adenomyosis in a subject in need thereof, comprising administering to the subject the pharmaceutical composition of embodiment 15.

Embodiment 40 is a method of treating a cancer in a subject in need thereof, comprising administering to the subject the pharmaceutical composition of embodiment 15.

Embodiment 41 is the method of embodiment 40, wherein the pharmaceutical composition further comprises a second anti-cancer agent.

Embodiment 42 is the method of embodiment 41, wherein the second anti-cancer agent is an anti-VEGF agent.

Embodiment 43 is the method of embodiment 42, wherein the anti-VEGF agent is AVASTIN® or a bevacizumab biosimilar agent.

Embodiment 44 is the method of embodiment 42, wherein the anti-VEGF agent is a VEGFR1 and/or VEGFR2 blocker.

Embodiment 45 is the method of any one of embodiments 40 to 44, wherein the cancer is selected from the group consisting of lung cancer, gastric cancer, colon cancer, hepatocellular carcinoma, renal cell carcinoma, bladder urothelial carcinoma, cholangiocarcinoma, metastatic melanoma, breast cancer, ovarian cancer, cervical cancer, head and neck cancer, pancreatic cancer, glioma, glioblastoma, and other solid tumors, and non-Hodgkin's lymphoma (NHL), acute lymphocytic leukemia (ALL), chronic lymphocytic leukemia (CLL), chronic myelogenous leukemia (CML), multiple myeloma (MM), acute myeloid leukemia (AML), and other liquid tumors.

Embodiment 46 is the method of embodiment 45, wherein the cancer is cholangiocarcinoma.

Embodiment 47 is a method of treating a tissue fibrosis in a subject in need thereof, comprising administering to the subject the pharmaceutical composition of embodiment 15.

Embodiment 48 is a method of determining a level of apelin in a subject, the method comprising (a) obtaining a sample from the subject; (b) contacting the sample with an antibody or antigen-binding fragment of any one of embodiments 1 to 11; and (c) determining a level of apelin in the subject.

Embodiment 49 is the method of embodiment 48, wherein the sample is a tissue sample.

Embodiment 50 is the method of embodiment 49, wherein the tissue sample is a cancer tissue sample.

Embodiment 51 is the method of embodiment 49, wherein the tissue sample is a hepatic tissue sample.

Embodiment 52 is the method of embodiment 49, wherein the tissue sample is a kidney tissue sample.

Embodiment 53 is a method of producing the monoclonal antibody or antigen-binding fragment of any one of embodiments 1 to 11, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or culture.

Embodiment 54 is a method of producing a pharmaceutical composition comprising the monoclonal antibody or antigen-binding fragment of any one of embodiments 1 to 11, comprising combining the monoclonal antibody or antigen-binding fragment with a pharmaceutically acceptable carrier to obtain the pharmaceutical composition.

EXAMPLES

Example 1: Identification of Anti-Apelin Monoclonal Antibodies

Rabbits were immunized with Cys-apelin-17 (with a cysteine added at the N-terminus; C-KFRRQRPRLSHKGPMPF (SEQ ID NO:161)) and pyr-apelin-13-Cys (pyroglutamylated form of apelin-13 with a cysteine added at the C-terminus; pE-RPRLSHKGPMPF-C(SEQ ID NO:162)) peptides conjugated to KLH carrier protein. To generate rabbit mAbs, PBMCs were isolated from the whole blood of immunized rabbits and antigen specific B cells were grown in 96-well plates. B cells secreting pyr-apelin-13 (pyroglutamylated form of apelin-13; pE-RPRLSHKGPMPF (SEQ ID NO:163))-reactive antibodies were identified by antigen-binding ELISA screening of the B cell culture supernatants. High binding ELISA plates were coated with pyr-apelin-13 in carbonate coating buffer (pH 9.6) at 1 μg/ml overnight. After the plates were blocked with 1% BSA in TBS, diluted B cell culture supernatants (1 to 10 dilution) were added and the plates were incubated at room temperature for 90 minutes. Following rabbit antibody binding to pyr-apelin-13, goat anti-rabbit IgG Fc-conjugated to alkaline phosphatase was added, and antibody-antigen binding was detected by adding PNPP substrate and reading absorbance of ELISA plates at 405 nm. The rabbit antibody binding to pyr-apelin-13 was further confirmed by differential bindings of the antibodies to pyr-apelin-13-Cys (pE-RPRLSHKGPMPF-C(SEQ ID NO:162)), Cys-(Q) apelin-13 (CQRPRLSHKGPMPF (SEQ ID NO:164)) and Cys-apelin-17 (CKFRRQRPRLSHKGPMPF (SEQ ID NO:161)) peptides. To clone the anti-apelin-13 rabbit monoclonal antibodies, rabbit IgG cDNA was made from total RNA prepared from the identified B cells, amplified by PCR, and then cloned into an expression vector.

The variable regions of the heavy and light chains were sequenced. The sequences of heavy and light chain variable regions of the anti-apelin mAbs are listed in Table 1 and Table 2, respectively. The sequences of heavy and light chain CDRs of these mAbs are listed in Table 3 and Table 4, respectively. The heavy and light chain CDRs for the anti-apelin mAbs were determined utilizing the Kabat method.

TABLE 1

Sequences of heavy chain variable regions
for anti-apelin monoclonal antibodies (mAbs)

| mAb clones | VH |
|---|---|
| C8 | QSVEESGGRLVTPGTPLTLTCTVSGIDLYSNRMSWVRQAPGKGLEWIGSIGSSP WYASWAQGRFTISKTSSTTVNLKITSPTTEDTATYFCAKGGYRPGASVWGPGT LVTVSS (SEQ ID NO: 1) |
| C24 | QSLEESGGRLVTPGTPLTLTCTVSGIDLYTNRVSWVRQAPGKGLDWIGSIGSSP WYASWAQGRFTISKTSTTVNLKITSSTTEDTATYFCAKGGYRPGGSIWGPGTLV TVSS (SEQ ID NO: 3) |

TABLE 1-continued

Sequences of heavy chain variable regions
for anti-apelin monoclonal antibodies (mAbs)

| mAb clones | VH |
|---|---|
| C25 | QSLEESGGGLVTPGTPLTLTCTVSGIDLYTNRMSWVRQAPGKGLEWIGSIGSSP WFASWALGRFTISKTSTTVNLKITSPTTEDTATYFCAKGGYRPGASVWGPGTLV TVSS (SEQ ID NO: 5) |
| C7 | QSLEESGGRLAKPDETLTLTCTVSGIDLNSHAMDWVRQAPGKGLEWIGVIAPD TRTYYATWARGRFTISKTSSTVELKMTSLTTEDTATYFCAAYPIEPGANIWGP GTLVTVSS (SEQ ID NO: 7) |
| C6 | QSLEESGGRLVKPDETLTLTCTVSGIDLSNYAMDWVRQAPGKGLEWIGVIAPN RRTYYPTWARGRFTISKTSSTVDLKMTSLTTEDTATYFCATYPIEPGANIWGP GTLVTVSS (SEQ ID NO: 9) |
| C1 | QSLEESGGRLVTPGGSLTLTCTVSGFSLSSYAMDWVRQAPGKGLEWIGVIAPN GATYYPTWARGRFTISKTSTTVDLKMTSLTAADTATYFCATYPIDAGANIWGP GTLVTVSS (SEQ ID NO: 11) |
| C16 | QSLEESGGRLVTPGGSLTLTCTVSGIDLNSYAMDWVRQAPGKGLEWIGVIAPN HYTYYPTWARGRFTISKTSTTVDLKMTRLTTEDTATYFCATYPIESGSNIWGPG TLVIVSS (SEQ ID NO: 13) |
| C20 | QSLEESGGRLVTPGGSLTLTCTVSGIDLNNYAIDWVRQAPGKGLEWIGVIAPNH YTCYPTWARGRFTISKTSTTVDLKMTSLTTEDTATYFCAAYPIETGSNIWGPGT LVIVSS (SEQ ID NO: 15) |
| C22 | QSLEESGGRLVTPGGSLTLTCTVSGIDLNNYAMDWVRQAPGKGLEWIGVIAPN HYTYYPTWARGRFTISKTSTTVDLKMTSLTTEDTATYFCATYPIETGSNIWGPG TLVIVSS (SEQ ID NO: 17) |
| C10 | QSLEESGGRLVTPGGSLTLTCTVSGIDLNSYAIDWVRQAPGKGLEWIGVIAPSG TTYYPTWAKGRFTISKTSTTVDLKVTGLTTEDTATYFCAAYPIDPGSNIWGPGT LVTVSS (SEQ ID NO: 19) |
| C12 | QSLEESGGRLVTPGGSLTLTCTVSGIDLSSYAIDWVRQAPGKGLEWIGVIAPSST TYYPTWAKGRFTISKTSSTVDLKVIGLTTEDTATYFCAAYPIDPGSNVWGPGT LVTVSS (SEQ ID NO: 21) |
| C13 | QSLEESGGRLAKPGETLTLTCTVSGIDLNSHAVDWVRQAPGKGLEWIGVIGPG GNTYYASWAKGRFTISKTSSTTVDLKMTSLTAEDTATFFCATYPIYSGDNIWGP GTLVTVSS (SEQ ID NO: 23) |
| C14 | QSPEESGGRLVTPGGSLTLTCKISGVDLSNYAMDWVRQAPGKGLEWIGVIAPN DATYYPTWARGRLTISKTSTTVDLKMTRLTTEDTATYFCAAYPIDVGANVWGP GTLVTVSS (SEQ ID NO: 25) |
| C11 | QSLEESGGRLVSPGGSLTLTCTVSGIDLSSHAMDWVRQAPGKGLEWIGVIAPND ATYYPTWARGRFTISKTSTTVGLKMTRLTTEDTATYFCAAYPIDAGANVWGPG TLVTVSS (SEQ ID NO: 27) |
| C4 | QEQLEQSGGGAEGGLVKPGGSLELCCKASGFTLSSSYWICWVRQAPGKGLEWI GCIHYGSSGTAYYASWVNGRFTLSRDIDQSTGCLQLNSLTAADTAMYYCARFL SDMYYYNLWGPGTLVTVSS (SEQ ID NO: 29) |
| C5 | QSVEESGGRLVTPGTPLTLTCTVSGFSLSGAWMNWVRQAPGKGLEWIGVVSSD DNIYYADWAKGRFTISKTSTTVDLKLTSPTTEDTATYFCARNLGTIWGPGTLVT VSS (SEQ ID NO: 31) |
| C9 | QEQLEESGGDLVKPEGSLTLTCTASGFSFSSSYWICWVRQAPGKGLEWIACIYQ SGDGRTWYASWAEGRFTISKTSPTTVTLQMASLTAADTATYFCARCPHNTYSH FDLWGPSTLVTVSS (SEQ ID NO: 33) |
| C26 | QEQLEESGGGLVQPEGSLTLTCTASGFTLSNYWMSWVRQAPGKGLVWIGCIDI GSDDTYYASWAKGRFTISRTSSTTVTLQVTSLTAADTATYFCARSGGLWGPGT LVTVSS (SEQ ID NO: 35) |
| C27 | QSVEESGGRLVTPGGSLTLTCTVSGIDLINAWMNWVRQAPGKGLEWIGTTTDD DTIYYANWAKGRFTISRTSTTVDLKVTSLTSEDTATYFCSKGRIWGPGTLVTVS L (SEQ ID NO: 37) |
| C17 | QSVEESGGRLVKPDETLTLTCAVSGIDLSSNAMNWVRQAPGEGLEWIGSMYTD GTTYYANWAKGRFTISRASSTTVDLKMTSLTAADTATYFCARGDIWGPGTLVT VSS (SEQ ID NO: 39) |

VH: heavy chain variable region

TABLE 2

Sequences of light chain variable regions for anti-apelin mAbs mAb clonesVL

C8  QVLTQTESPVSAPVGGTVTIACQSSQSVYDNNDLAWYQQKAGQTPKRLIYLAS
SLDSGVPSRFKGSGSGTEFTLTISDLECDDAATYYCAGGYSGDIYTFGGGTEVV
VE (SEQ ID NO: 2)

C24 QVLTQSASPVSAAVGDSVTIACQSSQSVYDNNDLGWYQQKPGQTPKRLIYLAS
SLDSGVPSRFSGSGSGTQFTLTISDLECDDAATYYCAGGYSGDIYTFGGGTEVV
VK (SEQ ID NO: 4)

C25 QVLTQTESPVSAPVGGTVTIACQSSQSVYDNNDLAWYQQKAGQTPKRLIFLAS
SLDSGVPSRFKGSGSGTEFTLTISDLECDDAATYYCAGGYNGDIYTFGGGTEVV
VK (SEQ ID NO: 6)

C7  DPVLTQTPSPVSAPVGGTVTIGCQASESVDYNNQLSWYQQKPGQAPKRLMYY
VSTLDSGVPSRFKGSGSGTQFTLTISDLECDDAATYYCQGGYPYNIYPFGGGTE
VVVK (SEQ ID NO: 8)

C6  DPVLTQTPSPVSAPVGGTVTIGCQSSESVDYNNQLSWYQQKPGQPPKRLMYYV
STLDSGVPSRFKGSGSGTQFTLTISDLECDDAATYYCQGGYISNIYPFGGGTEVV
VK (SEQ ID NO: 10)

C1  DPVLTQTPSSVSAAVGGTVTIGCQSSESVDNNNQLSWYQQKSGQPPKRLMYYV
STLDSGVPSRFKGSGSGTHFTLTISGVQCYDAATYYCQGGYISNLYPFGGGTEV
VVK (SEQ ID NO: 12)

C16 DPVLTQTPSSVSAAVGGTVTIGCQSSESVGMNNQLSWYQQKPGQPPKRLMYY
VSTLDSGVPSRFKGSGSGTQFSLTISDLECDDAGTYYCQGGYISNLYPFGGGTE
VVVK (SEQ ID NO: 14)

C20 DPMLTQTPSSVSAAVGGTVTISCQSSESVDMNNQLSWYQQKPGQPPKRLMYY
VSTLDSGVPSRFKGSGSGIHFSLTISDLECADAGTYYCQGGYISNLYPFGGGTEV
VVK (SEQ ID NO: 16)

C22 DPVLTQTPSSVSAAVGGTVTISCQSSESVDMNNQLSWYHQKSGQPPKRLMYYV
STLDSGVPSRFKGSGSGTQFTLTISGVQCDDAGTYYCQGGYISNLYPFGGGTEV
VVK (SEQ ID NO: 18)

C10 DPVLTQTPSSVSAAVGGTATIGCQSSESVDYGNQLSWYQQKPGQPPKRLAYYV
SILDAGVPSRFKGSGSGTQFTLTISDLECDDAATYYCQGGYISNLYPFGGGTEVV
VQ (SEQ ID NO: 20)

C12 DPVLTQTPSSVSAAVGGTVTIGCQSSESVDYGNQLSWYQQKPGQPPKRLTYYV
SILDAGVPSRFKGSGSGTQFTLTISDLECDDAATYYCQGGYISNLYPFGGGTEVV
VQ (SEQ ID NO: 22)

C13 DPVLTQTPPSVSAAVGGTVTINCQSSESVDNNNQLSWYQQKVGQPPKRLMYY
ASTLDSGVPSRFKGGGSGTHFTLTITDLECDDAATYYCQGGTATNIYPFGGGTE
VVVK (SEQ ID NO: 24)

C14 DPMLTQTASPVSAAVGGTVTINCQSSESVDYNNQLSWYQQKPGQPPKRLMYY
VSTLDSGVPSRFKGSGSGTQFSLTISDLECDDAGTYYCQGGYISNLYPFGGGTE
VVVK (SEQ ID NO: 26)

C11 DPMLTQTASPVSAHVGGTVTINCQSSESVDYNNQLSWYQQKPGQPPKRLMYY
VSTLDSGVPSRFKGSGSGTQFSLTISDLECDDAGTYYCQGGYISNLYPFGGGTE
VVVK (SEQ ID NO: 28)

C4  QVLTQTPASVSAAVGGTVTINCQASQSIYNNNQLSWYQQKPGQPPKLLIYYAST
LASGVSSRFKGSGSGTQFTLTISGVQCDDAATYYCQGQFNCRSADCHAFGGGT
EVVVK (SEQ ID NO: 30)

C5  QVLTQTESPVSAAVGGTVTINCQSSQSVWSNYLSWFQQKPGQPPKVLIYGTSKL
PSGVPSRFSGSGSG1EFTLTINDLECDDAATYYCAGGYSGHIYSFGGGTEVVVK
(SEQ ID NO: 32)

C9  ADIVMTQTPASVEAAVGGTVTIKCQASQSINSWLSWYQQKPGQPPKPLIYGAS
NLASGVPSRFKGSGSGTQFTLTISDLECADAATYSCLGYYYSSYNSVGFWAFGG
GTEVVVK (SEQ ID NO: 34)

C26 QVLTQTPSSTSAAVGGTVTINCQASQSVYNNNDLAWYQQKPGQPPKRLIYEAS
KLASGVPSRFSGSGSGTQFTLTISDLECDDAATYYCAGGWSGNFYVFGGGTEV
VVK (SEQ ID NO: 36)

C27 QVLTQTPASVSAAVGGTVTINCQASQSVYDGNWLCWYQQKPGQPPKRLIYKA
STLESGVPSRFKGSGSGTQFTLTISDLECDDAATYYCQGGFTSNIYPFAGGTEVV
VK (SEQ ID NO: 38)

TABLE 2-continued

Sequences of light chain variable regions for anti-apelin mAbs

| mAb clones | VL |
|---|---|
| C17 | QVLTQTASPVSAAVGGTVTISCQSSQSVYNNNWLAWFQQKPGQPPKRLIYGTS ELASGVPSRFKGSGSGTQFTLTISGVQCDDAATYYCLGTYSSNIHVFGGGTEVV VK (SEQ ID NO: 40) |

VL: light chain variable region

TABLE 3

CDR regions 1-3 of heavy chain for anti-apelin mAbs

| mAb clones | HC CDR1 (SEQ ID NO:) | CDR2 (SEQ ID NO:) | CDR3 (SEQ ID NO:) |
|---|---|---|---|
| C8 | SNRMS (41) | SIGSSPWYASWAQG (42) | GGYRPGASV (43) |
| C24 | TNRVS (44) | SIGSSPWYASWAQG (45) | GGYRPGGSI (46) |
| C25 | TNRMS (47) | SIGSSPWFASWALG (48) | GGYRPGASV (49) |
| C7 | SHAMD (50) | VIAPDTRTYYATWARG (51) | YPIEPGANI (52) |
| C6 | NYAMD (53) | VIAPNRRTYYPTWARG (54) | YPIEPGANI (55) |
| C1 | SYAMD (56) | VIAPNGATYYPTWARG (57) | YPIDAGANI (58) |
| C16 | SYAMD (59) | VIAPNHYTYYPTWARG (60) | YPIESGSNI (61) |
| C20 | NYAID (62) | VIAPNHYTCYPTWARG (63) | YPIETGSNI (64) |
| C22 | NYAMD (65) | VIAPNHYTYYPTWARG (66) | YPIETGSNI (67) |
| C10 | SYAID (68) | VIAPSGTTYYPTWAKG (69) | YPIDPGSNI (70) |
| C12 | SYAID (71) | VIAPSSTTYYPTWAKG (72) | YPIDPGSNV (73) |
| C13 | SHAVD (74) | VIGPGGNTYYASWAKG (75) | YPIYSGDNI (76) |
| C14 | NYAMD (77) | VIAPNDATYYPTWARG (78) | YPIDVGANV (79) |
| C11 | SHAMD (80) | VIAPNDATYYPTWARG (81) | YPIDAGANV (82) |
| C4 | SSYWIC (83) | CIHYGSSGTAYYASWVNG (84) | FLSDMYYYNL (85) |
| C5 | GAWMN (86) | VVSSDDNIYYADWAKG (87) | NLGTI (88) |
| C9 | SSYWIC (89) | CIYQSGDGRTWYASWAEG (90) | CPHNTYSHFDL (91) |
| C26 | NYWMS (92) | CIDIGSDDTYYASWAKG (93) | SGGL (94) |
| C27 | NAWMN (95) | TTTDDDTIYYANWAKG (96) | GRI (97) |
| C17 | SNAMN (98) | SMYTDGTTYYANWAKG (99) | GDI (100) |

HC: heavy chain;
CDR: complementarity determining region
The HC CDRs for the anti-apelin mAbs were determined utilizing the IMGT method (Lefranc, M.-P. et al., Nucleic Acids Res. 1999; 27:209-212).

TABLE 4

CDR regions 1-3 of light chain for anti-apelin mAbs

| mAb clones | LC CDR1 (SEQ ID NO:) | CDR2 (SEQ ID NO:) | CDR3 (SEQ ID NO:) |
|---|---|---|---|
| C8 | QSSQSVYDNNDLA (101) | LASSLDS (102) | AGGYSGDIYT (103) |
| C24 | QSSQSVYDNNDLG (104) | LASSLDS (105) | AGGYSGDIYT (106) |
| C25 | QSSQSVYDNNDLA (107) | LASSLDS (108) | AGGYNGDIYT (109) |
| C7 | QASESVDYNNQLS (110) | YVSTLDS (111) | QGGYPYNIYP (112) |

TABLE 4-continued

CDR regions 1-3 of light chain for anti-apelin mAbs

| mAb clones | LC CDR1 (SEQ ID NO:) | CDR2 (SEQ ID NO:) | CDR3 (SEQ ID NO:) |
|---|---|---|---|
| C6 | QSSESVDYNNQLS (113) | YVSTLDS (114) | QGGYISNIYP (115) |
| C1 | QSSESVDNNNQLS (116) | YVSTLDS (117) | QGGYISNLYP (118) |
| C16 | QSSESVGMNNQLS (119) | YVSTLDS (120) | QGGYISNLYP (121) |
| C20 | QSSESVDMNNQLS (122) | YVSTLDS (123) | QGGYISNLYP (124) |
| C22 | QSSESVDMNNQLS (125) | YVSTLDS (126) | QGGYISNLYP (127) |
| C10 | QSSESVDYGNQLS (128) | YVSILDA (129) | QGGYISNLYP (130) |
| C12 | QSSESVDYGNQLS (131) | YVSILDA (132) | QGGYISNLYP (133) |
| C13 | QSSESVDNNNQLS (134) | YASTLDS (135) | QGGTATNIYP (136) |
| C14 | QSSESVDYNNQLS (137) | YVSTLDS (138) | QGGYISNLYP (139) |
| C11 | QSSESVDYNNQLS (140) | YVSTLDS (141) | QGGYISNLYP (142) |
| C4 | QASQSIYNNNQLS (143) | YASTLAS (144) | QGQFNCRSADCHA (145) |
| C5 | QSSQSVWSNYLS (146) | GTSKLPS (147) | AGGYSGHIYS (148) |
| C9 | QASQSINSWLS (149) | GASNLAS (150) | LGYYYSSYNSVGFWA (151) |
| C26 | QASQSVYNNNDLA (152) | EASKLAS (153) | AGGWSGNFYV (154) |
| C27 | QASQSVYDGNWLC (155) | KASTLES (156) | QGGFTSNIYP (157) |
| C17 | QSSQSVYNNNWLA (158) | GTSELAS (159) | LGTYSSNIHV (160) |

LC: light chain;
CDR: complementarity determining region
The LC CDRs for the anti-apelin mAbs were determined utilizing the IMGT method
(Lefranc, M.-P. et al., Nucleic Acids Res. 1999; 27:209-212).

Example 2: Production and Purification of Recombinant mAbs

To obtain the recombinant anti-apelin rabbit mAbs, the expression vector containing the rabbit IgG cDNA was transiently transfected into HEK293 cells. The recombinant antibodies were produced in the suspension of these HEK293 cells and purified using Protein A affinity chromatography.

Figure 1B:
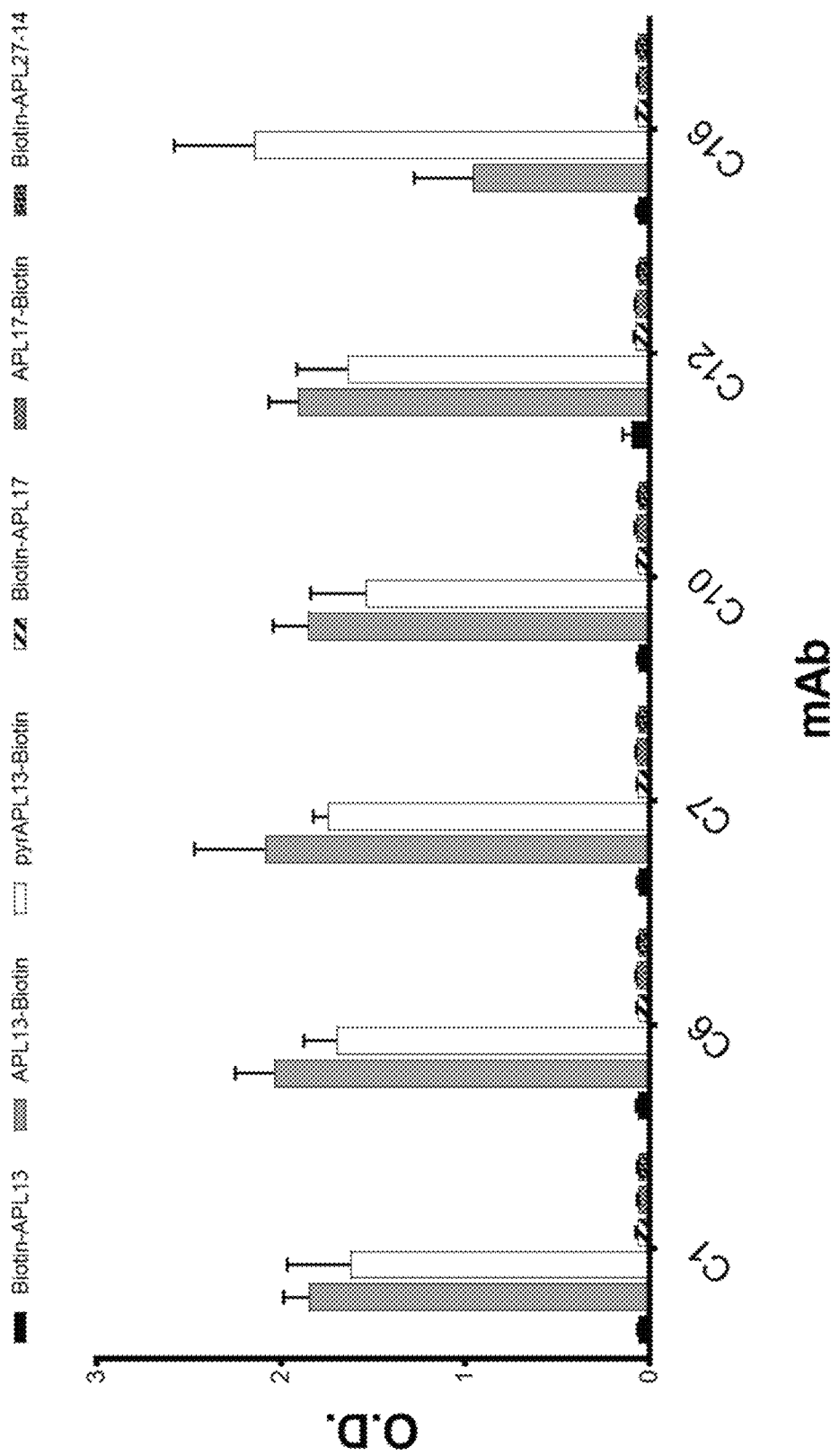
Figure 1C:
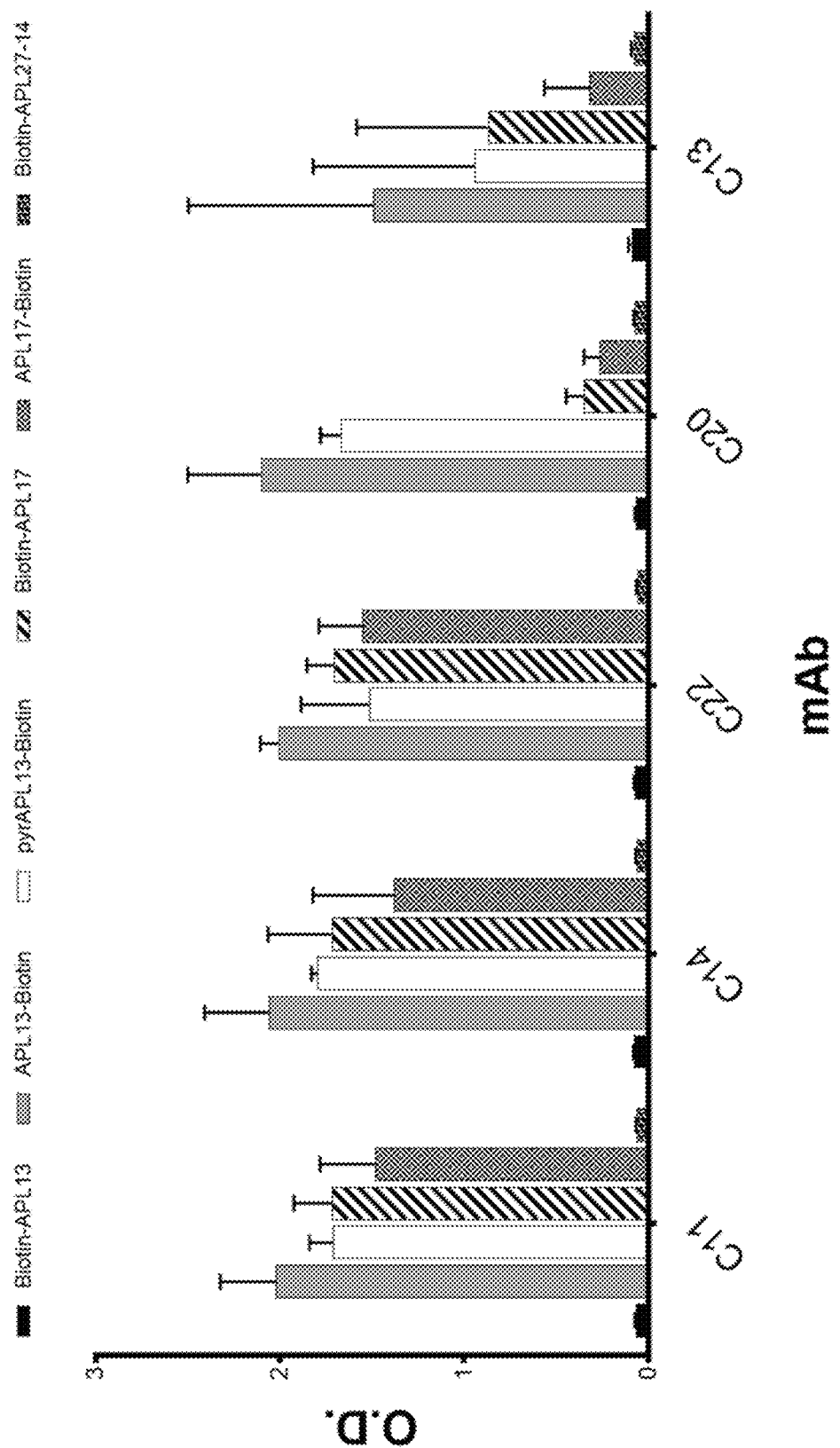
Figure 2A:
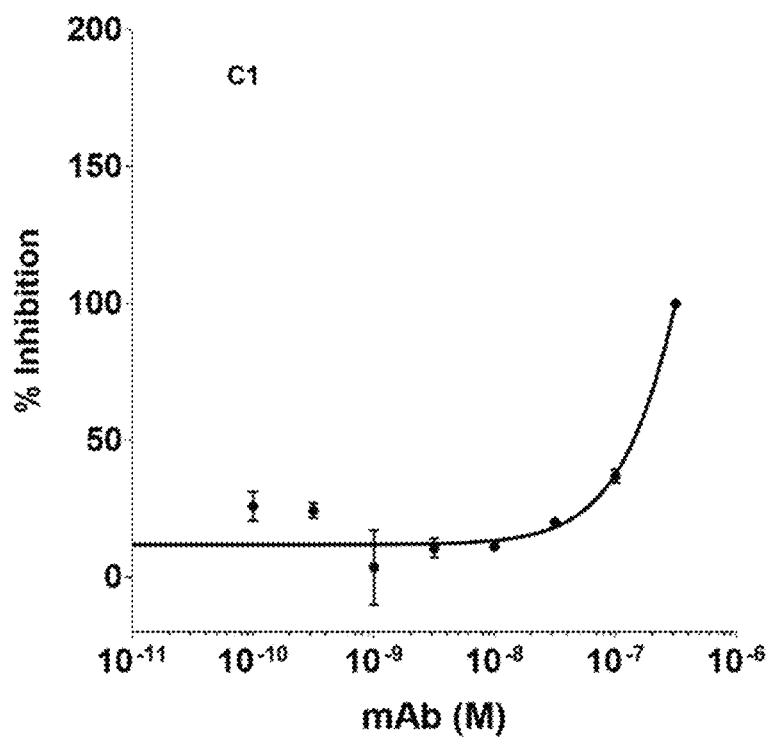
FIGS. 2A-2K show the neutralizing effect of select anti-apelin mAbs in a cell-based assay for apelin activity. Apelin activity was assessed for its ability to downregulate the forskolin (FSK)-induced cAMP production in cAMP Hunter™ CHO-K1 AGTRL1 Gi cells (DiscoverX #95-0147C2). Each mAb was assayed in triplicate at a given dilution. To calculate the % inhibition by a mAb at a given concentration, 0% inhibition was defined as the signal from the FSK-stimulated cells with apelin treatment and 100% inhibition was defined as the signal from the FSK-stimulated cells with no apelin treatment. The % inhibition was plotted against increasing concentrations of mAbs.
Figure 2B:
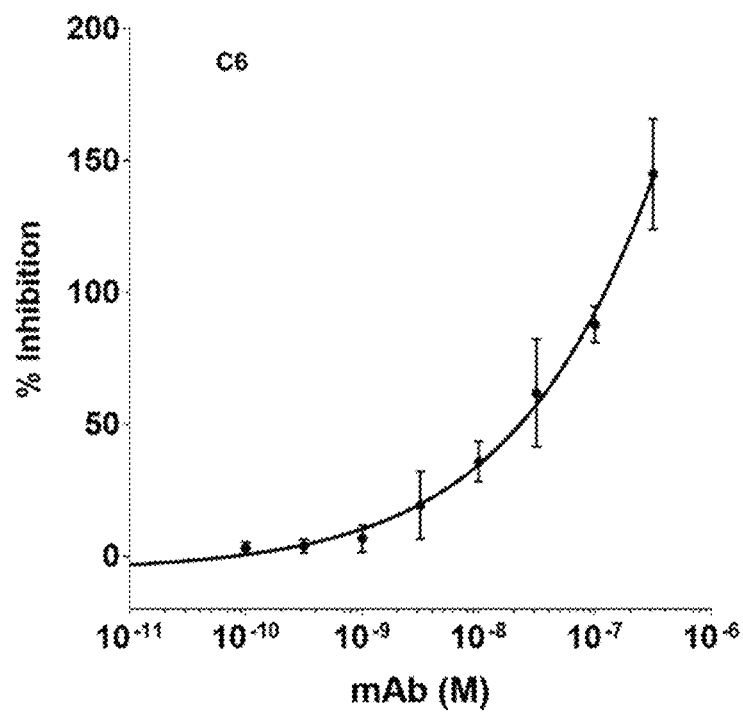
Figure 2C:
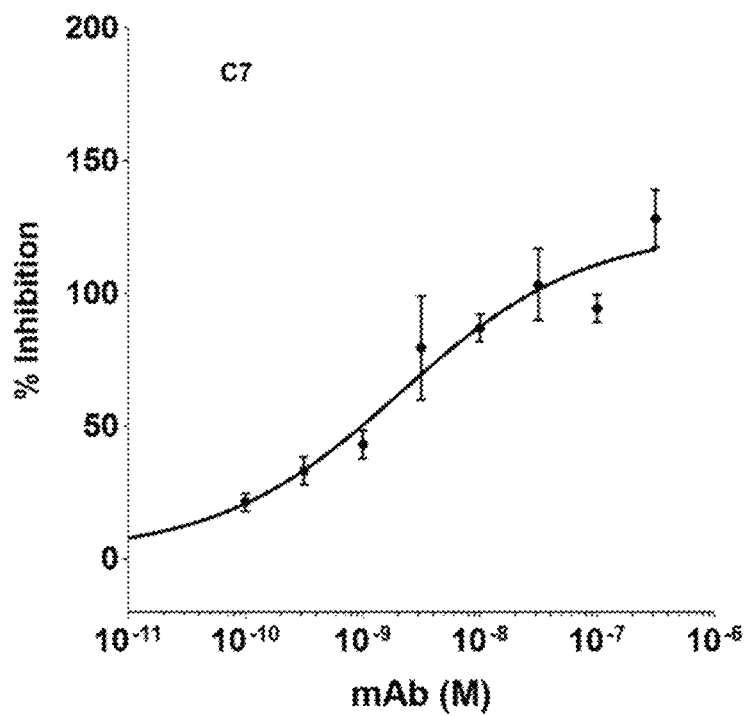
Figure 2D:
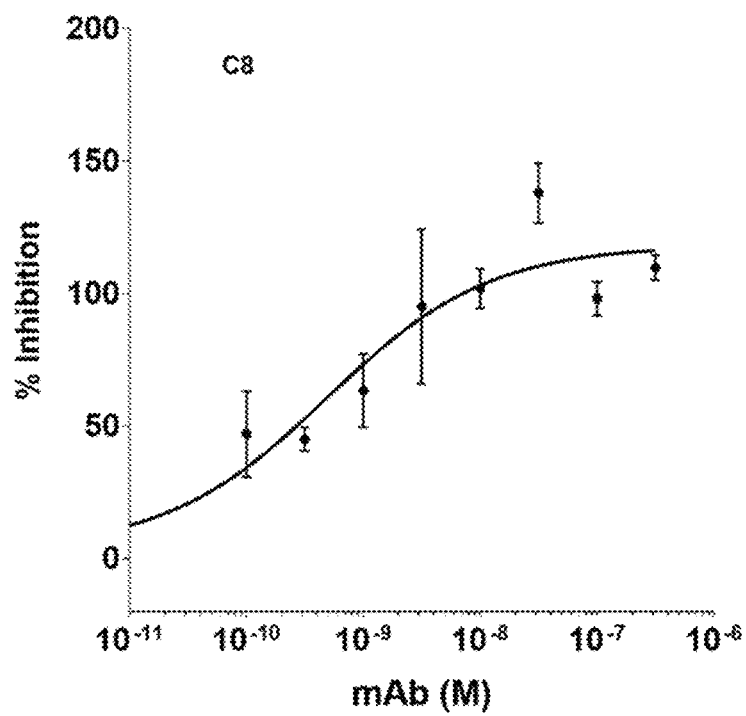
Figure 2E:
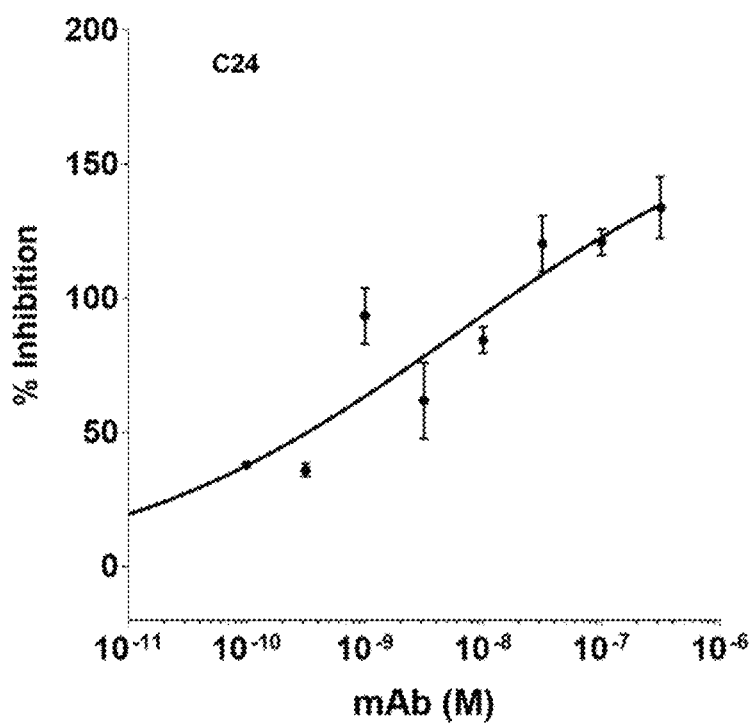
Figure 2F:
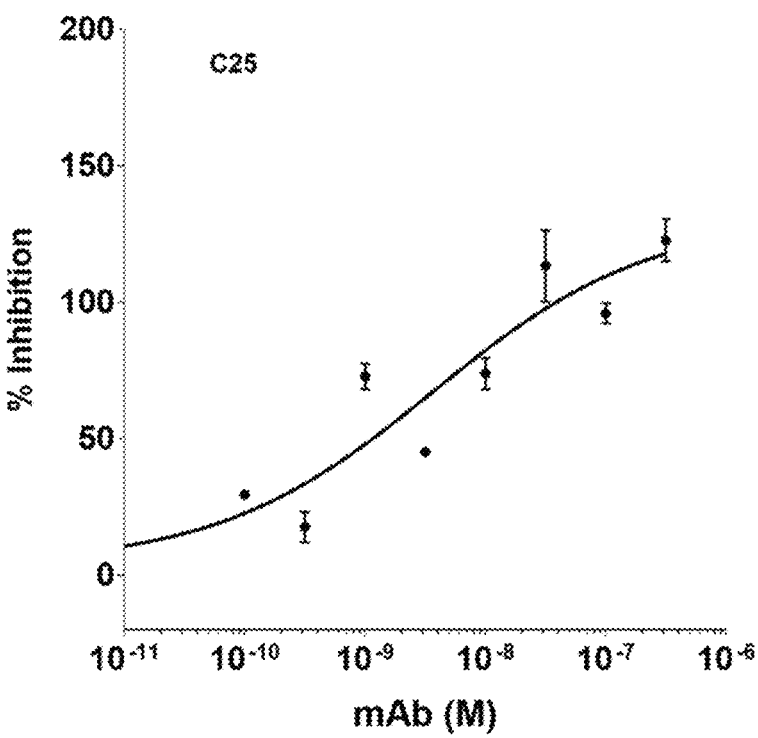
Figure 2G:
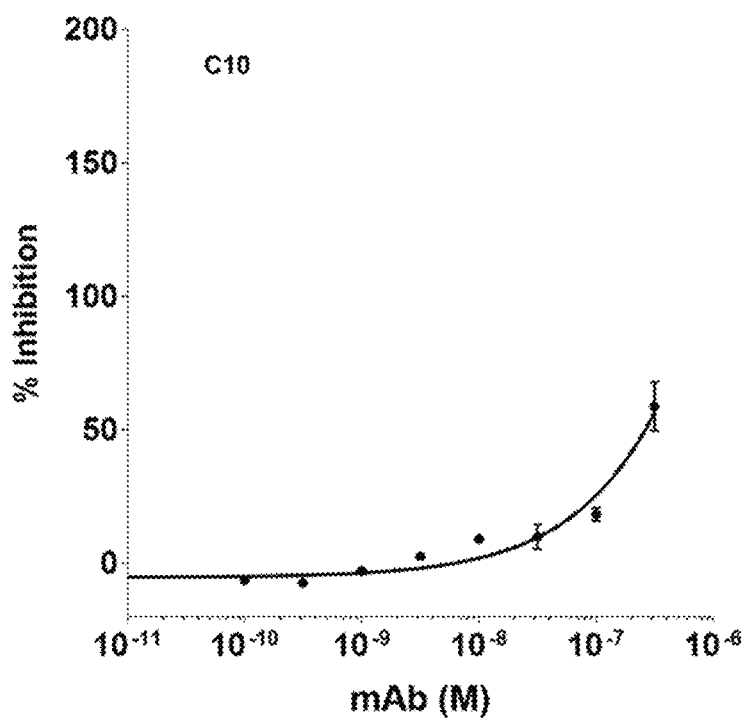
Figure 2H:
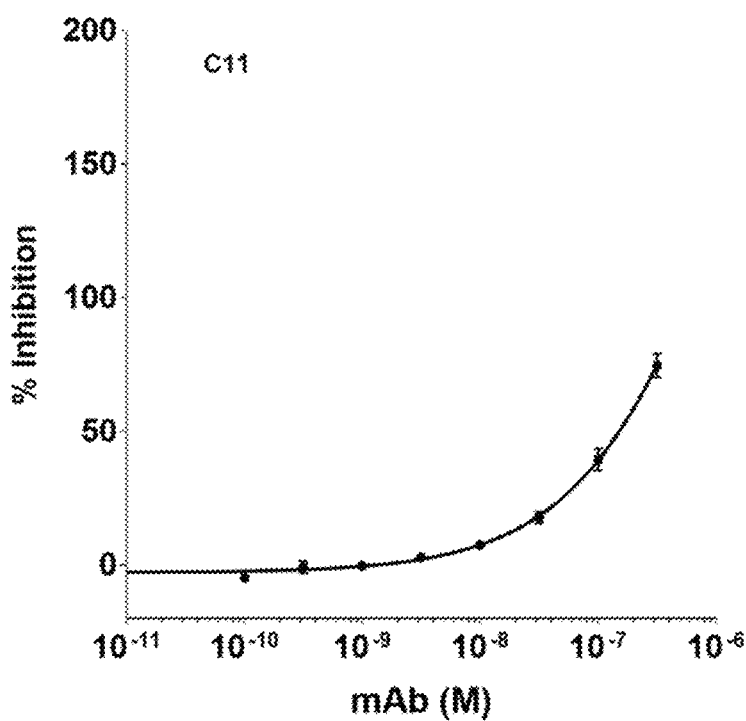
Figure 2I:
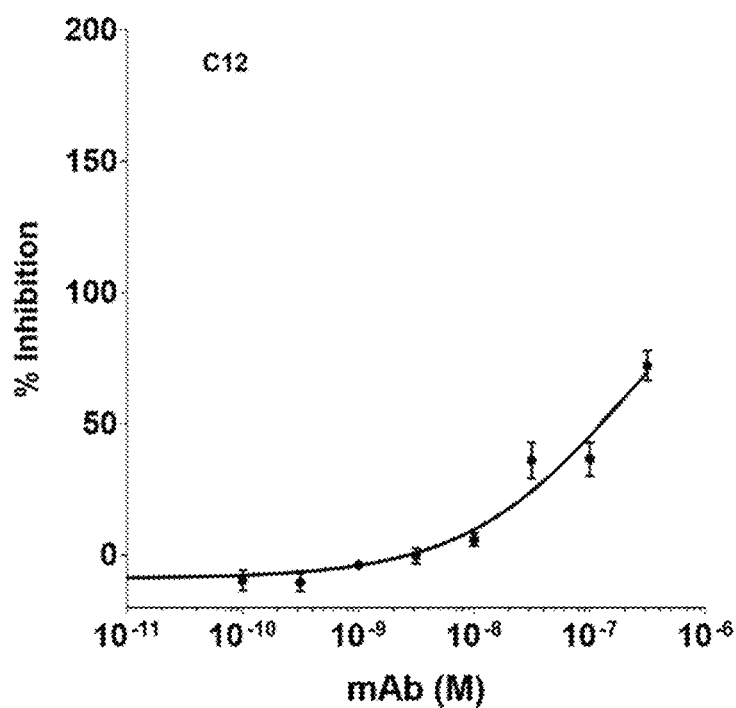
Figure 2J:
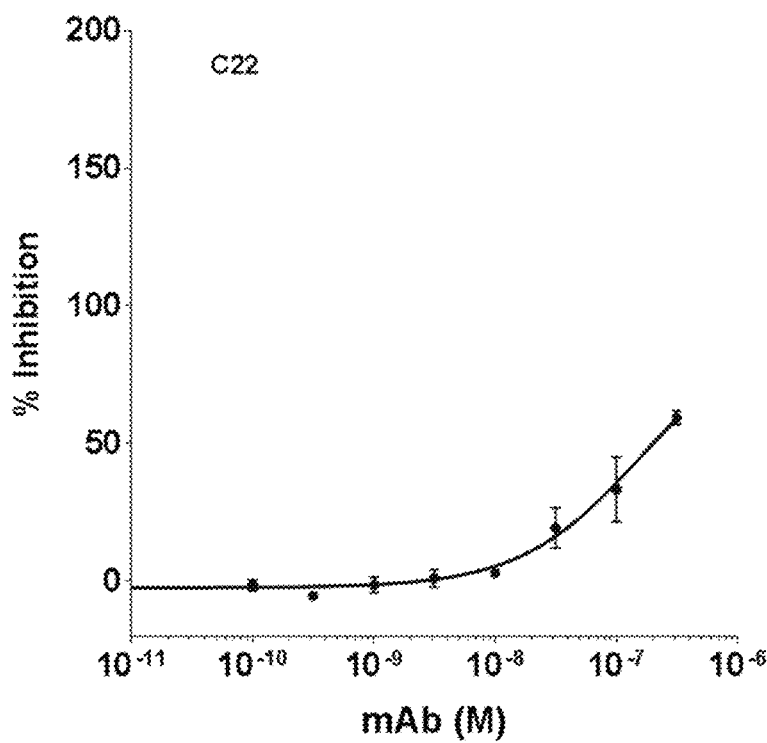
Figure 2K:
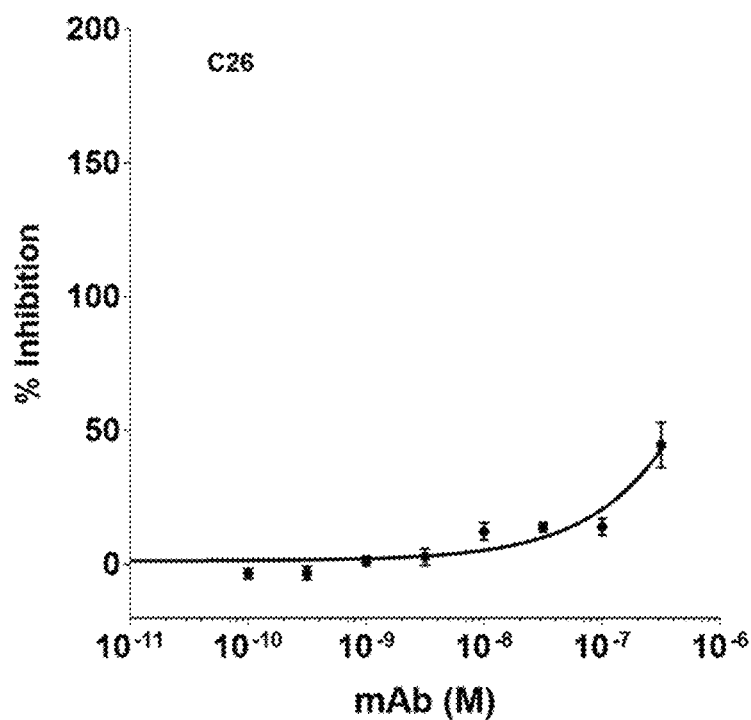

Example 3: Assessment of Specific Binding of Anti-Apelin mAbs to Apelin Peptides The specific binding of the recombinant rabbit mAbs to apelin was confirmed with ELISA using the following biotinylated apelin peptides: biotin-apelin-13 (biotin-QRPRLSHKGPMPF (SEQ ID NO:165)), apelin-13-biotin (QRPRLSHKGPMPF-biotin (SEQ ID NO:165)), pyr-apelin-13-biotin (pE-RPRLSHKGPMPF-biotin (SEQ ID NO:163)), biotin-apelin-17 (biotin-KFRRQRPRLSHKGPMPF (SEQ ID NO:166)), apelin-17-biotin (KFRRQRPRLSHKGPMPF-biotin (SEQ ID NO:166)), and biotin-apelin-(27-14) (biotin-GPGAWQGGRRKFRR (SEQ ID NO:167)). For the binding assay, neutravidin in carbonate coating buffer was coated on high binding ELISA plates at 1 µg/ml overnight. Peptides were added at 4 µg/ml after the plates were blocked with 1% BSA in TBS. After incubation of the plates at room temperature for 60 minutes, the plates were washed and then purified recombinant rabbit antibodies were added at 200 ng/ml. Following rabbit antibody binding to the peptides on the plates at room temperature for 90 minutes, goat anti-rabbit IgG Fc-conjugated to alkaline phosphatase was added, and antibody-antigen binding was detected by adding PNPP substrate and reading absorbance of ELISA plates at 405 nm. Each mAb was assayed in duplicate. Binding of anti-apelin mAbs to the apelin peptides are shown in FIGS. 1A-C(Biotin-APL13, biotin-apelin-13; APL13-Biotin, apelin-13-biotin; pyrAPL13-Biotin, pyr-apelin-13-biotin; Biotin-APL17, biotin-apelin-17; APL17-Biotin, apelin-17-biotin; Biotin-APL27-14, biotin-apelin-(27-14)). Apelin binding by certain mAbs in FIG. 1A is affected by biotinylation of the C-terminus of the apelin peptides, suggesting that the C-terminal end of apelin is important for apelin binding by these mAbs. Apelin binding by certain mAbs in FIG. 1B is affected by biotinylation of the N-terminus of apelin-13. The mAbs in FIG. 1C have different binding profiles from those in FIGS. 1A and 1B.

Example 4: Cell-Based Assay to Evaluate the Neutralizing Effect of Anti-Apelin mAbs The HitHunter® cAMP assay was carried out using the cAMP Hunter™ CHO-K1 AGTRL1 Gi cell line (#95-0147C2) (DiscoverX; Fremont, Calif.; USA). Cells were seeded in 384-well white tissue culture-treated plates (Corning #3570) (Corning; Corning, N.Y.; USA) at 10,000 cells/well and incubated at 37° C. overnight. The cells were then washed three times with serum-free media before being incubated at 37° C. for 5 minutes with an apelin/mAb mixture which had been pre-incubated at 37° C. for 15 minutes. The final apelin concentration incubated with the cells is 1.2 nM at this step. Forskolin (FSK) was added to each well so that the final FSK concentration was 15 µM and the final apelin concentration is 1 nM. After incubation for 30 minutes, the cAMP level was measured using the HIT-HUNTER® cAMP assay kit for Biologics (DiscoverX #90-0075LM10) according to the manufacturer's protocol. The chemiluminescent signal was read on an EnVision plate reader (384 US Lum) (Perkin Elmer; Waltham, Mass.; USA). Each mAb was assayed in triplicate at a given dilution. To calculate the % inhibition by a mAb at a given concentration, 0% inhibition was defined as the signal from the FSK-stimulated cells with apelin treatment and 100% inhibition was defined as the signal from the FSK-stimulated cells with no apelin treatment. The neutralizing effects of select anti-apelin mAbs are shown in FIGS. 2A-K.

Example 5: Affinity Analysis of Anti-Apelin mAbs

For KD determination for mAb clones C4, C5, C8, C9, C17, C24, C25, C26 and C27, biotin-apelin-13 (biotin-QRPRLSHKGPMPF (SEQ ID NO:165)) was immobilized on CM5-SA (streptavidin) chip (GE Lifesciences; Marlborough, Mass.) surface. Anti-apelin mAbs at four different concentrations (12.5 nM, 25 nM, 50 nM and 100 nM) were captured on the chip surface. The on- and off-rate for antibody-antigen binding were measured, curve fitted and calculated. The data are shown in Table 5.

For KD determination for mAb clones C1, C6, C7, C10, C11, C12, C14, C16, C20, and C22, apelin-13-biotin (QR-PRLSHKGPMPF-biotin (SEQ ID NO:165)) and pyr-apelin-13-biotin (pE-RPRLSHKGPMPF-biotin (SEQ ID NO:163)) were used in the Biacore assay described above. The data are shown in Table 6.

TABLE 5

KD values for anti-apelin mAbs from Biacore assay

| mAb clones | KD |
| --- | --- |
| C4 | 4.01 nM |
| C5 | 51.3 nM |
| C8 | 17.4 pM |
| C9 | 14.8 nM |
| C17 | 1.06 nM |
| C24 | 0.401 pM |
| C25 | 50.8 pM |
| C26 | 119 pM |
| C27 | 589 pM |

TABLE 6

KD values for anti-apelin mAbs measured with both apelin 13 and pyro-apelin 13 as measured by Biacore assay

| mAb clones | KD | |
| --- | --- | --- |
| | Apelin 13 | Pyro-apelin 13 |
| C1 | 48.9 pM | 0.154 pM |
| C6 | 5.96 pM | 0.513 pM |
| C7 | 3.14 pM | 0.326 pM |
| C10 | 6.46 pM | 0.0482 pM |
| C11 | 39.3 pM | 0.141 pM |

TABLE 6-continued

KD values for anti-apelin mAbs measured with both apelin 13 and pyro-apelin 13 as measured by Biacore assay

| mAb clones | KD | |
| --- | --- | --- |
| | Apelin 13 | Pyro-apelin 13 |
| C12 | 3.55 pM | 0.0555 pM |
| C14 | 141 pM | 6.49 pM |
| C16 | 14.3 nM | 6.14 nM |
| C20 | 202 pM | 41.9 pM |
| C22 | 107 pM | 0.155 pM |

Example 6: Epitope Mapping for Anti-Apelin mAbs

The antibody binding sites for anti-apelin mAbs C8, C24, and C25 were mapped using an ELISA-based peptide competition assay. Briefly, the mAb was captured on the ELISA plate and biotin-apelin-13 (SEQ ID NO:165) binding to the mAb was measured. Each of the competition peptides (Table 7) was assessed for its ability to inhibit biotin-apelin-13 binding to the mAb. An inhibition signal reflects the ability of the competition peptide to bind to the mAb in solution.

Figure 3A:
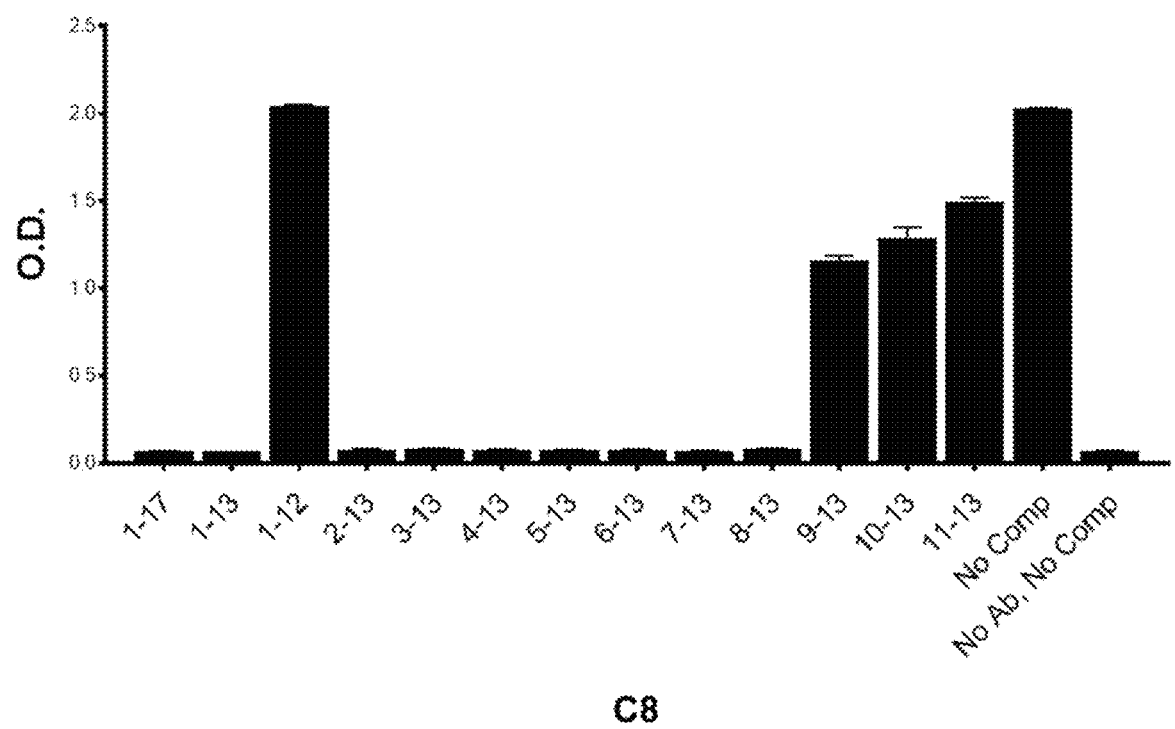
FIGS. 3A-3C show graphs demonstrating the inhibition of biotin-apelin-13 (SEQ ID NO:165) binding to the anti-apelin mAbs C8, C24 and C25 by the competition peptides in Table 7 as measured by ELISA. Goat-anti-rabbit IgG was immobilized on an ELISA plate. A mixture of a rabbit anti-apelin mAb (C8, C24, or C25) and a competition peptide was preincubated for 30 minutes at room temperature and then biotin-apelin-13 (SEQ ID NO:165) was added, mixed and the final solution was added on the plate. The binding of biotin-apelin-13 (SEQ ID NO:165) to the immobilized anti-apelin mAb, C8 (FIG. 3A), C24 (FIG. 3B), and C25 (FIG. 3C), was detected by adding streptavidin-conjugated to alkaline phosphatase and PNPP substrate, and measured as the absorbance at 405 nm.
Figure 3B:
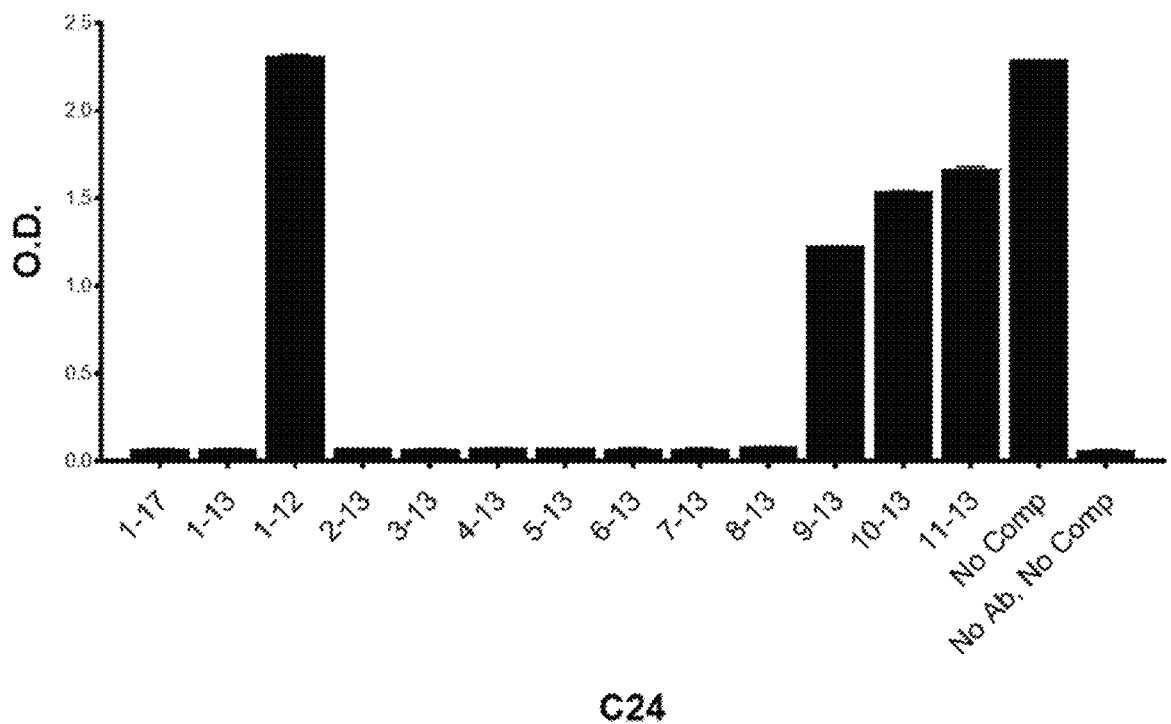
Figure 3C:
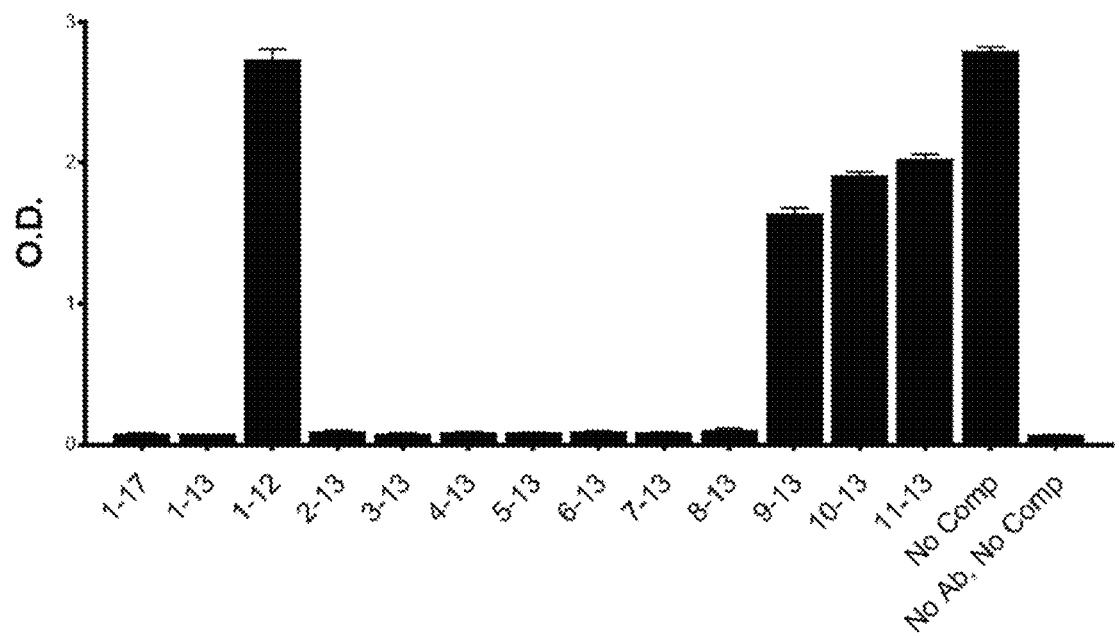

For the peptide competition assay, goat anti-rabbit IgG in carbonate coating buffer was coated on high binding ELISA plates at 1 µg/ml overnight. A mixture of a rabbit mAb (C8, C24, or C25) and a competition peptide (Table 7) was preincubated for 30 minutes at room temperature and then biotin-apelin-13 (SEQ ID NO:165) was added, mixed and the final solution was added onto the ELISA plates. After incubation at room temperature for 60 minutes, the plates were washed and then streptavidin-conjugated to alkaline phosphatase was added, and the binding was detected by adding PNPP substrate and reading absorbance of ELISA plates at 405 nm. Each competition peptide or control sample was assayed in duplicate for a given mAb. Inhibition of biotin-apelin-13 (SEQ ID NO:165) binding to the anti-apelin mAbs by the competition peptides are shown in FIGS. 3A-3C. "No comp:" no competition peptide was added; "No Ab, No Comp:" neither competition peptide nor anti-apelin mAb was added. As shown in FIG. 3A, when one amino acid is deleted from the C-terminus of apelin 13, the peptide does not bind to C8. Serial deletion of the N-terminal amino acids of apelin 13 does not have effect on its binding to C8 until residue number 8 is deleted. The mapping result indicates that C8 binds to the epitope comprising amino acids KGPMPF (SEQ ID NO:188). The same results were observed for C24 and C25. Therefore, C8, C24, and C25 all bind to the epitope comprising amino acids KGPMPF (SEQ ID NO:188).

Figure 4A:
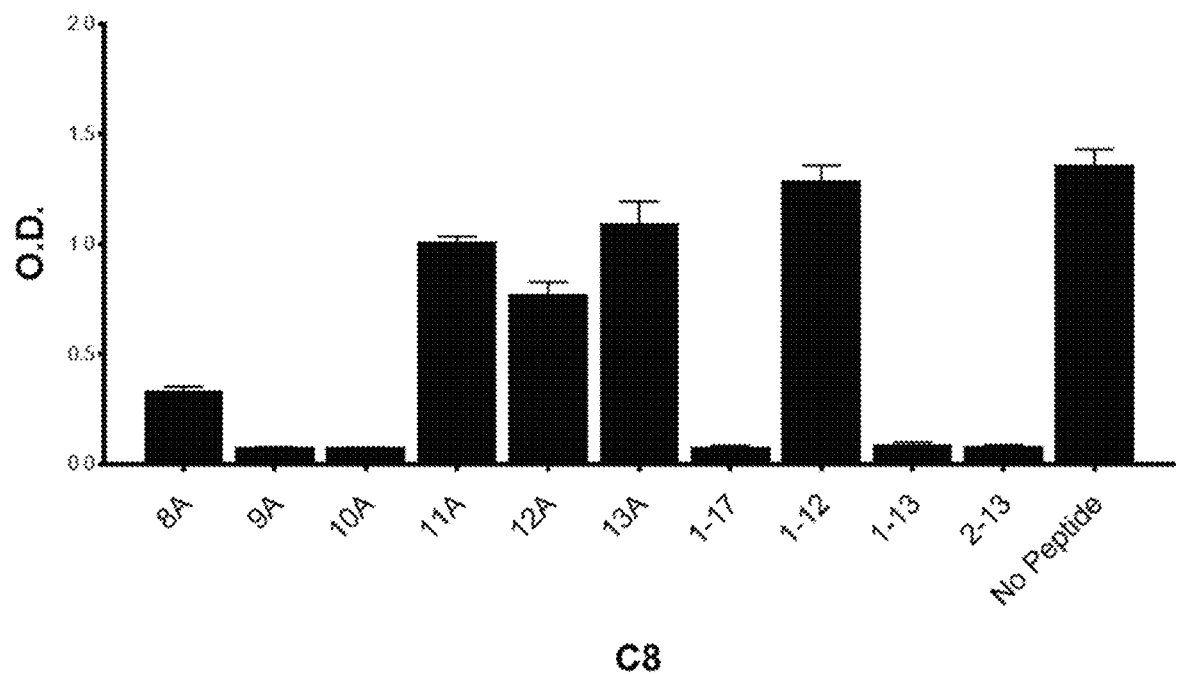
FIGS. 4A-4C show graphs demonstrating the inhibition of biotin-apelin-13 (SEQ ID NO:165) binding to the anti-apelin mAbs C8, C24 and C25 by the alanine scanning peptides (Table 8) derived from epitope 8-13 (KGPMPF (SEQ ID NO:188)) as measured by ELISA. Goat anti-rabbit IgG was immobilized on an ELISA plate. A mixture of a rabbit anti-apelin mAb (C8, C24, or C25) and an alanine scanning peptide was preincubated for 30 minutes at room temperature and then biotin-apelin-13 (SEQ ID NO:165) was added, mixed and the final solution was added on the plate. The binding of biotin-apelin-13 (SEQ ID: 165) to the immobilized anti-apelin mAbs, C8 (FIG. 4A), C24 (FIG. 4B), and C25 (FIG. 4C), was detected by adding streptavidin-conjugated to alkaline phosphatase and PNPP substrate, and measured as the absorbance at 405 nm. Several competition peptides were used as controls.
Figure 4B:
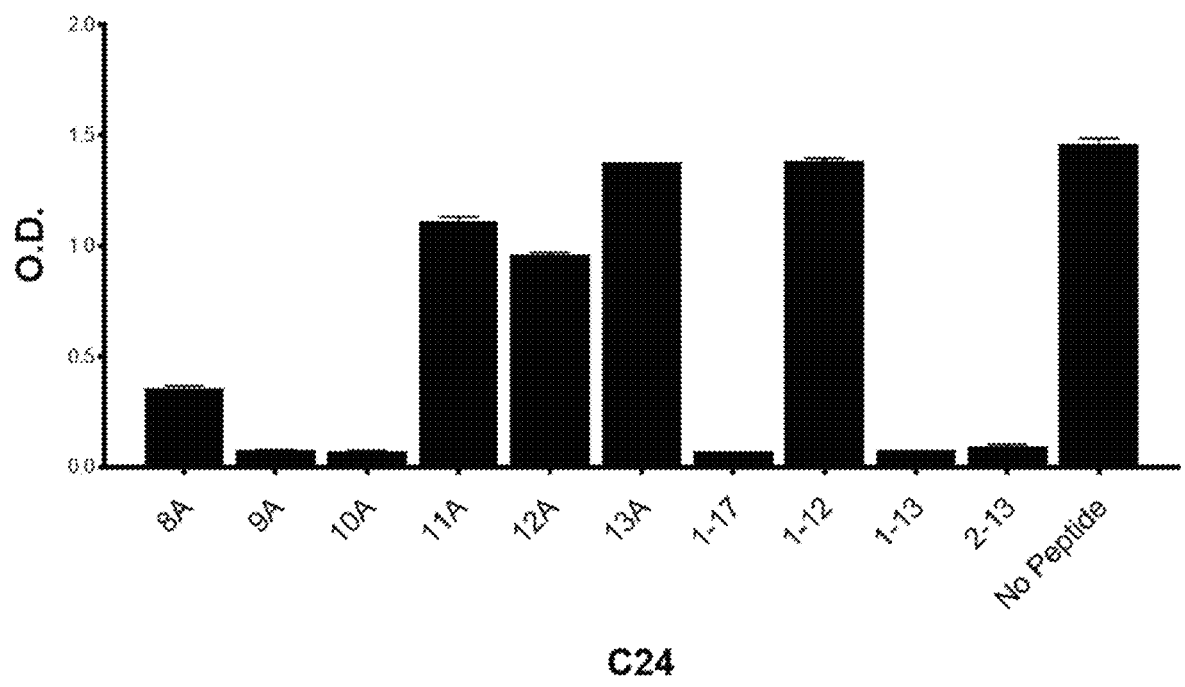
Figure 4C:
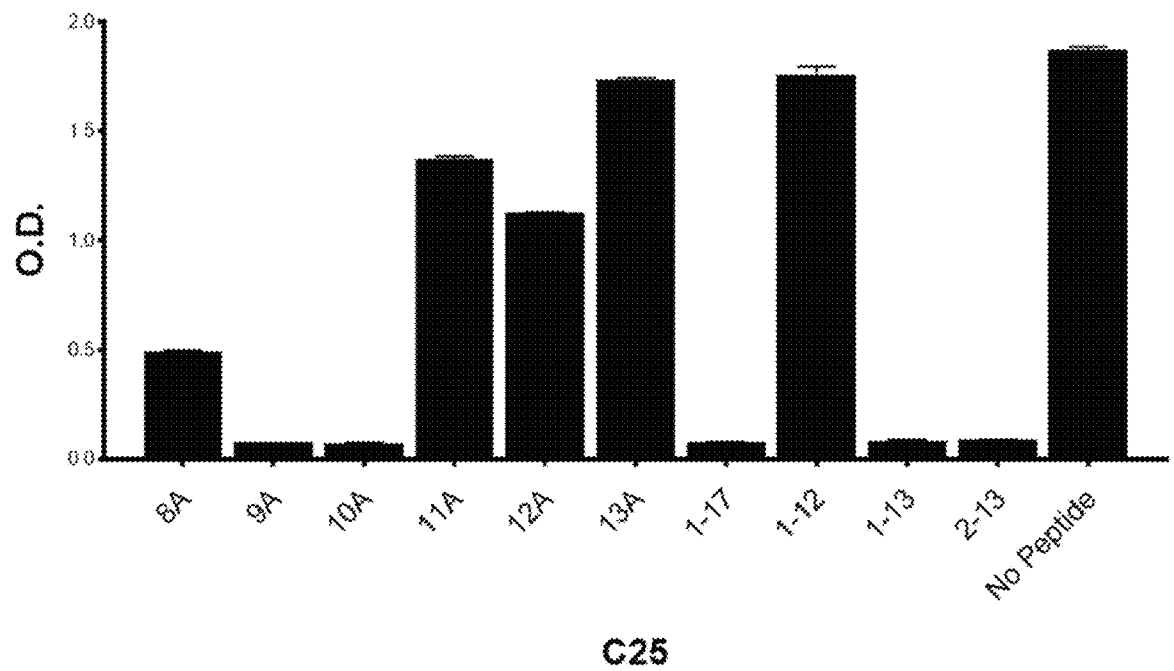

To further understand the importance of the amino acids in the epitope 8-13 (KGPMPF (SEQ ID NO:188)) in the binding of the epitope by mAb C8, C14, or C25, alanine scanning peptides (Table 8) were generated and assessed for their ability to inhibit the binding of biotin-apelin-13 (SEQ ID NO:165) to these mAbs using the ELISA-based peptide competition assay described above. Inhibition of biotin-apelin-13 (SEQ ID NO:165) binding to the anti-apelin mAb C8, C24, or C25 by the alanine scanning peptides are shown in FIGS. 4A-4C. Each peptide or control sample was assayed in duplicate for a given mAb. As shown in FIG. 4A, peptide 8A still blocks binding of biotin-apelin-13 (SEQ ID NO:165) to C8 but to a less extent compared with apelin 13 (peptide 1-13), 9A, or 10A. Peptides 11A, 12A, and 13A largely lost the ability to block the binding of biotin-apelin-13 (SEQ ID NO:165) to C8. These data indicate that the side chains of residues 11, 12, and 13 are required for apelin binding to C8, and the side chain of residue 8 has some contribution to C8 binding; the side chains of residues 9 and 10 are not important for C8 binding. The same results were observed for C24 and C25 as shown in FIGS. 4B and 4C.

TABLE 7

Apelin peptides used in the competition assay for anti-apelin mAbs C8, C24, and C25.

| Peptide | Sequence | SEQ ID NO: |
|---|---|---|
| 1-17 | KFRRQRPRLSHKGPMPF | 166 |
| 1-13 | QRPRLSHKGPMPF | 165 |
| 1-12 | QRPRLSHKGPMP | 181 |
| 2-13 | RPRLSHKGPMPF | 182 |
| 3-13 | PRLSHKGPMPF | 183 |
| 4-13 | RLSHKGPMPF | 184 |
| 5-13 | LSHKGPMPF | 185 |
| 6-13 | SHKGPMPF | 186 |
| 7-13 | HKGPMPF | 187 |
| 8-13 | KGPMPF | 188 |
| 9-13 | GPMPF | 189 |
| 10-13 | PMPF | 190 |
| 11-13 | MPF | 191 |

TABLE 8

Alanine scanning peptides derived from the epitope 8-13 used in the competition assay for anti-apelin mAbs C8, C24 and C25

| Peptide | Sequence | SEQ ID NO: |
|---|---|---|
| 8A | AGPMPF | 192 |
| 9A | KAPMPF | 193 |
| 10A | KGAMPF | 194 |
| 11A | KGPAPF | 195 |
| 12A | KGPMAF | 196 |
| 13A | KGPMPA | 197 |

Figure 5A:
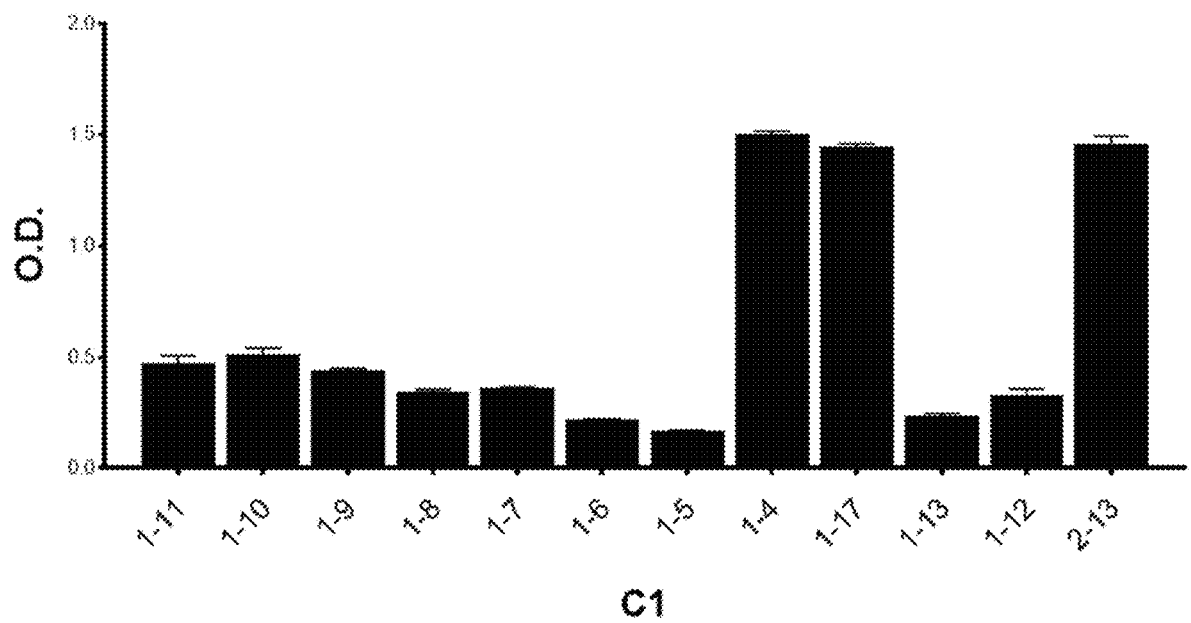
FIGS. 5A-5C show graphs demonstrating the inhibition of apelin-13-biotin ((QRPRLSHKGPMPF-biotin (SEQ ID NO:165)) binding to the anti-apelin mAbs C1, C6 and C7 by the competition peptides in Table 9 as measured by ELISA. Goat-anti-rabbit IgG was immobilized on an ELISA plate. A mixture of a rabbit anti-apelin mAb (C1, C6, or C7) and a competition peptide was preincubated for 30 minutes at room temperature and then apelin-13-biotin (SEQ ID NO:165) was added, mixed and the final solution was added on the plate. The binding of apelin-13-biotin (SEQ ID NO:165) to the immobilized anti-apelin mAbs, C1 (FIG. 5A), C6 (FIG. 5B), and C7 (FIG. 5C), was detected by adding streptavidin-conjugated to alkaline phosphatase and PNPP substrate, and measured as the absorbance at 405 nm.
Figure 5B:
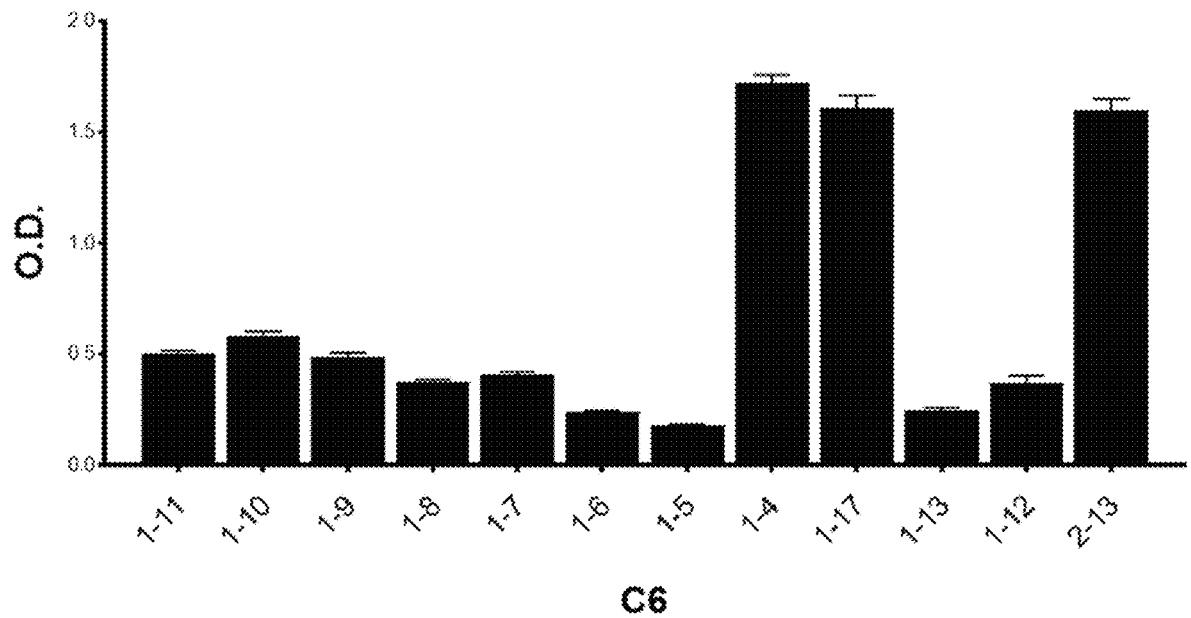
Figure 5C:
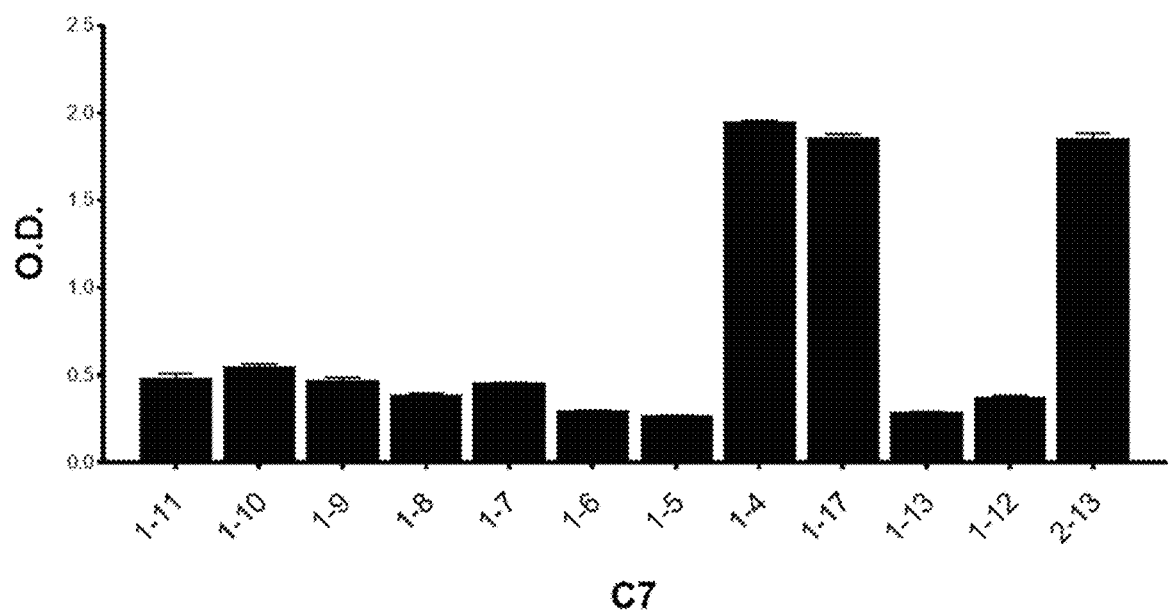

The antibody binding sites for anti-apelin mAbs C1, C6, and C7 were mapped with the ELISA-based peptide competition assay described above using apelin-13-biotin (QRPRLSHKGPMPF-biotin (SEQ ID NO:165)) and the competition peptides shown in Table 9. Inhibition of apelin-13-biotin (SEQ ID NO:165) binding to the anti-apelin mAbs C1, C6, and C7 by the competition peptides are shown in FIGS. 5A-5C. As shown in FIG. 5A, when one amino acid is deleted from the N-terminus of apelin 13, the peptide does not bind to C1. Serial deletion of the C-terminal amino acids of apelin 13 does not have an effect on its binding to C1 until residue number 5 is deleted. Interestingly, C1 does not bind to apelin 17 (peptide 1-17 in Table 9), suggesting that the free N-terminal end of apelin-13 is important for C1 binding.

The mapping result indicates that C1 binds to the epitope comprising amino acids QRPRL (SEQ ID NO: 204) (peptide 1-5 in Table 9). The same results were observed for C6 and C7.

Figure 6A:
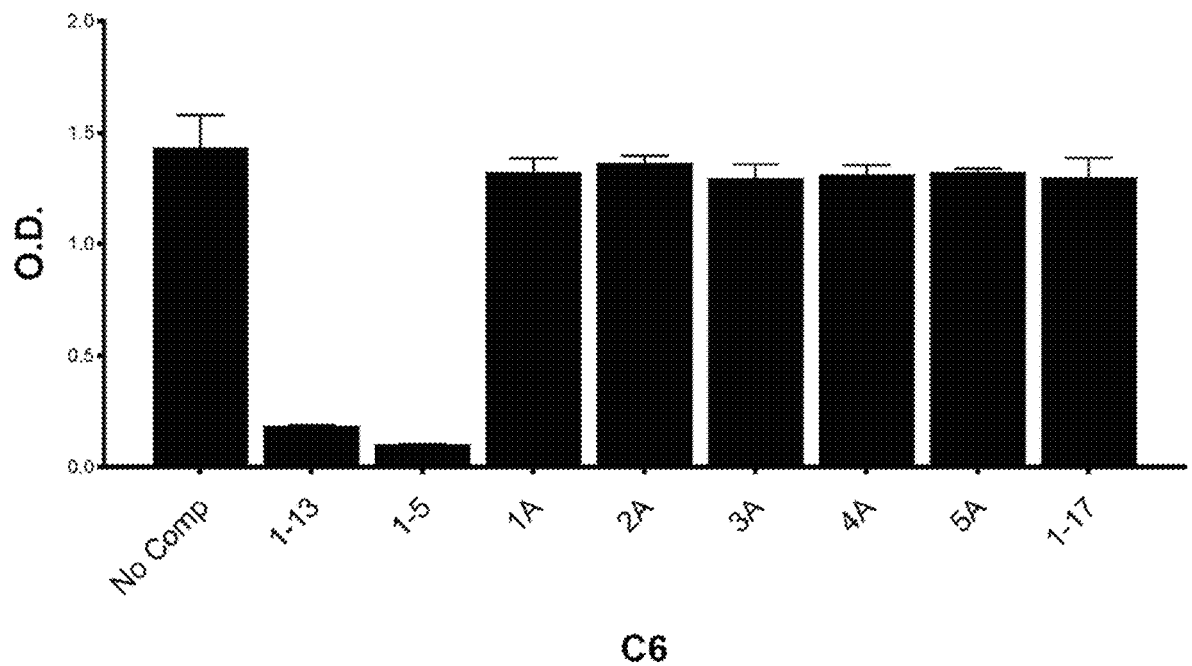
FIGS. 6A-6B show graphs demonstrating the inhibition of apelin-13-biotin (SEQ ID NO:165) binding to the anti-apelin mAbs C6 (FIG. 6A) and C7 (FIG. 6B) by the alanine scanning peptides (Table 10) derived from epitope 1-5 (QRPRL (SEQ ID NO: 204)) as measured by ELISA described above.
Figure 6B:
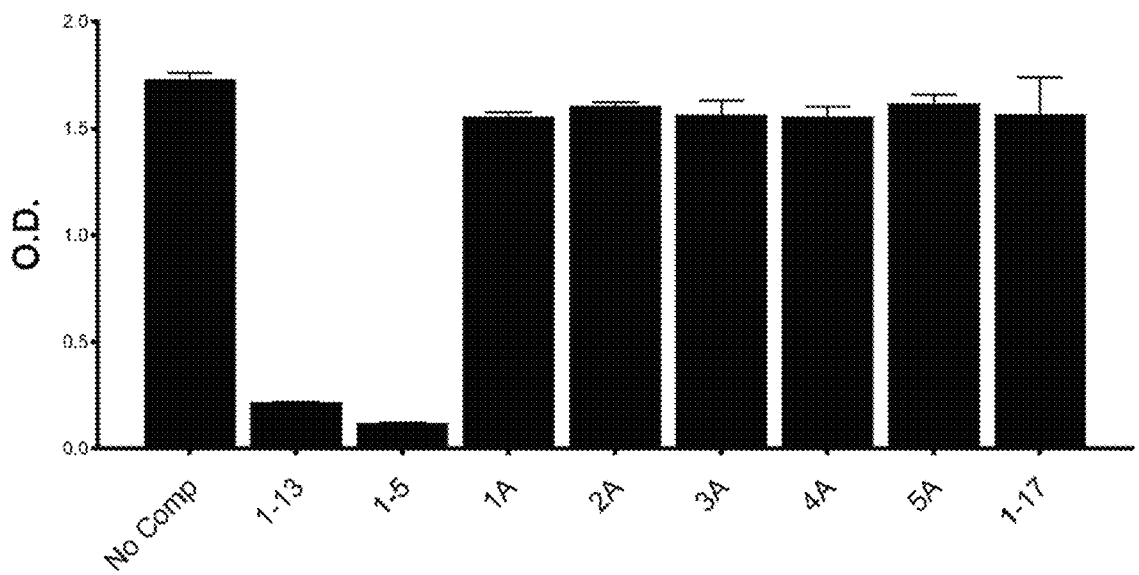

To further understand the importance of the amino acids in the epitope 1-5 (QRPRL (SEQ ID NO: 204)) in the binding of the epitope by mAb C6 or C7, alanine scanning peptides (Table 10) were generated and assessed for their ability to inhibit the binding of apelin-13-biotin (SEQ ID NO:165) to these mAbs using the ELISA-based peptide competition assay described above. Inhibition of apelin-13-biotin (SEQ ID NO:165) binding to the anti-apelin mAb C6 or C7 by the alanine scanning peptides are shown in FIGS. 6A-6B. Each peptide or control sample was assayed in duplicate for a given mAb. As shown in FIGS. 6A and 6B, peptides 1A, 2A, 3A, 4A and 5A lost the ability to block the binding of apelin-13-biotin (SEQ ID NO:165) to C6 or C7. These data indicate that the side chains of residues 1, 2, 3, 4, and 5 are required for apelin binding to C6 or C7.

TABLE 9

Apelin peptides used in the competition assay for anti-apelin mAbs C1, C6 and C7

| Peptide | Sequence | SEQ ID NO: |
|---|---|---|
| 1-17 | KFRRQRPRLSHKGPMPF | 166 |
| 1-13 | QRPRLSHKGPMPF | 165 |
| 2-13 | RPRLSHKGPMPF | 182 |
| 1-12 | QRPRLSHKGPMP | 181 |
| 1-11 | QRPRLSHKGPM | 198 |
| 1-10 | QRPRLSHKGP | 199 |
| 1-9 | QRPRLSHKG | 200 |
| 1-8 | QRPRLSHK | 201 |
| 1-7 | QRPRLSH | 202 |
| 1-6 | QRPRLS | 203 |
| 1-5 | QRPRL | 204 |
| 1-4 | QRPR | 205 |

TABLE 10

Alanine scanning peptides derived from the epitope 1-5 used in the competition assay for anti-apelin mAbs C6 and C7

| Peptide | Sequence | SEQ ID NO: |
|---|---|---|
| 1A | ARPRL | 206 |
| 2A | QAPRL | 207 |
| 3A | QRARL | 208 |
| 4A | QRPAL | 209 |
| 5A | QRPRA | 210 |

Example 7: Humanization of Anti-Apelin mAbs

The rabbit anti-apelin mAb C8 was humanized to reduce the potential of immunogenicity when used in human patients. The sequences of the variable regions of the heavy and light chains (VH and VL) were compared with the human antibody sequences in the Protein Data Bank (PDB) database and a homology model was built by applying SWISS-modeling. The CDRs in both the heavy and light chains of the rabbit mAb were grafted into human frameworks that have the highest possibility of maintaining the proper structure likely required for antigen binding. Back-mutations from human residue to rabbit residue were designed when necessary. The sequences of the humanized VH and VL regions are shown in Table 11 and Table 12, respectively. The humanized VH and VL regions were fused to human IgG1 heavy chain and kappa light chain constant regions, respectively, to generate humanized mAbs. Constructs corresponding to the mAb sequences were used for transient transfection in HEK 293 cells and the supernatants were analyzed for the affinity of each humanized mAb for apelin. The KD values of the humanized mAbs were determined on Biacore using biotin-apelin-13 (biotin-QR-PRLSHKGPMPF (SEQ ID NO:165)). The data are shown in Table 13.

Two additional humanized mAbs (B24 and B25) were generated with sequence modifications on A31. These three mAbs (A31, B24, and B25) were cloned on human IgG4 backbone and tested in an ELISA assay where increasing concentrations of antibodies were immobilized on plates and biotin-apelin-13 (biotin-QRPRLSHKGPMPF (SEQ ID NO:165)) was added for binding, followed by binding with streptavidin-conjugated to alkaline phosphatase. The binding was then detected by adding PNPP substrate and reading absorbance of the ELISA plates at 405 nm. The EC50 values for the ELISA binding curves are shown in Table 14.

Figure 7A:
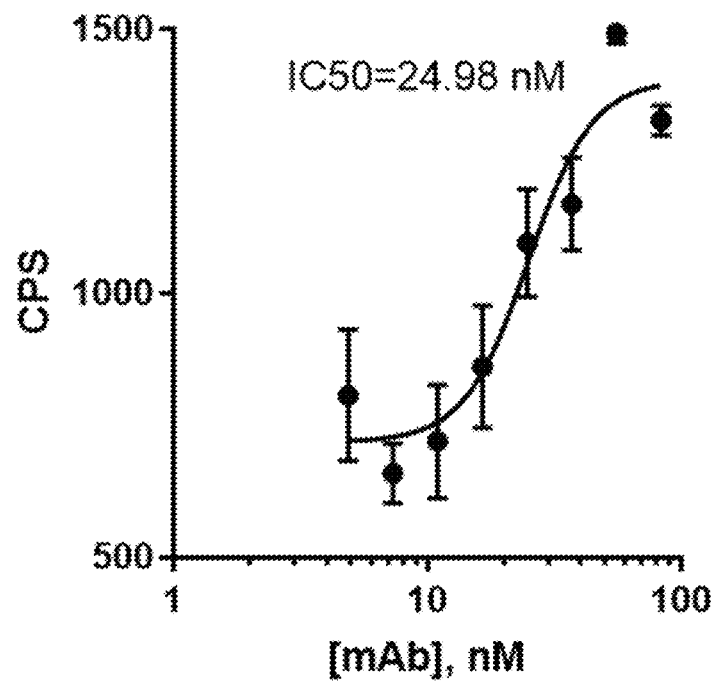
FIGS. 7A-7B show the IC50 curves of humanized anti-apelin mAb A31 in a cell-based assay. Apelin activity was assessed for its ability to downregulate the forskolin (FSK)-induced cAMP production in cAMP Hunter™ CHO-K1 AGTRL1 Gi cells (DiscoverX #95-0147C2) and the activity of the anti-apelin mAb was assessed for its ability to reverse the inhibitory effect of apelin.
Figure 7B:
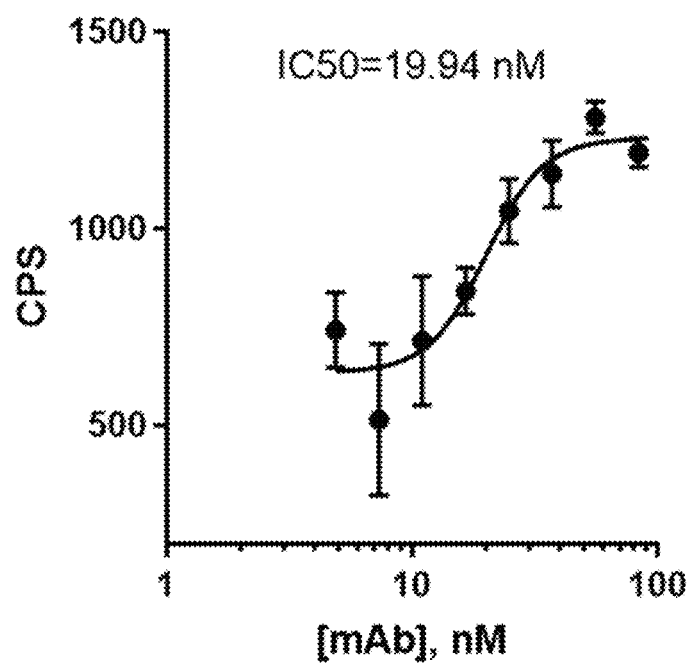

The IC50 curves of humanized anti-apelin mAb A31 (on human IgG1 backbone) were generated using a cell-based assay as described above. Apelin activity was assessed for its ability to downregulate the forskolin (FSK)-induced cAMP production in cAMP Hunter™ CHO-K1 AGTRL1 Gi cells (DiscoverX #95-0147C2) and the activity of the anti-apelin mAb was assessed for its ability to reverse the inhibitory effect of apelin. FIG. 7A shows an IC50 graph when apelin 13 (APL13) was used in the assay; FIG. 7B shows an IC50 graph when pyro-apelin 13 (pyroAPL13) was used in the assay. CPS, counts per second.

Figure 8:
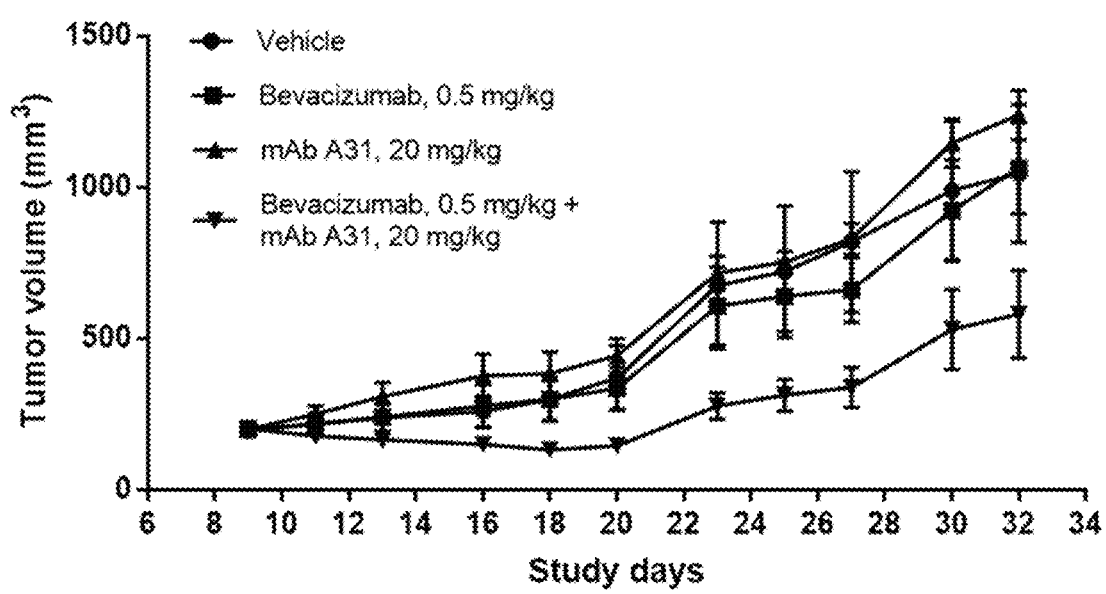
FIG. 8 shows the effect of humanized anti-apelin mAb A31 on tumor growth in a xenograft model. The mAb was tested either alone or in combination with bevacizumab; bevacizumab alone was also included in the study.

The effect of anti-apelin mAb A31 (on human IgG1 backbone) on tumor growth was tested in a mouse xenograft model. HUCCT1 cells ($1 \times 10^7$) were implanted to NOD/SCID mice and grown until tumors reached 150-200 mm$^3$. After randomization (n=3 per group), mice were dosed with either vehicle, 0.5 mg/kg bevacizumab, 20 mg/kg mAb A31, or a combination of 0.5 mg/kg bevacizumab and 20 mg/kg mAb A31. Doses were given via intraperitoneal injection 3 times per week and tumor volumes were measured on the same day. FIG. 8 shows the tumor volumes in different groups during the study. The data indicate that the combination of mAb A31 with bevacizumab has a strong inhibitory effect on tumor growth.

TABLE 11

Sequences of heavy chain variable regions of humanized anti-apelin mAbs

| mAb clones | VH |
|---|---|
| A11 | QSLEESGGGLVQPGGSLRLSCAVSGIDLYSNRMSWVRQAPGKGLEWVSSIGSSPWYASWAQGRFTISRDNSNTLYLQMNSLTAEDTAVYYCAKGGYRPGASVWGQGTLVTVSS (SEQ ID NO: 211) |
| A21 | QSLEESGGGLVQPGGSLRLSCAVSGIDLYSNRMSWVRQAPGKGLEWVSSIGSSPWYASWAQGRFTISRDNSNTVYLQMNSLTAEDTATYFCAKGGYRPGASVWGQGTLVTVSS (SEQ ID NO: 212) |
| A31 | QSLEESGGGLVQPGGSLRLSCAVSGIDLYSNRMSWVRQAPGKGLEWVGSIGSSPWYASWAQGRFTISRDNSNTVYLQMNSLTAEDTATYFCAKGGYRPGASVWGQGTLVTVSS (SEQ ID NO: 213) |
| A41 | QSLEESGGGLVQPGGSLRLSCTVSGIDLYSNRMSWVRQAPGKGLEWVGSIGSSPWYASWAQGRFTISRDNSNTVYLKMNSPTAEDTATYFCAKGGYRPGASVWGQGTLVTVSS (SEQ ID NO: 214) |
| A33 | QSLEESGGGLVQPGGSLRLSCAVSGIDLYSNRMSWVRQAPGKGLEWVGSIGSSPWYASWAQGRFTISRDNSNTVYLQMNSLTAEDTATYFCAKGGYRPGASVWGQGTLVTVSS (SEQ ID NO: 213) |
| A43 | QSLEESGGGLVQPGGSLRLSCTVSGIDLYSNRMSWVRQAPGKGLEWVGSIGSSPWYASWAQGRFTISRDNSNTVYLKMNSPTAEDTATYFCAKGGYRPGASVWGQGTLVTVSS (SEQ ID NO: 214) |
| B24 | QSLEESGGGLVQPGGSLRLSCTVSGIDLYTNRVSWVRQAPGKGLEWVGSIGSSPWYASWAQGRFTISRDNSNTVYLKMNSPTAEDTATYFCAKGGYRPGGSIWGQGTLVTVSS (SEQ ID NO: 217) |
| B25 | QSLEESGGGLVQPGGSLRLSCTVSGIDLYTNRMSWVRQAPGKGLEWVGSIGSSPWFASWALGRFTISRDNSNTVYLKMNSPTAEDTATYFCAKGGYRPGASVWGQGTLVTVSS (SEQ ID NO: 218) |

VH: heavy chain variable region

TABLE 12

Sequences of light chain variable regions of humanized anti-apelin mAbs

| mAb clones | VL |
|---|---|
| A11 | DIQLTQSPSSLSASVGDRVTITCQSSQSIYDNNDLAWYQQKPGKTPKRLIYLASS LDSGVPSRFSGSGSGTDFTLTISSLQPEDVATYYCAGGYSGDIYTFGGGTKVEIK (SEQ ID NO: 215) |
| A21 | DIQLTQSPSSLSASVGDRVTITCQSSQSIYDNNDLAWYQQKPGKTPKRLIYLASS LDSGVPSRFSGSGSGTDFTLTISSLQPEDVATYYCAGGYSGDIYTFGGGTKVEIK (SEQ ID NO: 215) |
| A31 | DIQLTQSPSSLSASVGDRVTITCQSSQSIYDNNDLAWYQQKPGKTPKRLIYLASS LDSGVPSRFSGSGSGTDFTLTISSLQPEDVATYYCAGGYSGDIYTFGGGTKVEIK (SEQ ID NO: 215) |
| A41 | DIQLTQSPSSLSASVGDRVTITCQSSQSIYDNNDLAWYQQKPGKTPKRLIYLASS LDSGVPSRFSGSGSGTDFTLTISSLQPEDVATYYCAGGYSGDIYTFGGGTKVEIK (SEQ ID NO: 215) |
| A33 | AQVLTQSPSSLSASVGDRVTIACQSSQSVYDNNDLAWYQQKAGQTPKRLIYLA SSLDSGVPSRFSGSGSGTEFTLTISSLQCEDVATYYCAGGYSGDIYTFGGGTEVV VE (SEQ ID NO: 216) |
| A43 | AQVLTQSPSSLSASVGDRVTIACQSSQSVYDNNDLAWYQQKAGQTPKRLIYLA SSLDSGVPSRFSGSGSGTEFTLTISSLQCEDVATYYCAGGYSGDIYTFGGGTEVV VE (SEQ ID NO: 216) |
| B24 | DIQLTQSPSSLSASVGDRVTITCQSSQSIYDNNDLGWYQQKPGKTPKRLIYLASS LDSGVPSRFSGSGSGTDFTLTISSLQPEDVATYYCAGGYSGDIYTFGGGTKVEIK (SEQ ID NO: 219) |
| B25 | DIQLTQSPSSLSASVGDRVTITCQSSQSIYDNNDLAWYQQKPGKTPKRLIYLASS LDSGVPSRFSGSGSGTDFTLTISSLQPEDVATYYCAGGYNGDIYTFGGGTKVEIK (SEQ ID NO: 220) |

VL: light chain variable region

TABLE 13

KD values of humanized anti-apelin mAbs from Biacore assay

| mAb clones | KD |
|---|---|
| A11 | 0.126 pM |
| A21 | 1.65 fM |
| A31 | 0.148 pM |
| A41 | 0.067 pM |
| A33 | 0.0143 pM |
| A43 | 3.26 pM |

TABLE 14

ELISA binding EC50 values for humanized mAbs

| mAb clones | EC50 (nM) |
|---|---|
| A31 | 0.21 |
| B24 | 0.79 |
| B25 | 0.47 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. An isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequences of:
   (1) SEQ ID NOs: 41, 42, 43, 101, 102, and 103, respectively;
   (2) SEQ ID NOs: 44, 45, 46, 104, 105, and 106, respectively; or
   (3) SEQ ID NOs: 47, 48, 49, 107, 108, and 109, respectively;
wherein the antibody or antigen-binding fragment thereof specifically binds apelin.

2. The isolated monoclonal antibody or antigen-binding fragment of claim 1, comprising:
   (a) a heavy chain variable region having a polypeptide sequence at least 95% identical to SEQ ID NO:1, and a light chain variable region having a polypeptide sequence at least 95% identical to SEQ ID NO:2;
   (b) a heavy chain variable region having a polypeptide sequence at least 95% identical to SEQ ID NO:3, and a light chain variable region having a polypeptide sequence at least 95% identical to SEQ ID NO:4;
   (c) a heavy chain variable region having a polypeptide sequence at least 95% identical to SEQ ID NO:5, and a light chain variable region having a polypeptide sequence at least 95% identical to SEQ ID NO:6;
   (d) a heavy chain variable region having a polypeptide sequence at least 95% identical to SEQ ID NO:213, and a light chain variable region having a polypeptide sequence at least 95% identical to SEQ ID NO:216; or
   (e) a heavy chain variable region having a polypeptide sequence at least 95% identical to SEQ ID NO:214, and a light chain variable region having a polypeptide sequence at least 95% identical to SEQ ID NO:216.

3. The isolated monoclonal antibody or antigen-binding fragment thereof of claim 1, wherein the isolated monoclonal antibody or antigen-binding fragment thereof specifically binds to an epitope with the amino acid sequence of SEQ ID NO:188, wherein binding of the monoclonal antibody or antigen-binding fragment thereof to apelin inhibits apelin-mediated signaling through the apelin receptor and neutralizes apelin activity.

4. The isolated monoclonal antibody or antigen-binding fragment thereof of claim 3, wherein any one of the side chains of residues 11, 12, or 13 of apelin-13 is required for binding to the epitope comprising the amino acid sequence of SEQ ID NO:188.

5. The isolated monoclonal antibody or antigen-binding fragment of claim 1, wherein the antibody or antigen-binding fragment thereof is chimeric and/or humanized.

6. An isolated nucleic acid encoding the monoclonal antibody or antigen-binding fragment of claim 1.

7. A vector comprising the isolated nucleic acid of claim 6.

8. A host cell comprising the vector of claim 7.

9. A pharmaceutical composition comprising the isolated monoclonal antibody or antigen-binding fragment of claim 1 and a pharmaceutically acceptable carrier.

10. The isolated monoclonal antibody or antigen-binding fragment thereof of claim 3, wherein the monoclonal antibody or antigen-binding fragment thereof binds to the C-terminal end of apelin-13, pyro-apelin-13, apelin-17, apelin-36, apelin-55, and/or other forms of apelin that share the same C-terminal end with apelin-13.

11. The isolated monoclonal antibody or antigen-binding fragment thereof of claim 1, wherein the monoclonal antibody or antigen-binding fragment thereof specifically binds human apelin.

12. An isolated monoclonal antibody or antigen-binding fragment thereof comprising:
(a) a heavy chain variable region having the polypeptide sequence of SEQ ID NO:1, and a light chain variable region having the polypeptide sequence of SEQ ID NO:2;
(b) a heavy chain variable region having the polypeptide sequence of SEQ ID NO:3, and a light chain variable region having the polypeptide sequence of SEQ ID NO:4;
(c) a heavy chain variable region having the polypeptide sequence of SEQ ID NO:5, and a light chain variable region having the polypeptide sequence of SEQ ID NO:6;
(d) a heavy chain variable region having the polypeptide sequence of SEQ ID NO:211, and a light chain variable region having the polypeptide sequence of SEQ ID NO:215;
(e) a heavy chain variable region having the polypeptide sequence of SEQ ID NO:212, and a light chain variable region having the polypeptide sequence of SEQ ID NO:215;
(f) a heavy chain variable region having the polypeptide sequence of SEQ ID NO:213, and a light chain variable region having the polypeptide sequence of SEQ ID NO:215;
(g) a heavy chain variable region having the polypeptide sequence of SEQ ID NO:214, and a light chain variable region having the polypeptide sequence of SEQ ID NO:215;
(h) a heavy chain variable region having the polypeptide sequence of SEQ ID NO:213, and a light chain variable region having the polypeptide sequence of SEQ ID NO:216;
(i) a heavy chain variable region having the polypeptide sequence of SEQ ID NO:214, and a light chain variable region having the polypeptide sequence of SEQ ID NO:216;
(j) a heavy chain variable region having the polypeptide sequence of SEQ ID NO:217, and a light chain variable region having the polypeptide sequence of SEQ ID NO:219; or
(k) a heavy chain variable region having the polypeptide sequence of SEQ ID NO:218, and a light chain variable region having the polypeptide sequence of SEQ ID NO:220.

13. The isolated monoclonal antibody or antigen-binding fragment thereof of claim 12, wherein the isolated monoclonal antibody or antigen-binding fragment thereof specifically binds to an epitope with the amino acid sequence of SEQ ID NO:188, wherein binding of the monoclonal antibody or antigen-binding fragment thereof to apelin inhibits apelin-mediated signaling through the apelin receptor and neutralizes apelin activity.

14. The isolated monoclonal antibody or antigen-binding fragment thereof of claim 13, wherein any one of the side chains of residues 11, 12, or 13 of apelin-13 is required for binding to the epitope comprising the amino acid sequence of SEQ ID NO:188.

15. An isolated nucleic acid encoding the monoclonal antibody or antigen-binding fragment of claim 12.

16. A vector comprising the isolated nucleic acid of claim 15.

17. A host cell comprising the vector of claim 16.

18. A pharmaceutical composition comprising the isolated monoclonal antibody or antigen-binding fragment of claim 12 and a pharmaceutically acceptable carrier.

19. The isolated monoclonal antibody or antigen-binding fragment thereof of claim 13, wherein the monoclonal antibody or antigen-binding fragment thereof binds to the C-terminal end of apelin-13, pyro-apelin-13, apelin-17, apelin-36, apelin-55, and/or other forms of apelin that share the same C-terminal end with apelin-13.

20. The isolated monoclonal antibody or antigen-binding fragment thereof of claim 12, wherein the monoclonal antibody or antigen-binding fragment thereof specifically binds human apelin.

21. A method of blocking binding of apelin to an apelin receptor in a subject in need thereof, comprising administering to the subject the pharmaceutical composition of claim 9.

22. A method of treating a disease selected from the group consisting of a diabetic retinopathy (DR), an age-related macular degeneration (AMD), a diabetic macular edema (DME), a macular edema following retinal vein occlusion (RVO), a retinal degeneration, a myopic choroidal neovascularization (mCNV), a diabetic nephropathy, a chronic kidney disease (CKD), a non-alcoholic steatohepatitis (NASH), a liver cirrhosis, a plaque neovascularization, a rubeosis iridis, a neovascular glaucoma, a corneal neovascularization (CNV) a retinopathy of prematurity (ROP), a retinopathy, a macular degeneration, an ovarian hyperstimulation syndrome (OHSS), a uterine bleeding, an endometriosis, an endometrial hyperplasia, a myometrial leiomyomas, an adenomyosis, a tissue fibrosis, and a cancer in a subject in need thereof, comprising administering to the subject the pharmaceutical composition of claim 9.

23. The method of claim 22, wherein the disease is cancer and the pharmaceutical composition further comprises an anti-cancer agent.

24. The method of claim 23, wherein the anti-cancer agent is an anti-VEGF agent, wherein the anti-VEGF agent is selected from an anti-VEGF antibody, bevacizumab, randibizumab, aflibercept, or conbercept.

25. A method of determining a level of apelin in a subject, the method comprising:
   a) obtaining a sample from the subject;
   b) contacting the sample with the monoclonal antibody or antigen-binding fragment thereof of claim 1; and
   c) determining a level of apelin in the subject.

26. The method of claim 25, wherein the sample is a tissue sample or a blood sample.

27. The method of claim 26, wherein the tissue sample is a cancer tissue sample.

28. A method of producing the monoclonal antibody or antigen-binding fragment of claim 1, comprising culturing a cell comprising a nucleic acid encoding the monoclonal antibody or antigen-binding fragment of claim 1 under conditions to produce the monoclonal antibody or antigen-binding fragment, and recovering the antibody or antigen-binding fragment from the cell or culture.

29. A method of blocking binding of apelin to an apelin receptor in a subject in need thereof, comprising administering to the subject the pharmaceutical composition of claim 18.

30. A method of treating a disease selected from the group consisting of a diabetic retinopathy (DR), an age-related macular degeneration (AMD), a diabetic macular edema (DME), a macular edema following retinal vein occlusion (RVO), a retinal degeneration, a myopic choroidal neovascularization (mCNV), a diabetic nephropathy, a chronic kidney disease (CKD), a non-alcoholic steatohepatitis (NASH), a liver cirrhosis, a plaque neovascularization, a rubeosis iridis, a neovascular glaucoma, a corneal neovascularization (CNV), a retinopathy of prematurity (ROP), a retinopathy, a macular degeneration, an ovarian hyperstimulation syndrome (OHSS), a uterine bleeding, an endometriosis, an endometrial hyperplasia, a myometrial leiomyomas, an adenomyosis, a tissue fibrosis, and a cancer in a subject in need thereof, comprising administering to the subject the pharmaceutical composition of claim 18.

31. The method of claim 30, wherein the disease is cancer and the pharmaceutical composition further comprises an anti-cancer agent.

32. The method of claim 31, wherein the anti-cancer agent is an anti-VEGF agent, wherein the anti-VEGF agent is selected from an anti-VEGF antibody, bevacizumab, randibizumab, aflibercept, or conbercept.

33. A method of determining a level of apelin in a subject, the method comprising:
   a) obtaining a sample from the subject;
   b) contacting the sample with the monoclonal antibody or antigen-binding fragment thereof of claim 12; and
   c) determining a level of apelin in the subject.

34. The method of claim 33, wherein the sample is a tissue sample or a blood sample.

35. The method of claim 34, wherein the tissue sample is a cancer tissue sample.

36. A method of producing the monoclonal antibody or antigen-binding fragment of claim 12, comprising culturing a cell comprising a nucleic acid encoding the monoclonal antibody or antigen-binding fragment of claim 12 under conditions to produce the monoclonal antibody or antigen-binding fragment, and recovering the antibody or antigen-binding fragment from the cell or culture.

\* \* \* \* \*